(12) United States Patent
Gonzalez et al.

(10) Patent No.: US 12,391,937 B2
(45) Date of Patent: *Aug. 19, 2025

(54) BIOSYNTHESIS OF PRODUCTS FROM 1-CARBON COMPOUNDS

(71) Applicant: Mojia Biotech Pte. Ltd., Singapore (SG)

(72) Inventors: Ramon Gonzalez, Tampa, FL (US); Alexander Chou, Houston, TX (US); James Clomburg, Houston, TX (US)

(73) Assignee: Mojia Biotech Pte. Ltd., Singapore (SG)

( * ) Notice: Subject to any disclaimer, the term of this patent is extended or adjusted under 35 U.S.C. 154(b) by 359 days.

This patent is subject to a terminal disclaimer.

(21) Appl. No.: 17/510,641

(22) Filed: Oct. 26, 2021

(65) Prior Publication Data

US 2022/0112477 A1   Apr. 14, 2022

Related U.S. Application Data

(63) Continuation of application No. 15/523,284, filed as application No. PCT/US2015/058121 on Oct. 29, 2015, now Pat. No. 11,186,834.

(60) Provisional application No. 62/069,850, filed on Oct. 29, 2014.

(51) Int. Cl.
| | |
|---|---|
| C12N 9/88 | (2006.01) |
| C12N 15/52 | (2006.01) |
| C12N 15/70 | (2006.01) |
| C12P 1/04 | (2006.01) |
| C12P 5/02 | (2006.01) |
| C12P 7/04 | (2006.01) |
| C12P 7/20 | (2006.01) |
| C12P 7/24 | (2006.01) |
| C12P 7/40 | (2006.01) |
| C12P 11/00 | (2006.01) |
| C12P 13/00 | (2006.01) |

(52) U.S. Cl.
CPC .............. *C12N 9/88* (2013.01); *C12N 15/52* (2013.01); *C12N 15/70* (2013.01); *C12P 1/04* (2013.01); *C12P 5/02* (2013.01); *C12P 7/04* (2013.01); *C12P 7/20* (2013.01); *C12P 7/24* (2013.01); *C12P 7/40* (2013.01); *C12P 11/00* (2013.01); *C12P 13/001* (2013.01); *C12Y 401/00* (2013.01); *Y02P 20/141* (2015.11)

(58) Field of Classification Search
CPC ... C12N 15/52; C12N 9/88; C12P 1/04; C12P 7/04; C12P 7/40
USPC ....................................................... 435/146
See application file for complete search history.

(56) References Cited

U.S. PATENT DOCUMENTS

| | | | |
|---|---|---|---|
| 7,262,046 | B2 | 8/2007 | Ka-Yiu et al. |
| 7,569,380 | B2 | 8/2009 | Dittrich et al. |
| 8,129,157 | B2 | 3/2012 | Gonzalez et al. |
| 8,691,552 | B2 | 4/2014 | Gonzalez et al. |
| 8,795,991 | B2 | 8/2014 | Bennett et al. |
| 8,962,272 | B2 | 2/2015 | San et al. |
| 10,513,716 | B2 | 12/2019 | Osterhout et al. |
| 2013/0031641 | A1 | 1/2013 | Fisk et al. |
| 2013/0196359 | A1 | 8/2013 | Siegel et al. |
| 2013/0316413 | A1 | 11/2013 | Gonzalez et al. |
| 2014/0179942 | A1 | 6/2014 | Finnegan |
| 2014/0256904 | A1 | 9/2014 | Schaffer et al. |
| 2014/0273110 | A1 | 9/2014 | Gonzalez et al. |
| 2019/0100741 | A1 | 4/2019 | Gonzalez et al. |
| 2022/0112477 | A1 | 4/2022 | Gonzalez et al. |

FOREIGN PATENT DOCUMENTS

| | | |
|---|---|---|
| CN | 103797109 A | 5/2014 |
| CN | 103857793 A | 6/2014 |
| EP | 3786290 A1 | 3/2021 |
| TW | 201420761 A | 6/2014 |
| WO | 2012/109176 A1 | 11/2013 |
| WO | 2016069929 A1 | 5/2016 |
| WO | 2017161041 A1 | 9/2017 |
| WO | 2017190056 A1 | 11/2017 |

OTHER PUBLICATIONS

International Search Report for parent case, App. No. PCT/US15/058121, Issued Mar. 11, 2016.
Uniprot List, KeGG, Aug. 9, 2020, pp. 1-4.

(Continued)

*Primary Examiner* — Robert B Mondesi
*Assistant Examiner* — Mohammad Y Meah
(74) *Attorney, Agent, or Firm* — Elmore Patent Law Group, P.C.; Mahreen Chaudhry Hoda; Carolyn S. Elmore

(57) ABSTRACT

An engineered microbe that contains a designed platform for the conversion of one-carbon substrates to chemical products is described. The designed platform embodies a new metabolic architecture that consolidates carbon fixation, central metabolism, and product synthesis into a single pathway. This is made possible by the key finding that 2-hydroxyacyl-CoA lyase, an enzyme in the α-oxidation pathway, is capable of catalyzing the C—C bond formation between formyl-CoA and aldehydes of different chain lengths, allowing for the elongation of the carbon backbone of said aldehyde by one-carbon units. These novel microbes present an opportunity for the production of chemicals from single-carbon feedstocks such as carbon dioxide, carbon monoxide, formate, formaldehyde, methanol or methane.

36 Claims, 37 Drawing Sheets

Specification includes a Sequence Listing.

(56) References Cited

OTHER PUBLICATIONS

Casteels, et al., "The role of 2-hydroxyacyl-CoA lyase, a thiamin pyrophosphate-dependent enzyme, in the peroxisomal metabolism of 3-methyl-branched fatty acids and 2-hydroxy straight-chain fatty acids", Biochemical Society Transactions, vol. 35, No. 5, Nov. 2007, 876-880.
Cintolesi, A. et al., "In silico assessment of the metabolic capabilities of an engineered functional reversal of the beta-oxidation cycle for the synthesis of longer-chain (C>/=4) products", Metabolic Engineering, vol. 23, Feb. 22, 2014, 100-115.
Clomburg, J. M. et al., "Integrated engineering of beta-oxidation reversal and omega-oxidation pathways for the synthesis of medium chain omega-functionalized carboxylic acids", Metabolic Engineering, vol. 28, Jan. 28, 2015, 202-212.
Devos, Damien et al., "Practical Limits of Function Prediction", Proteins: Structure, Function, and Genetics, vol. 41, 2000, 98-107.
Fraccascia, P. et al., "Role of Thiamine Pyrophosphate in Oligomerisation, Functioning and Import of Peroxisomal 2-hydroxyacyl-CoA Lyase", Biochimica et Biophysica Acta., 1814(10), 2011, 1226-1233.
Hofmeister, A. et al., "(R)-Lactyl-CoA dehydratase from Clostridium propionicum", European Journal of Biochem. 206(2), 1992, 547-552.
Kim, S. et al., "Synthesis of medium-chain length (C6-C10) fuels and chemicals via beta-oxidation reversal in *Escherichia coli*", Journal of Industrial Microbiology and Biotechnology, vol. 42, Feb. 3, 2015, 465-475.
Kisselev, Lev , "Polypeptide Release Factors in Prokaryotes and Eukaryotes: Same Function, Different Structure", Structure, vol. 10, Jan. 2002, 2002, 8-9.
Mannaerts, G. P. et al., "Peroxisomal lipid Degradation via beta- and alpha-oxidation in mammals", Cell Biochemistry and Biophysics, vol. 32, Dec. 31, 2000, 73-87.
Poehlein, et al., "An Ancient Pathway Combining Carbon Dioxide Fixation with the Generation and Utilization of a Sodium Ion Gradient for ATP Synthesis", PLoS ONE, vol. 7, No. 3, Mar. 29, 2012, e33439.
Schuchmann, K. et al., "Direct and reversible hydrogenation of CO2 to formate by a bacterial ::arbon dioxide reductase", Science {New York, N.Y.), 342(6164), 2013, 1382-5.
Tai, Y-S. et al., "CI metabolism redesigned", Nature Chemical Biology, vol. 11, Jun. 2015, 384-386.
Tobimatsu, T. et al., "Heterologous Expression, Purification, and Properties of Diol Dehydratase, an Adenosylcobalamin-Dependent Enzyme of Klebsiella Oxytoca", Archives of Biochemistry and Biophysics, 347(1), 1997, 132-140.
Whisstock, James C. et al., "Prediction of protein function from protein sequence and structure", Quarterly Reviews of Biophysics, vol. 36 (3), 2003, 307-340.
Witkowski, Andrzej et al., "Conversion of a Beta-Ketoacyl Synthase to a Malonyl Decarboxylase by Replacement of the Active-Site Cysteine with Glutamine", Biochemistry, vol. 38, 1999, 1999, 11643-11650.
Chou, A. , et al., "2-Hydroxyacyl-CoA lyase catalyzes acyloin condensation for one-carbon bioconversion", Nature Chemical Biology, 15(9), 2019, 900-906.
Chou, A. , et al., "2-Hydroxyacyl-CoA lyase catalyzes acyloin condensation for one-carbon bioconversion", Nature Chemical Biology, Supplementary Information, Aug. 5, 2019, 1-26.
Jenkins, B. , et al., "Peroxisomal 2-Hydroxyacyl-CoA Lyase Is Involved in Endogenous Biosynthesis of Heptadecanoic Acid", Molecules, 22, pub 1718, 2017, 1-6.
Kitamura, T. , et al., "Phytosphingosine degradation pathway includes fatty acid α-oxidation reactions in the endoplasmic reticulum", PNAS, 114(13), 2017, E2616-E2623.
MacDonald, L. C, et al., "Engineering broad-spectrum digestion of polyuronides from an exolytic polysaccharide lyase", Biotechnol. Biofuels, 9, pub 43, 2016, 1-14.
MacDonald,, M. C, et al., "Rhodotorula glutinis Phenylalanine/Tyrosine Ammonia Lyase Enzyme Catalyzed Synthesis of the Methyl Ester of para-Hydroxycinnamic Acid and its Potential Antibacterial Activity", Frontiers in Microbiol., 7, Art 281, 2016, 1-11.
Ouellette, R. J, et al., "18—Aldehydes and Ketones", Organic Chemistry Study Guide, 2015, 313-333.
Ramirez-Trujillo, J. , et al., "The Sinorhizobium meliloti glyoxylate cycle enzyme isocitrate lyase (AceA) is required for the utilization of poly-ß-hydroxybutyrate during carbon starvation", Annals of Microbiol., 66, 2016, 921-924.
Sriram, D. , et al., "5-Nitro-2,6-dioxohexahydro-4-pyrimidinecarboxamides: synthesis, in vitro antimycobacterial activity, cytotoxicity, and isocitrate lyase inhibition studies", J Enzyme Inhibition and Med Chem, 25(6), 2010, 765-772.
Wiedner, R. , et al., "Improving the Properties of Bacterial R-Selective Hydroxynitrile Lyases for Industrial Applications", Chem Cat Chem, 7, 2015, 325-332.
Xu, R., et al., "Enzymatic enantioselective transcyanation of silicon-containing aliphatic ketone with (S)-hydroxynitrile lyase from Manihot esculenta", Appl. Microbiol. Biotechnol., 66, 2004, 27-33.
Yan, Q. , et al., "Metabolic engineering of β-oxidation to leverage thioesterases for production of 2-heptanone, 2-nonanone and 2-undecanone", Metabolic Engineering, 61, 2020, 335-343.
Zhang, J. , et al., "Biocatalytic Enantioselective Hydroaminations for Production of N-Cycloalkyl-Substituted L-Aspartic Acids Using Two C—N Lyases", Adv Synth Catal., 361(11), 2019, 2433-2437.
Zhang, C., et al., "KEGG_Extractor: An Effective Extraction Tool for KEGG Orthologs," Genes, 14, 386, 2023.
Expasy Enzyme database (enzyme.expasy.org).
KEGG entries for 2-hydroxyacyl-CoA lyase and oxalyl-CoA-decarboxylase (each accessed on Sep. 12, 2024) Enzyme: 4.1.2.63.
KEGG entries for 2-hydroxyacyl-CoA lyase and oxalyl-CoA-decarboxylase (each accessed on Sep. 12, 2024) Enzyme: 4.1.1.8.
EC numbers from the Expasy Enzyme database archived on Dec. 13, 2013 for the EC number 4.1.2 subclass.
EC numbers from the Expasy Enzyme database archived Nov. 5, 2014 or the EC number 4.1.1 subclass.
McDonald, A.G., "Fifty-five years of enzyme classification: advances and difficulties," The FEBS Journal, 281, pp. 583-592, 2014.

FIGURE 9

HACL1 ISOFORM 1 (Q9UJ83-1) SEQ ID NO. 1

MPDSNFAERS EEQVSGAKVI AQALKTQDVE YIFGIVGIPV TEIAIAAQQL GIKYIGMRNE QAACYAASAI GYLTSRPGVC
LVVSGPGLIH ALGGMANANM NCWPLLVIGG SSERNQEIMG AFQEFPQVEA CRLYTKFSAR PSSIEAIPFV EEKAVRSSIY
GRPGACYVDI PADFVNLQVN VNSIKYMERC MSPPISMAET SAVCTAASVI RNAKQPLLII GKGAAYAHAE ESIKELVEQY
KLPFLPTPMG KGVVPDNHPY CVGAARSRAL QPADVIVLFG ARLNWILHFG LPPRYQPDVK FIQVDICAEE LGNNVKPAVT
LLGNIHAVTK QLLEELDKTP WQYPPESKWW KTLREKMKSN EAASKELASK KSLPMNYYTV FYHVQEQLPR DCFVSEGAN
TMDIGRTVLQ NYLPRHRLDA GTFGTMGVGL GFAIAAAVVA KDRSPGQWII CVEGDSARGF SGMEVETICR YNLPILLVN
NNGIYQGFD TDTWKEMLKF QDATAVVPPM CLLPNSHYEQ VMTAFGGKGY FVQTPEELQK SLRQSLADTT KPSLINIMIE
PQATRKAQDF HWLTRSNM 578

HACL1 ISOFORM 2 (Q9UJ83-2) SEQ ID NO. 2

MPDSNFAERS EEQVSGAKVI AQALKTQDVE YIFGIVGIPV TEIAIAAQQL GIKYIGMRNE QAACYAASAI GYLTSRPLLV
IGGSSERNQE TMGAFQEFPQ VEACRLYTKF SARPSSIEAI PFVIEKAVRS SIYGRPGACY VDIPADFVNL QVNVNSIKYM
ERCMSPPISM AETSAVCTAA SVIRNAKQPL LIIGKGAAYA HAEESIKKLV EQYKLPFLPT PMGKGVVPDN HPYCVGAARS
RALQPADVIV LFGARLNWIL HFGLPPRYQP DVKFIQVDIC AEELGNNVKP AVTLLGNIHA VTKQLLEELD KTPWQYPPES
KWWKTLREKM KSNEAASKEL ASKKSLPMNY YTVFYHVQEQ LPRDCFVSE GANTMDIGRT VLQNYLPRHR LDAGTFGTMG
VGLGFAIAAA VVAKDRSPGQ WIICVEGDSA FGFSGMEVET ICRYNLPILL VVNNNGIYQ GFDTDTWKEM LKFQDATAVV
PPMCLLPNSH YEQVMTAFGG KGYFVQTPEE LQKSLRQSLA DTTKPSLINI MIEPQATRKA QDFHWLTRSN M 551

HACL1 ISOFORM 3 (Q9UJ83-3) SEQ ID NO. 3

MPDSNFAERS EEQVSGAKVI AQALKTQDVE YIFGIVGIPV TEIAIAAQQL GIKYIGMRNE QAACYAASAI GYLTSRPGVC
LVVSGPGLIH ALGGMANANM NCWYMERCMS PPISMAETSA VCTAASVIRN AKQPLLIIGK GAAYAHAEES IKKLVEQYKL
PFLPTPMGKG VVPDNHPYCV GAARSRALQF ADVIVLFGAR LNWILHFGLP PRYQPDVKFI QVDICAEELG NNVKPAVILL
GNIHAVTKQL LEELDKTPWQ YPPESKWWKT LREKMKSNEA ASKELASKKS LPMNYYTVFY HVQEQLPRDC FVVSEGANTM
DIGRTVLQNY LPRHRLDAGT FGTMGVGLGF AIAAAVVAKD RSPGQWIICV EGDSARGFSG MEVETICRYN LPILLVVNN
NGIYQGFDTD TWKEMLKFQD ATAVVPPMCL LPNSHYEQVM TAFGGKGYFV QTPEELQKSL RQSLADTTKP SLINIMIEPQ
ATRKAQDFHW LTRSNM 496

HACL1 ISOFORM 4 (Q9UJ83-4) SEQ ID NO. 4

MPDSNFAERS EEQVSGAKVI AQALKTQDVE YIFGIVGIPV TEIAIAAQQL GIK YIGMRNE QAACYAASAI GYLTSRPGVC
LVVSGPGLIH ALGGMANANM NCWPLLVIGG SSERNQETMG AFQEFPQAVR SSIYGRPGAC YVDIPADFVN LQVNVNSIKY

FIGURE 9 CONT

MERCMSPPIS MAETSAVCTA ASVIRNAKQP LLIIGKGAAY AHAEESIKKL VEQYKLPFLP TPMQKGVPD NHPYCVGAAR
SRALQFADVI VLFGARLNWI LHFGLPPRYQ PDVKFIQVDI CAEELGNNVK PAVILLGNIH AVTKQELASK KSLPMNYYTV
FYHVQEQLPR DCFVVSEGAN TMDIGRTVLQ NYLPRHRLDA GTFGTMGVGL GPAIAAAVVA KDRSPGQWII CVEGDSAFGF
SGMEVETICR YNLPHLLVV NNNGIYQGFD TDTWKEMLKF QDATAVVPPM CLLPNSHYEQ VMTAFGGKGY FVQTPEELQK
SLRQSLADTT KPSLINIMIE PQATRKAQDF HWLTRSNM 518

BIOSYNTHESIS OF PRODUCTS FROM 1-CARBON COMPOUNDS

PRIOR RELATED APPLICATIONS

This application is a continuation of U.S. application Ser. No. 15/523,284, filed Apr. 28, 2017, which is a U.S. National Stage entry of International Application No. PCT/US15/58121, which designated the United States and was filed on Oct. 29, 2015, published in English, which claims the benefit of U.S. Provisional Application No. 62/069,850, titled SYNTHETIC PATHWAY FOR BIOSYNTHESIS FROM 1-CARBON COMPOUNDS, filed on Oct. 29, 2014. The entire teachings of the above applications are incorporated herein by reference.

FEDERALLY SPONSORED RESEARCH STATEMENT

Not Applicable.

FIELD OF THE DISCLOSURE

The invention relates to engineered microorganisms that can make various chemicals for industrial use. In particular, the biological production of multi-carbon compounds directly from single carbon compounds without the need for central metabolism.

BACKGROUND OF THE DISCLOSURE

In the past, much our energy and chemicals have derived from fossilized carbon resources, such as petroleum and coal. However, concerns about climate change, political instability, and depletion and cost of petroleum resources have recently ignited interest in the establishment of a bio-based industry and a number of strategies are being pursued to achieve the sustainable production of fuels and chemicals. One of the most promising approaches is the use of microorganisms to convert biomass into the desired product. The use of these feedstocks, however, is hindered by the difficulty of accessing the resource, their high price, and limited availability. One-carbon compounds, including $CO_2$, CO, formate, methanol, and methane have recently emerged as alternative renewable feedstocks. Conversion of these substrates to fuels and chemicals not only offers an attractive alternative in terms of process economics but also will further contribute to reduce the levels of greenhouse gases like $CO_2$ and methane.

Microbial catalysts have been designed and engineered to synthesize products of interest using feedstocks as diverse as sugars, glycerol, carbon dioxide, carbon monoxide, formate, methanol, and methane. For the case of 1-carbon feedstocks, such conversions are made possible by a general network of metabolic pathways that are organized as shown in FIG. 1 and include specialized pathways for carbon fixation, central metabolism, and product synthesis. This type of metabolic architecture has been exploited in all metabolic engineering efforts conducted to date to develop microbes for industrial applications.

This disclosure describes an alternative platform for the bioconversion of 1-carbon substrates, which consists of a single engineered metabolic pathway that allows for the direct synthesis of chemical products from one-carbon compounds using a 'bottom up' integrated design. The engineered pathway defines a new metabolic architecture that consolidates carbon fixation, central metabolism, and product synthesis into single pathway (FIG. 2). The pathway uses single carbon extension units, which bypasses the need for the production of common metabolic intermediates and allows for elongation of a carbon backbone iteratively in single carbon increments.

This is in contrast to current approaches, which require first the fixation of single carbon compounds to metabolic intermediates before elongation (FIG. 1) and which commonly elongate a carbon backbone by two or more carbons at a time. This synthetic platform was engineered from the 'bottom-up' and provides potential advantages over current 'top-down' methods, which suffer from difficulty of engineering and inefficiencies arising from the use of assimilating pathways to first produce metabolic intermediates before carbon chain elongation and product formation.

SUMMARY OF THE DISCLOSURE

Engineering biology from the 'bottom-up' has gained momentum recently. In particular, the field of synthetic biology has had particular focus on using this 'bottom-up' approach, with the end goal of designing systems with tunable control and well-defined response. Synthetically developed pathways can have advantages over natural pathways, for example by allowing for exogenous control over pathway enzyme expression. This potentially decouples the pathway performance with the organism's complex and poorly understood regulatory mechanisms. Further decoupling can be achieved by synthetic pathways when designed to avoid the usage of central metabolic pathways, such as those generating acetyl-CoA, allowing the pathway performance to be independent of the organism's central metabolism, which is also subject to regulation and interaction with other pathways. A bottom up design approach can thus allow for the creation of a pathway that is independent from the host system. Here, the bottom up design of a pathway capable of the conversion of C1 molecules to longer chain products is described.

The development of a synthetic pathway that consolidates fixation of single carbon compounds into the synthesis of products is described. The pathway allows for direct synthesis of products from single carbon compounds, avoiding the need to produce the cells typical intermediates and use of central metabolic pathways, as required by the existing approach. This synthetic pathway is inspired on the catabolic α-oxidation pathway (one carbon shortening of fatty acids) and based on the key recent finding in our laboratory that the enzyme hydroxyl-acyl-CoA lyase (HACL, part of the α-oxidation pathway) is reversible and able to catalyze C—C bond formation between formyl-CoA and an aldehyde. This mechanism for C—C bond formation had not been previously reported in the literature and allows for carbon-chain elongation by one-carbon units.

The pathway accomplishes four main functions:

First: single carbon compounds are converted to an active 'extender' form that can be incorporated into a carbon skeleton. This is done by enzymatically converting a one-carbon unit into an activated CoA derivative, and there are a variety of enzymes available to do this.

Second: the pathway allows for these single carbon extenders to iteratively elongate the carbon skeleton to desired length. An enzyme from the alpha oxidation pathway (hydroxyl-acyl-CoA lyases or HACLs) is used to catalyze the key condensation/C—C bond formation reaction, being driven herein to run in the reverse direction. A series of dehydration and reduction reactions then converts the molecule to a form suitable for successive rounds of elongation.

Third: In addition, if the initial priming aldehyde has more than one carbon, a regeneration pathway to regenerate the starting aldehyde molecule is needed. However, if the starting aldehyde is formaldehyde or a single turn of the cycle is sufficient, then this functionality can be omitted.

Fourth: there is a method from which the desired products are synthesized from the elongated carbon skeleton. A large variety of termination enzymes can pull intermediates out of the cycle and if desired those can be further modified enzymatically.

The pathway described herein drew inspiration from the catabolic α-oxidation pathway (one carbon shortening of fatty acids) and is based on the key recent finding in our laboratory that the enzyme 2-hydroxyl-acyl-CoA lyase (HACL, part of the α-oxidation pathway) is reversible and able to catalyze C—C bond formation between formyl-CoA and an aldehyde.

The synthetic pathway disclosed in this invention serves as a platform for the generation of valuable chemical products from less valuable and more abundant single carbon compounds, rather than from readily depleting fossil sources, such as petroleum. Methane, for example, can be converted into liquid "drop in" fuels for use in the current transportation infrastructure. Carbon dioxide can be sequestered and converted into useful products. The methods, materials and systems herein thus allow for single carbon molecules of varying reduction levels, from methane to carbon dioxide, to be assimilated directly into an elongating carbon backbone.

In the synthetic pathway herein disclosed, single carbon molecules are first activated to formyl-CoA, which can be directly ligated with an aldehyde by the enzyme 2-hydroxyacyl-CoA lyase. The resulting 2-hydroxyacyl CoA is one carbon longer than the originating aldehyde and undergoes a series of reactions to return it to an aldehyde, allowing for the further elongation of the carbon backbone. Intermediates of the above reactions can be diverted from the cycle with a termination enzyme to generate valuable chemical products, such as (but not limited) to carboxylic acids, alcohols, or alkanes of varying chain lengths and functionalities.

The process involves performing traditional cultures using industrial organisms (such as *E. coli* or *S. cerevisiae* or *Methylococcus capsulatus* or *Pichia pastoris*) that convert single carbon compounds, such as methane, methanol, formaldehyde, formate, carbon monoxide, or carbon dioxide, into chemical products. These organisms are considered workhorses of modern biotechnology, and are easy to genetically engineer, and scale up for industrial production levels.

In another embodiment, however, one could provide any intermediate in the designed synthetic pathway as a starting compound, and need not make the entire molecule from scratch, extending the starting molecule once converted to aldehyde by one carbon, and pulling out any intermediate in the cycle using the termination module. Such embodiments may be useful where an intermediate is plentiful or a waste product from another process, and thus very inexpensive. Combined therewith, the regeneration module can be omitted, if the starting aldehyde is formaldehyde or a single turn of the cycle is sufficient.

It is also possible to use only a portion of the designed synthetic pathway, again if suitable given the starting molecule and final desired product. Thus, if just adding a single carbon will suffice, it may be possible to use just the HACL protein, as described herein. As yet another alternative, one or more downstream enzymes in the designed synthetic pathway are used in combination with the HACL. However, in most instances the most versatility comes from including all 4 modules.

The modules in a living system are generally made by transforming the microbe with an expression vector encoding one or more of the proteins, but the genes can also be added to the chromosome by recombineering, homologous recombination, and similar techniques. Where the needed protein is endogenous, as is the case in some instances, it may suffice as is, but is usually overexpressed for better functionality and control over the level of active enzyme.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

As used herein, the expressions "microorganism," "microbe," "strain" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples proteins of similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized"

for expression in *E. coli*, yeast, algal or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Recombinant methods were invented in the 1970's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at http://en.wikipedia.org/wiki/List_of_sequenced_bacterial_genomes.

Additionally, yeast are a common species used for microbial manufacturing, and many species can be successfully transformed. In fact, the alpha oxidation pathway is present in yeast and the alpha-oxidation enzyme hydroxyl-acyl-CoA lyases (HACL), which is a key part of this invention was successfully expressed in yeast *Saccharomyces*. Other species include but are not limited to *Candida, Aspergillus, Arxula adeninivorans, Candida boidinii, Hansenula polymorpha* (*Pichia angusta*), *Kluyveromyces lactis, Pichia pastoris*, and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia, Haematococcus, Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for stability reasons.

Still further improvements in yield can be had by reducing competing pathways, such as those pathways for making e.g., acetate, formate, ethanol, and lactate, and it is already well known in the art how to reduce or knockout these pathways. See e.g., the William Marsh Rice University patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova TA & Madden TL (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genetics of an organism was intentionally manipulated in some way.

"Reduced activity" or "inactivation" or "underexpressed" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like.

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any expression in a species that lacks the activity altogether. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity and ease of exerting externals controls, although permanent modifications to the genome may be preferred in the long term for stability reasons.

BRIEF DESCRIPTION OF FIGURES

FIG. 9. Four isoforms of human HACL1 (SEQ ID NOs 1-4).

FIG. 18 and FIG. 19 prove that the enzyme can run in reverse, as required for the anabolic pathway.

FIG. 19. HPLC chromatogram of HACL1 synthetic reaction samples incubated with acetaldehyde and formyl-CoA. Solid line: HACL1 sample; Dashed line: no enzyme control. The expected product of the ligation of acetaldehyde and formyl-CoA is lactoyl-CoA, which would be expected to be hydrolyzed to its acid form, lactate. A peak for lactate (26 min) was observed in samples containing purified HACL1 and was not observed in samples that did not contain enzyme.

Table 1A-D. Enzyme list for each of the four modules. These are only a few of the enzymes that can be used, but provides a representative listing.

DETAILED DESCRIPTION OF THE DISCLOSURE

Figure 7:
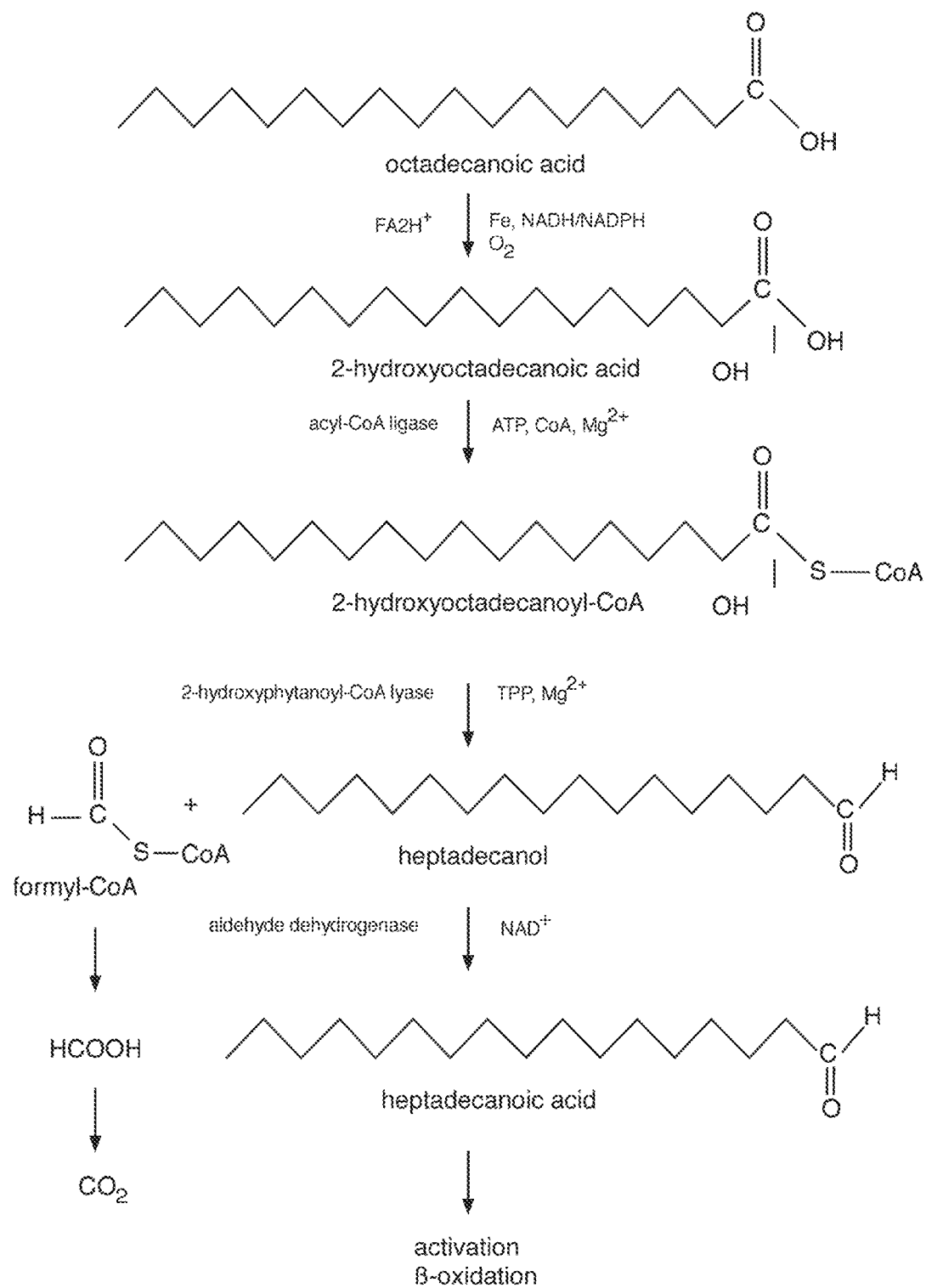
FIG. 7. Alpha Oxidation of straight chain fatty acids.
Figure 8:
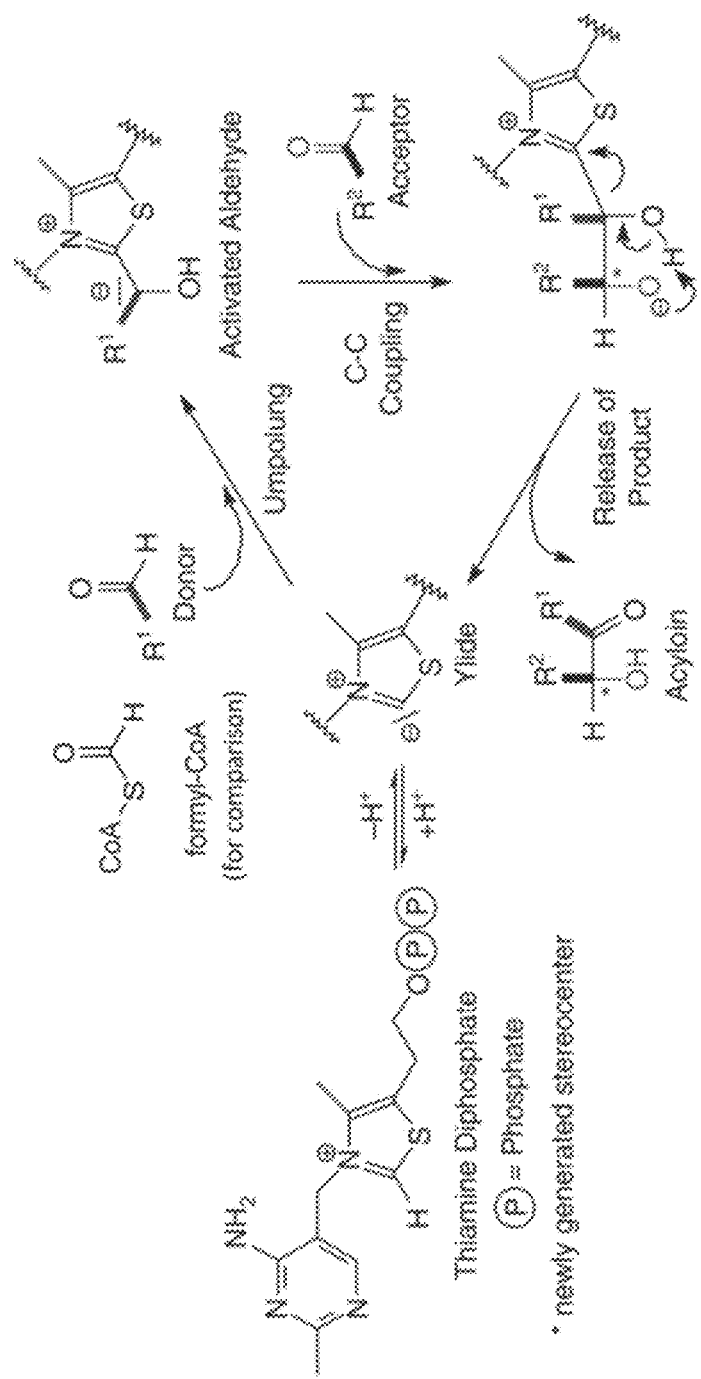
FIG. 8. Mechanism of the acyloin condensation reaction by TPP dependent enzymes. Formyl-CoA is included, for comparison, as the donor molecule such that $R^1$ is the S-CoA group. The acceptor molecule is any aldehyde. The ligation of these two molecules by this mechanism results in the formation of a 2-hydroxyacyl-CoA.

Herein, our focus will be a mammalian version of the alpha oxidation pathway known to operate on straight chain fatty acids. See FIG. 7. In this pathway, fatty acids are first hydroxylated at the α position, and the resulting 2-hydroxy fatty acid is activated to the acyl-CoA derivative. The key enzyme 2-hydroxyacyl-CoA lyase ("HACL") cleaves the 2-hydroxyacyl-CoA into formyl-CoA and an aldehyde one carbon shorter than the starting fatty acid. This forms the foundation of the second part of the hypothesis—that HACL can catalyze the reverse reaction, elongating a fatty aldehyde by one carbon using formyl-CoA as an extender.

Figure 1:
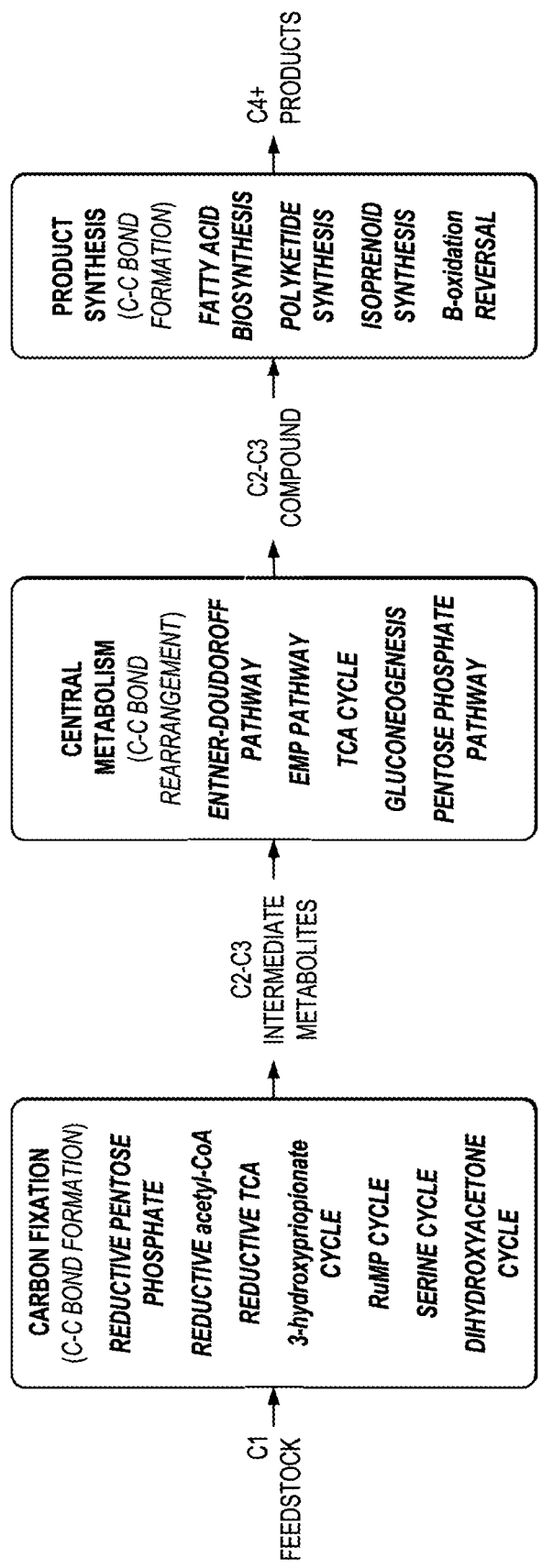
FIG. 1. Current 'top-down' metabolic engineering approach based on editing existing architecture of natural metabolism.
Figure 2:
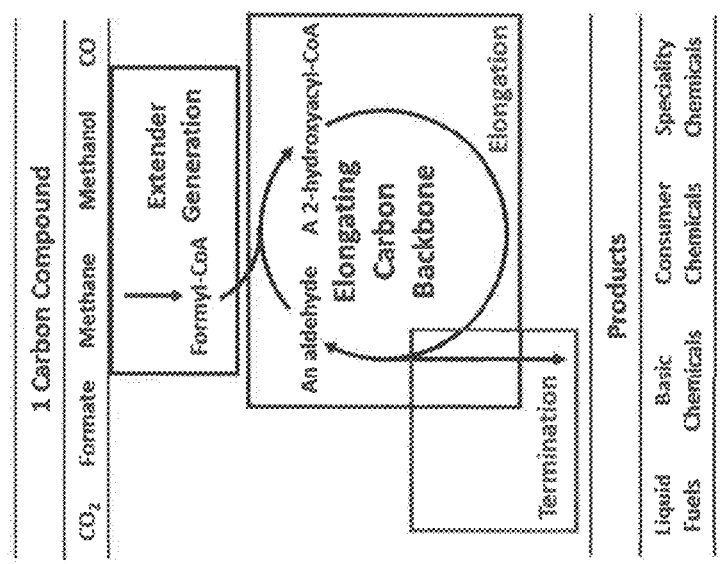
FIG. 2. Overall structure of the designed pathway. "Bottom up" integrated design with a new metabolic architecture. Consolidation of C fixation, central metabolism, and product synthesis (shown in FIG. 1) into a single pathway that enables direct use of single carbon molecules for the synthesis of longer-chain (≥C2) products. See also FIG. 10 for more detail.

Just as the thiolase reaction in the β-oxidation pathway was shown to be reversible (see e.g., US20130316413, US20140273110, incorporated by reference herein in its entirety for all purposes), it was anticipated that the HACL reaction of α-oxidation could be reversed. Thermodynamically and mechanistically, the hypothesis seemed plausible. Our preliminary experiments were expected to confirm this, based on the Gibbs free energy of the reaction, and our subsequent results show that we were correct. The overall design of the new synthetic anabolic pathway is shown in FIG. 2 and additional detail is in FIG. 10.

Figure 15A:
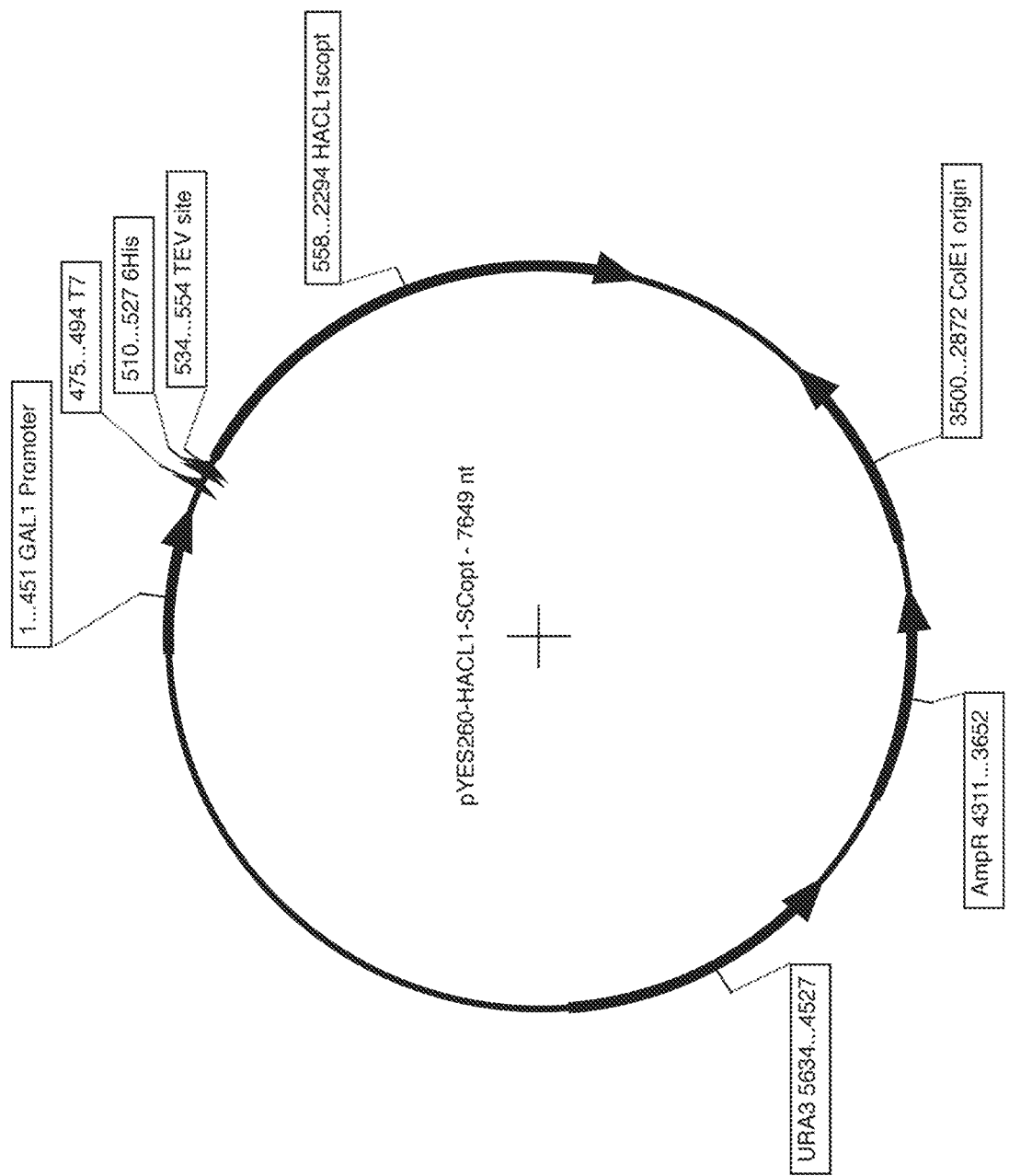
FIG. 15A-B. Expression vector constructs for *S. cerevisiae* (15A) and *E. coli* (15B) expression vector constructs containing the gene encoding an amino-terminal 6×HIS-tagged hydroxyl-acyl-CoA lyase HACL1 from *Homo sapiens*.
Figure 15B:
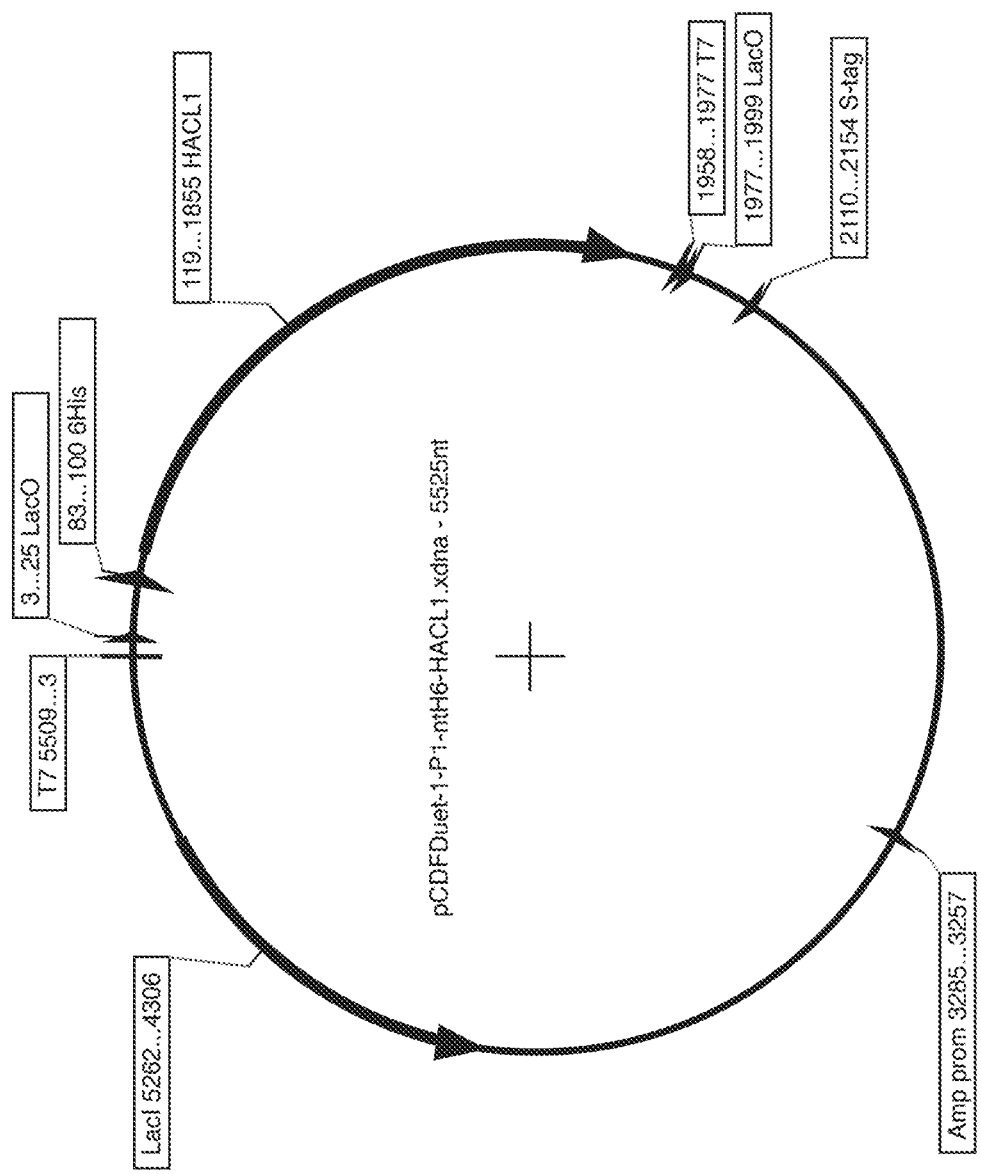

The gene encoding a 2-hydroxyacyl-CoA lyase from *Homo sapiens*, HACL1 (FIG. 9), was cloned into *E. coli*. Cloning of *Homo sapiens* HACL1 into a yeast expression vector, pYES2, has also been completed (see FIG. 15A-B), and expression experiments in yeast have been performed. Using an overexpressed HACL enzyme, we were able to drive the reaction in reverse (see EQ 1), thus providing an elongation module for use. See FIG. 18/19.

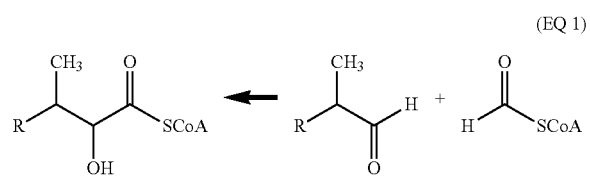

(EQ 1)

Although we used the human HACL gene herein (see UniProt Q9UJ83), that was for convenience, and any mammalian HACL gene could be used, provided it catalyzes the same reaction. The HACL gene is EC number 4.1 (incompletely characterized to date), and other proteins that could suffice include gorilla (XP_004033733.1=577/578 (99% identity); chimp (NP_001267049.1=574/578 (99%)); yak (XP_005910609.1=515/581 (89%)); dog (XP_013961990.1=514/581 (88%)); cat (XP_003992184.1=520/581 (90%), mouse (NP_064359.2=508/581 (87%), and the like. In addition, non-mammalian species may also suffice, as homologs are known to exist in the frog (GenBank NP_001017332) and zebrafish (GenBank NP_998250). Recombinant protein is even commercially available from *Arabidopsis* (MyBioSource).

The HACL reaction will of course normally run in the physiologically forward direction, making 2-hydroxyacyl-CoA molecules shorter by one carbon (the catabolic direction). However, it can be forced to run in the reverse elongation direction (see EQ 1) by overexpressing it at sufficient levels, and by increasing substrate levels or by removing products, thus pushing the reaction in the opposite direction. We were able to make it run in the reverse anabolic or extension direction by providing extra substrate. Additionally, the temperature of the reaction was lowered from 37° C. to room temperature and the pH of the reaction was lowered from 7.4 to 5.4.

In total, four modules comprise the proposed invention, and these are generally described in turn.

Figure 3:
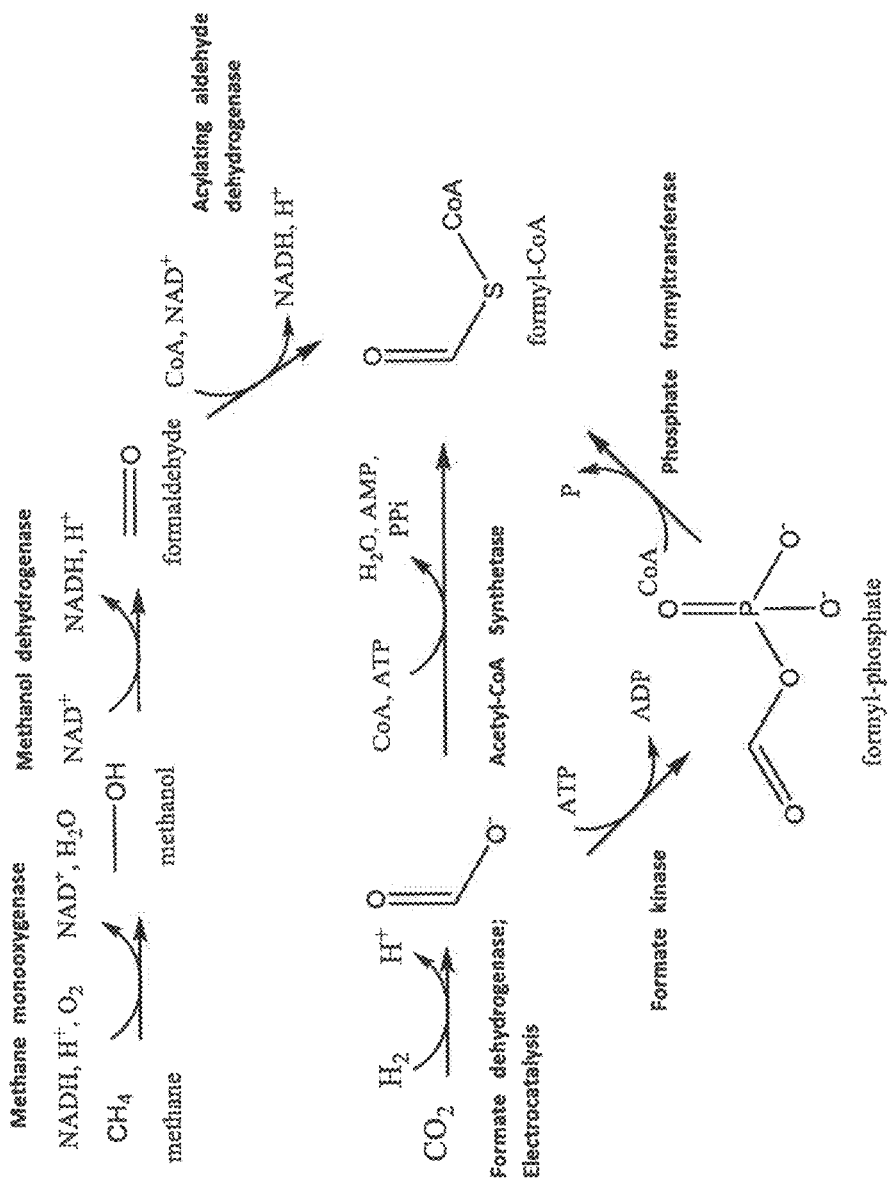
FIG. 3. Extender Generation Module for converting a one carbon compound to an activated form that can be used for elongation. Refer to Table 1A for more detail.

Extender generation module: The extender generation module, illustrated in FIG. 3 and summarized in Table 1A, is intended to activate a single carbon molecule into the form in which it can be used for ligation. In the proposed scheme using 2-hydroxyacyl-CoA lyase ("HACL") as the extender enzyme, this activated form is the molecule formyl-CoA. Methods for the conversion of formate to formyl-CoA will be described in detail here.

Formate serves as a good starting point for single carbon utilization because it can be reduced from $CO_2$, enzymatically or electrocatalytically, and oxidized from more reduced molecules such as methane, methanol, or formaldehyde. There are at least 3 potential routes for formate activation to formyl-CoA:

1) The first route uses one enzyme, an acyl-CoA synthase (ACS), to directly produce the thioester. In the process, this hydrolyzes one ATP to AMP, effectively consuming two ATP equivalents. One such AMP forming acyl-CoA synthase with activity on formate has been found in the organism *Pyrobaculum aerophilum*. The ACS, encoded by the open reading frame (ORF) PAE2867, showed an unusually broad range of substrate specificity from formate to butyrate.

2) The alternative route uses two enzymes, but produces ADP, utilizing one ATP equivalent. The enzymes capable of catalyzing these reactions were first identified in *Clostridium cylindrosporum*. This organism contains two formate kinases, which catalyze the formation of formyl-phosphate from formate and ATP, and a phosphate formyltransferase, which is capable of synthesizing formyl-CoA from formyl-phosphate. Since then, other enzymes have been discovered with activity on formate, such as acetate kinase from *Salmonella typhimurium*. These enzymes warrant investigation for the generation of formyl-CoA.

3) An additional alternative allows for the direct conversion of formaldehyde to formyl-CoA using the acylating aldehyde dehydrogenase enzyme. Variants of this enzyme have been discovered in species such as Giardia intestinalis, *Pseudomonas* sp. CF600, and *Acinetobacter* sp. HBS-2 with experimental evidence of activity on formaldehyde. These enzymes catalyze the conversion of formaldehyde to formyl- CoA with the generation of one molecule of NADH. Much like the methylotrophic pathways of single carbon metabolism, this enzyme allows for the more efficient utilization of single carbon molecules at the same oxidation state or more reduced than formaldehyde, including methanol and methane.

Figure 4A:
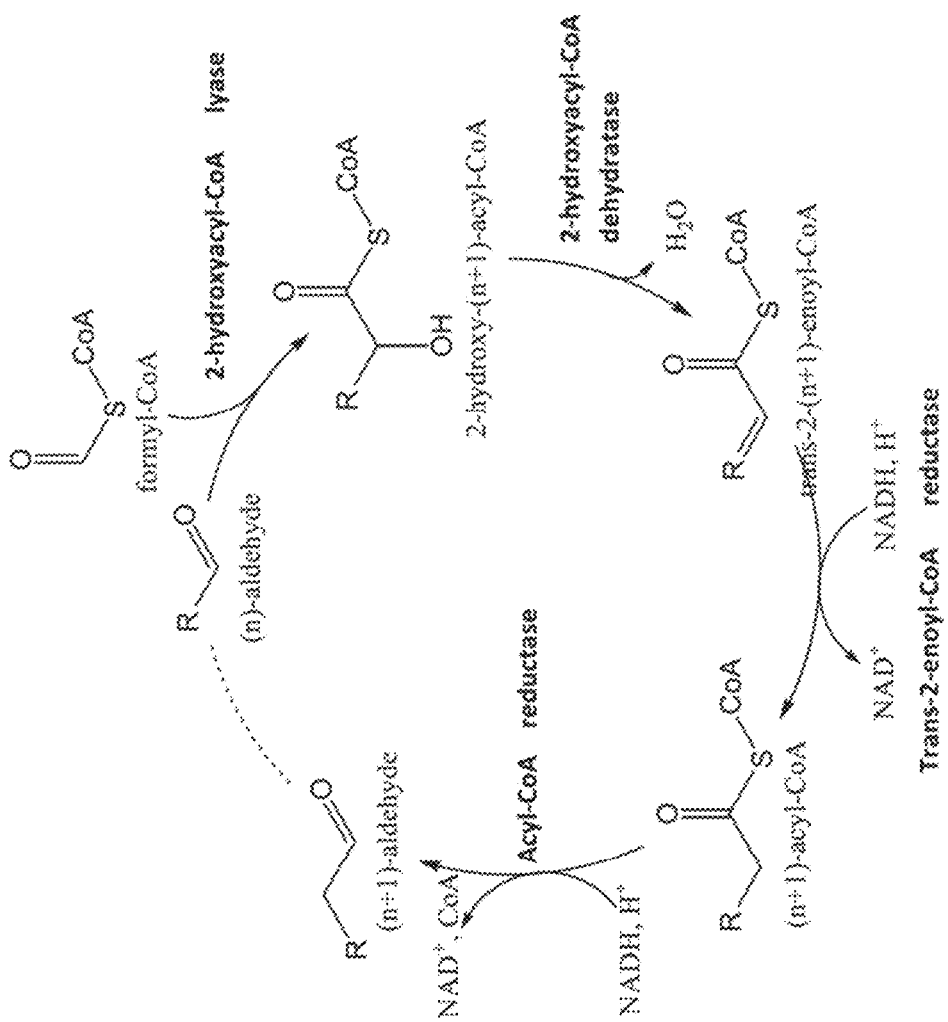
FIG. 4A-B. Possible Elongation Modules for elongating a carbon backbone by one carbon per iteration. Refer to Table 1B for more detail.
Figure 4B:
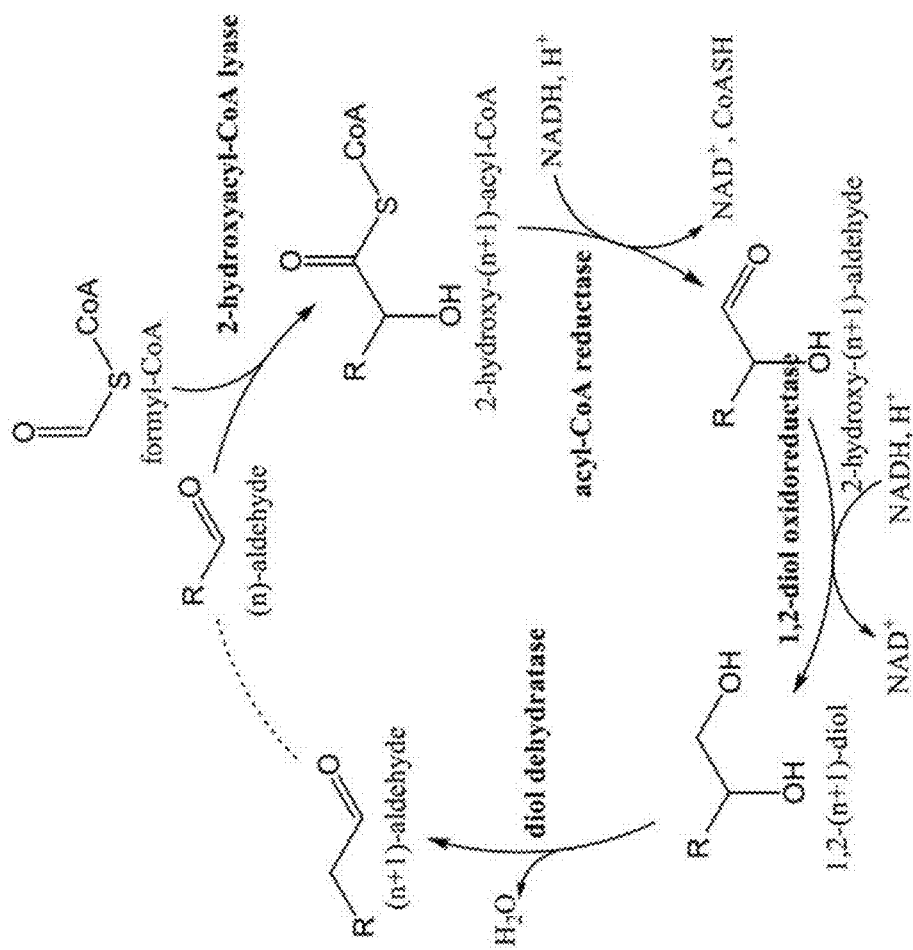

Elongation module: The elongation module, shown in FIG. 4A-B and summarized in Table 1B, allows for the iterative elongation of the carbon backbone. Using HACL, an exemplary one-carbon carbon-carbon bond-forming enzyme, an aldehyde is ligated with formyl-CoA to produce a 2-hydroxyacyl-CoA that is one carbon longer than the originating aldehyde.

To allow for additional rounds of elongation, the 2-hydroxyacyl-CoA must be converted back to the aldehyde form. In one implementation FIG. 4A, from the 2-hydroxyacyl-CoA, the next step is dehydration of the molecule to the trans-2-enoyl-CoA. An enzyme with this activity, lactyl-CoA dehydratase, has been discovered in *Clostridium propionicum* encoded by gene lcdABC. This enzyme was found to catalyze the conversion of 2-hydroxy substrates such as 2-hydroxypropionyl-CoA, also known as lactyl-CoA, and 2-hydroxybutyryl-CoA to prop-2-enoyl-CoA (acryloyl-CoA) and but-2-enoyl-CoA (crotonyl-CoA), respectively.

In the next step, the resulting trans-enoyl-CoA is converted to a saturated acyl-CoA. A number of enzymes have been identified with this desired activity. To follow the previous example, acryloyl-CoA has been shown to be reduced to propionyl-CoA by an acryloyl-CoA reductase encoded by *Rhodobacter sphaeroides* acuI.

Other trans-2-enoyl-CoA reductases with broad chain specificity have been used in engineered pathways such as the reverse β-oxidation pathway, which, similar to this pathway, dehydrates a 3-hydroxyacyl-CoA to a trans-2-enoyl-CoA before reducing it to the saturated acyl-CoA. In this application, the trans-2-enoyl-CoA reductase from *Euglena gracilis* has already been successfully used. Increasing evidence also indicates that the native *E. coli* gene fabI, which encodes an enoyl-ACP reductase used in the fatty acid biosynthesis pathway, also has activity on enoyl-CoA substrates (Vick et al., 2014).

From the acyl-CoA, the aldehyde can be directly generated. *Salmonella enterica* eutE encodes an acyl-CoA reductase that is capable of catalyzing the conversion of propionyl-CoA to propanal. (Zhu, et al., 2011) Similarly, the acyl-CoA reductase from *Clostridium beijerinckii* gene ald has been shown to have activity on butyryl-CoA in its conversion to butanal. This step completes the cycle, allowing the carbon chain to undergo another round of elongation.

In an alternative implementation of the elongation module, 2-hydroxyacyl-CoA can be converted to its corresponding aldehyde via an alternative arrangement of reductions and dehydrations to those described above (FIG. 4B). Lyase is first reduced to a 2-hydroxyaldehyde by an acyl-CoA reductase, examples of which are provided above. The 2-hydroxyaldehyde is then reduced further to a 1,2-diol by a 1,2-diol oxidoreductase. *E. coli* fucO has been shown to encode one such 1,2-diol oxidoreductase. Finally, the 1,2-diol can be converted to the aldehyde by a diol dehydratase. *Klebsiella ocytoca* pddABC has been shown to encode an enzyme capable of performing the dehydration of C2-C4 1,2-diols to their corresponding aldehydes. This aldehyde can be used for further elongation of the carbon backbone.

Figure 5:
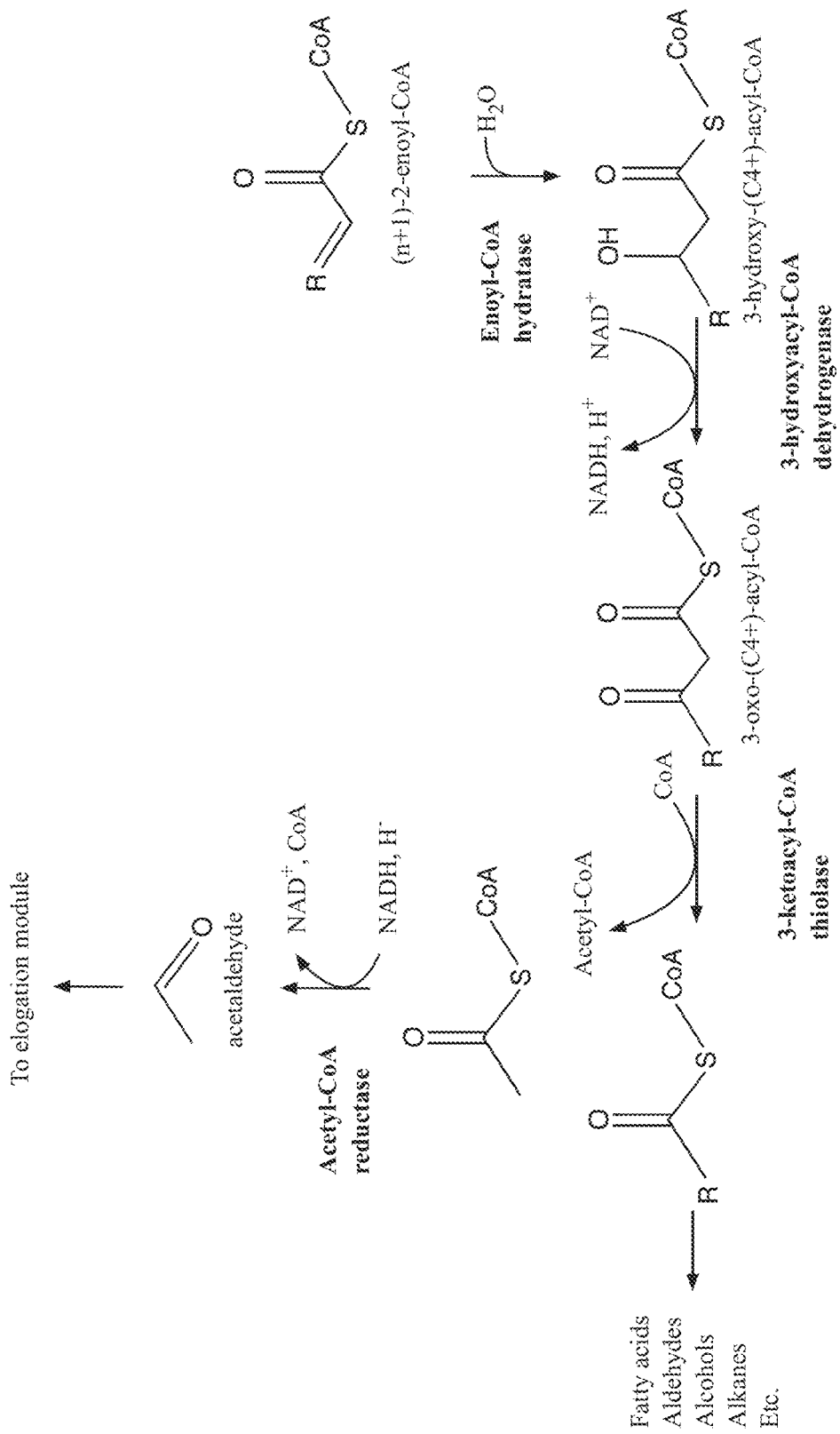
FIG. 5. Some implementations include a Regeneration Module for allowing for the regeneration of an aldehyde to prime further elongation, thus allowing multiple cycles of the synthetic pathway and more than one carbon to be added to a growing chain. Refer to Table 1C for more detail.

Regeneration module: A pathway that allows for the regeneration of a priming aldehyde is described herein and illustrated in FIG. 5. This would allow for the generation of products without necessitating the diversion of cellular resources to produce a starting aldehyde.

Starting from the trans-2-enoyl-CoA, an enoyl-CoA hydratase, such as native *E. coli* FadB, catalyzed the conversion to a 3-hydroxyacyl-CoA. FadB has also been shown to have 3-hydroxyacyl-CoA dehydrogenase activity, which catalyzes the conversion of the 3-hydroxyacyl-CoA to a 3-ketoacyl-CoA. A thiolase, such as the *E. coli* enzymes FadA or AtoB, can then cleave an acetyl-CoA from the 3-ketoacyl-CoA, leaving an acyl-CoA. The acetyl-CoA can be reduced, for example by the aforementioned *Salmonella enterica* EutE, to acetaldehyde and used to prime a further elongation cycles, while the acyl-CoA can be converted to products.

Termination module: From the intermediates of the above reactions, there are a number of possible ways by which products can be generated by pulling intermediates out of the pathway with one or more enzyme reactions. Termination pathways are highly inspired by our work on the reverse beta oxidation, which has provided a great number of termination enzymes and pathways that can be employed herein. Thus, the reader is referred to US20130316413, US20140273110, et seq, and the associated publications for additional termination enzymes, including the selection thereof to control chain length, and at which point in the cycle an intermediate is removed.

Figure 6:
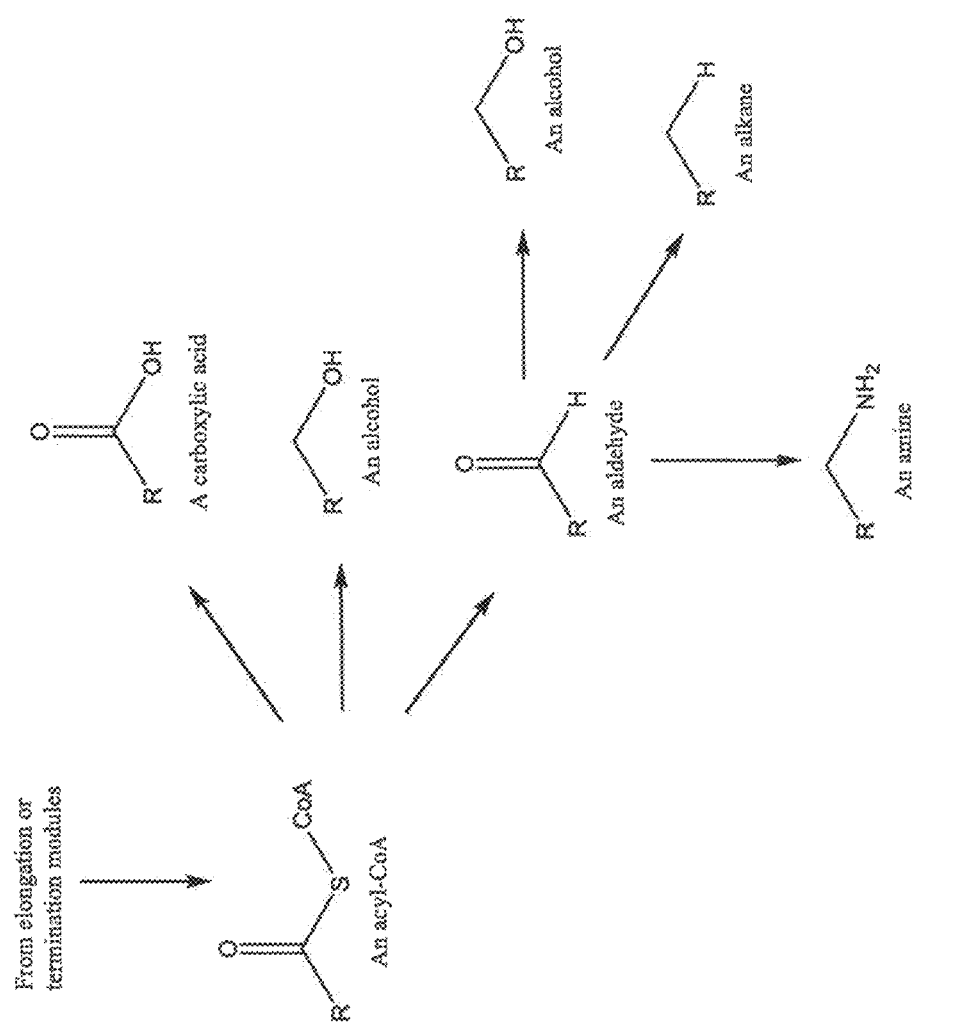
FIG. 6. Termination module: Potential products derived from acyl-CoA intermediates of the pathway modules. Refer to Table 1D for more detail.

Resulting acyl-CoAs from the pathway can be converted to products such as fatty acids by expression of a thioesterase, alcohols by expression of an acyl-CoA reductase and an aldehyde reductase, or alkanes by expression of an acyl-CoA reductase and aldehyde decarbonylase. See FIG. 6.

Figure 10A:
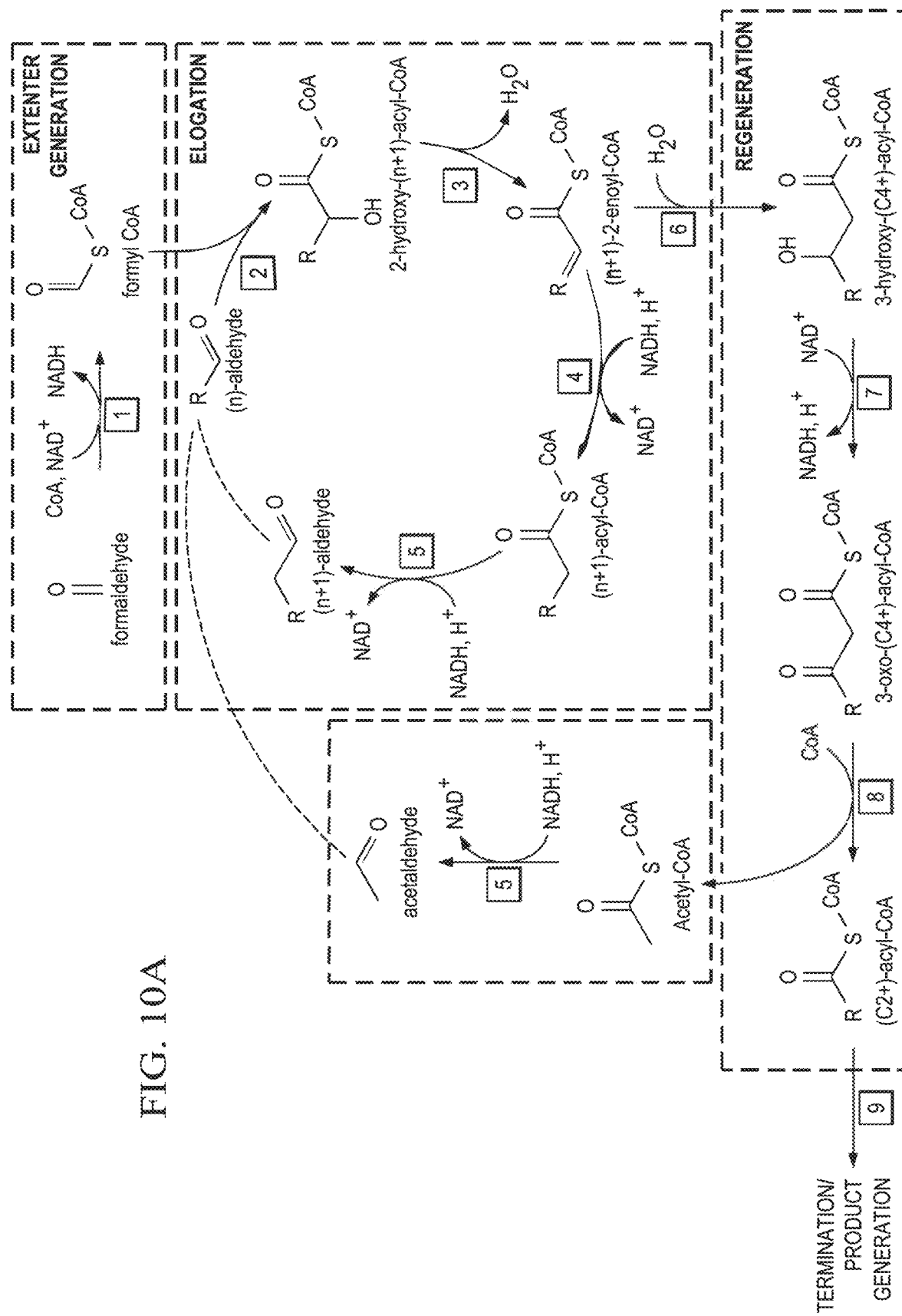
FIG. 10A-B. Overview of some proposed implementations of the pathway. Numbers correspond to the reactions listed in Table 2.
Figure 10B:
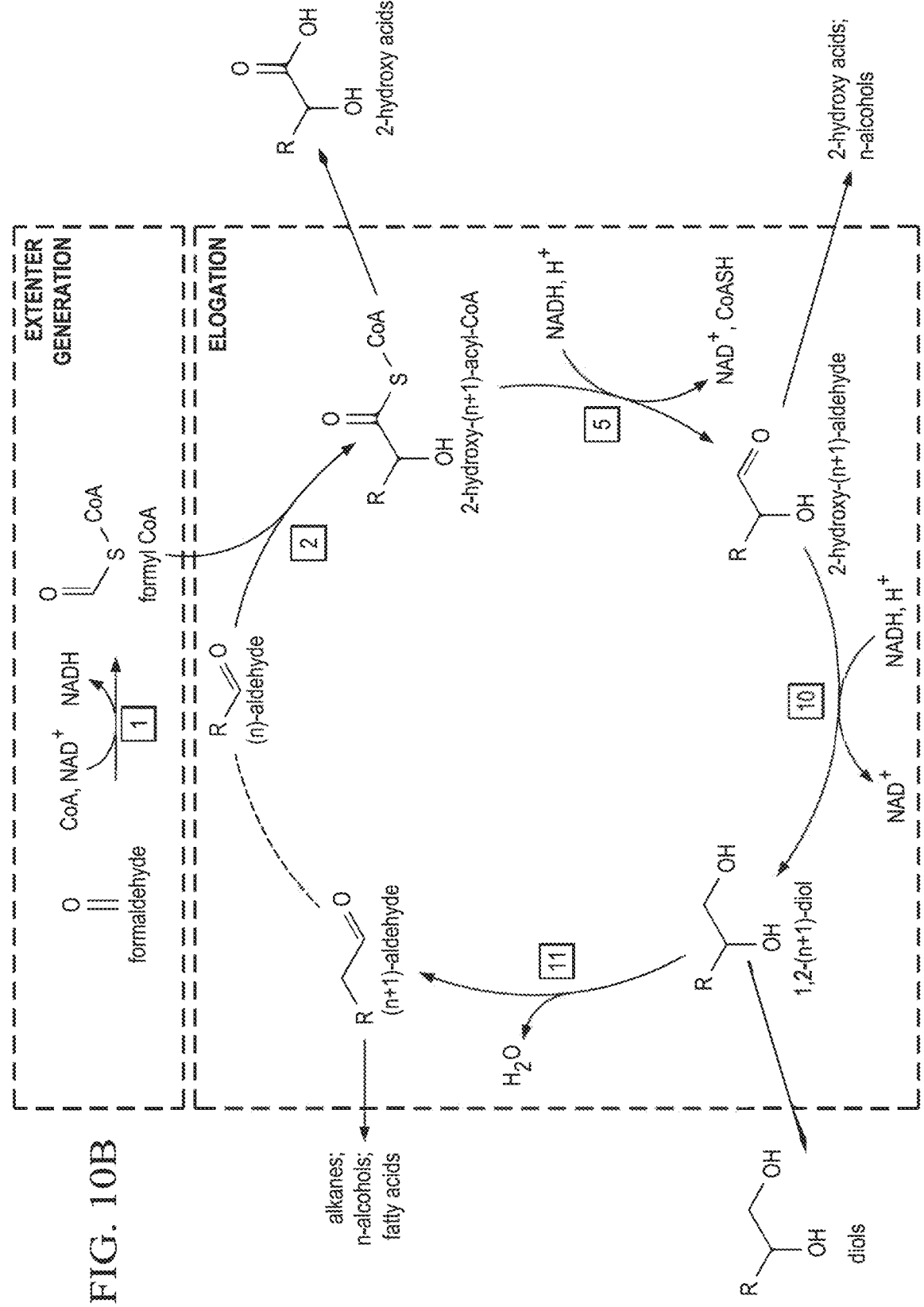
Figure 11:
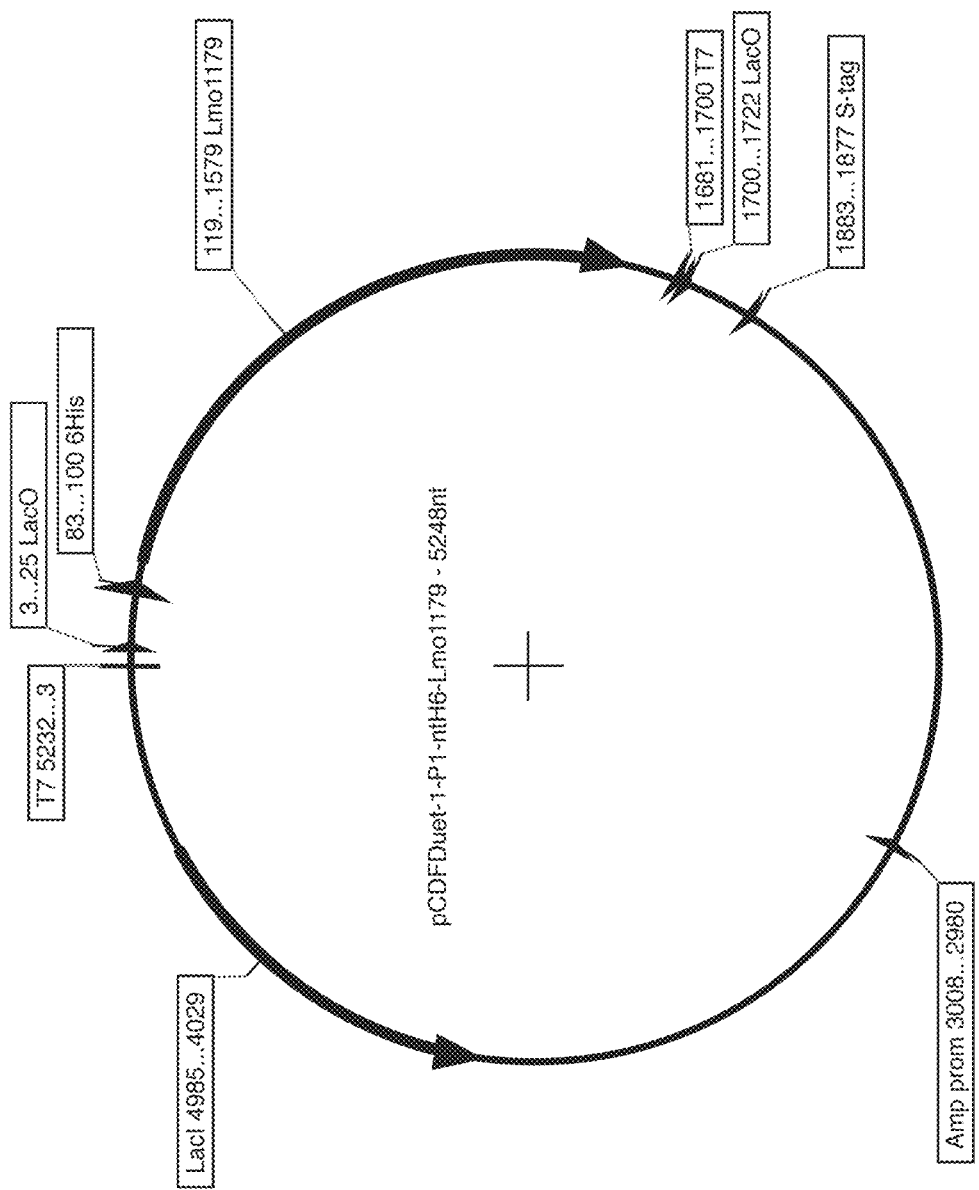
FIG. 11. Vector construct containing the gene encoding N-terminal HIS-tagged acylating aldehyde reductase Lmo1179 from *Lysteria monocytogenes* for expression in *E. coli*.

Tables 1A-D present a summary of the enzymes corresponding to the proposed pathway design and FIG. 10A-B provide a representation of the overall pathway in the forms proposed above. As written, starting from formate, the pathway uses one ATP equivalent for every one carbon elongation or, for ease of comparison to alternatives, two ATP equivalents for two carbon elongation.

It is important to note, though, that starting from formaldehyde, which can be readily oxidized from more reduced compounds, the pathway requires no ATP equivalents for elongation. This ATP efficiency is comparable to even the more efficient alternatives, for example the combination of the reductive acetyl-CoA or Ribulose Monophosphate Pathway (RuMP) pathways with the reverse β-oxidation pathway, which consume approximately one ATP equivalent from $CO_2$ or no ATP from formaldehyde, respectively, for two carbon elongation.

Following the construction of a suitable strain containing the engineered pathway, culturing of the developed strains can be performed to evaluate the effectiveness of the pathway at its intended goal, the production of products from single carbon compounds. The organism can be evaluated for growth on a variety of single carbon substrates, from methane to $CO_2$ and $H_2$, either autotrophically or mixotrophically, with the inclusion of an additional carbon source. The products produced by the organism can be measured by HPLC or GC, and indicators of performance such as growth rate, productivity, titer, yield, or carbon efficiency can be determined.

Further, evaluation of the interaction of the heterologously expressed pathway enzymes with each other and with the host system can allow for the optimization of pathway performance and minimization deleterious effects. Because the pathway is under synthetic control, rather than under the organism's natively evolved regulatory mechanisms, the expression of the pathway must be manually tuned to avoid potential issues that slow cell growth or production and to optimize production of desired compounds.

Additionally, an imbalance in relative enzyme activities might restrict overall carbon flux throughout the pathway, leading to suboptimal production rates and the buildup of pathway intermediates, which can inhibit pathway enzymes or be cytotoxic. Analysis of the cell cultures by HPLC or GC can reveal the metabolic intermediates produced by the constructed strains. This information can point to potential pathway issues.

As an alternative to the in vivo expression of the pathway, a cell free, in vitro, version of the pathway can be constructed. By purifying the relevant enzyme for each reaction step, the overall pathway can be assembled by combining the necessary enzymes. With the addition of the relevant cofactors and single carbon compounds, the pathway can be assessed for its performance independently of a host. As yet another alternative, whole wet or dried cells can be used as bioreactors. However, a living, growing culture system is preferred.

The primary focus of the proposed work was the development of a pathway for the direct synthesis of products from single carbon compounds. An additional area of interest, however, involves the use of the enzymes related to α-oxidation for the production of α-functionalized products. In particular, fatty acid 2-hydroxylases allow for the production of α-hydroxy acids from fatty acids, which can be further converted to α-hydroxy aldehydes, alcohols, ketones, or esters, or further into α-keto compounds. Such α-functionalized products have been found to be particularly useful bioactive molecules and have found applications in cosmetics as well as for drug delivery. The enzymes required for these transformations can be expressed in E. coli, yeast or algae and tested in vitro, as described above. When used in conjunction with a product-synthesizing platform, such as the β-oxidation reversal pathway, the microbial production of α-functionalized products can be achieved.

The following description of experiments provides additional details, any one of which can be subject to patenting in combination with any other. The specification in its entirety is to be treated as providing a variety of details that can be used interchangeably with other details, as it would be of inordinate length if one were to list every possible combination of genes/vectors/enzymes/hosts that can be made to run a reverse alpha oxidation pathway.

Materials & Methods

Enzymes of interest can be expressed from vectors such as pCDFDuet-1 (MERCK, Germany), which makes use of the DE3 expression system. Genes can be codon optimized according to the codon usage frequencies of the host organism and synthesized by a commercial vendor or in-house. However, thousands of expression vectors and hosts are available, and this is a matter of convenience.

The genes can be amplified by PCR using primers designed with 15-22 base pairs of homology for the appropriate vector cut site. For enzymes that will not require a 6×-histidine tag fusion for purification, pCDFDuet-1 can be linearized with NcoI and EcoRI. Enzymes that will be purified by Ni-NTA column will make use of the 6×-HIS tag in pCDFDuet-1. The vector can be linearized using only EcoRI in this case.

The PCR product can be inserted into the vector using e.g., the In-Fusion HD EcoDry Cloning System and the vector transformed by heat shock into competent E. coli cells. Transformants can be selected on solid media containing the appropriate antibiotic. Plasmid DNA can be isolated using any suitable method, including QIAprep Spin Miniprep Kit (QIAGEN, Limburg), and the construct confirmed by PCR and sequencing. Confirmed constructs can be transformed by e.g., electroporation into a host strain such as E. coli for expression, but other host species can be used with suitable expression vectors and possible codon optimization for that host species.

Expression of the desired enzymes from the constructed strain can be conducted in liquid culture, e.g., shaking flasks, bioreactors, chemostats, fermentation tanks and the like. Gene expression is typically induced by the addition of a suitable inducer, when the culture reaches an OD550 of approximately 0.5-0.8. Induced cells can be grown for about 4-8 hours, at which point the cells can be pelleted and saved to −20° C. Expression of the desired protein can be confirmed by running cell pellet samples on SDS-PAGE.

The expressed enzyme can be directly assayed in crude cell lysates, simply by breaking the cells by chemical, enzymatic, heat or mechanical means. Depending on the expression level and activity of the enzyme, however, purification may be required to be able to measure enzyme activity over background levels. Purified enzymes can also allow for the in vitro assembly of the pathway, allowing for its controlled characterization.

N- or C-terminal HIS-tagged proteins can be purified using e.g., a Ni-NTA Spin Kit (Qiagen, Venlo, Limburg) following the manufacturer's protocol, or other methods could be used. The HIS-tag system was chosen for convenience only, and other tags are available for purification uses. Further, the proteins in the final assembled pathway need not be tagged if they are for in vivo use. Tagging was convenient, however, for the enzyme characterization work performed herein.

Reaction conditions for enzyme assays can vary greatly with the type of enzyme to be tested. In general, however, enzyme assays follow a similar general protocol. Purified enzyme or crude lysate is added to suitable reaction buffer. Reaction buffers typically contain salts, necessary enzyme cofactors, and are at the proper pH. Buffer compositions often change depending on the enzyme or reaction type. The reaction is initiated by the addition of substrate, and some aspect of the reaction related either to the consumption of a substrate or the production of a product is monitored.

Choice of the appropriate monitoring method depends on the compound to be measured. Spectrophotometric assays are convenient because they allow for the real time determination of enzyme activity by measuring the concentration dependent absorbance of a compound at a certain wavelength. There are not always compounds with a measureable absorbance at convenient wavelengths in the reaction, unfortunately. In these situations, other methods of chemical analysis may be necessary to determine the concentration of the involved compounds.

Gas chromatography (GC) is convenient for the quantification of volatile substances, of which fatty acids and aldehydes are of particular relevance. Internal standards, typically one or more molecules of similar type not involved in the reaction, are added to the reaction mixture, and the reaction mixture is extracted with an organic solvent, such as hexane. Fatty acid samples, for example, can be dried under a stream of nitrogen and converted to their trimethylsilyl derivatives using BSTFA and pyridine in a 1:1 ratio. After 30 minutes incubation, the samples are once again dried and resuspended in hexane to be applied to the GC. Aldehyde samples do not need to be derivatized. Samples can be run e.g., on a Varian CP-3800 gas chromatograph (VARIAN ASSOCIATES, Palo Alto, CA) equipped with a flame ionization detector and HP-5 capillary column (AGILENT Tech., Santa Clara, CA).

Once the pathway has been fully studied in vitro, the pathway can be constructed in vivo with greater confidence. The strain construction for the in vivo pathway operation should allow for the well-defined, controlled expression of the enzymes of the pathway. As before, E. coli or yeast will be a host of choice for the in vivo pathway, but other hosts could be used. The Duet system, for example, allows for the simultaneous expression of up to eight proteins by induction with IPTG in E. coli, and initial experiments will use this host.

Pathway enzymes can also be inserted into the host chromosome, allowing for the maintenance of the pathway without requiring antibiotics to ensure the continued upkeep of plasmids. There are also, theoretically, an infinite number of genes that can be placed on the chromosome, as chromosomal expression does not require separate origins of replication as is the case with plasmid expression.

DNA constructs for chromosomal integration usually include an antibiotic resistance marker with flanking FRT sites for removal, as described by Datsenko and Wanner, a well characterized promoter, a ribosome binding site, the gene of interest, and a transcriptional terminator. The overall product is a linear DNA fragment with 50 base pairs of homology for the target site on the chromosome flanking each side of the construct.

However, the Flp-FRT recombination method is only one system for adding genes to a chromosome, and other systems are available, such as the RecBCD pathway, the RecF pathway, RecA recombinase, non-homologous end joining (NHEJ), Cre-Lox recombination, TYR recombinases and integrases, SER resolvases/invertases, SER integrases, PhiC31 Integrase, and the like. Chromosomal modifications in E. coli can also achieved by the method of recombineering, as originally described by Datsenko and Wanner.

In a recombineering method, for example, the cells are prepared for electroporation following standard techniques, and the cells transformed with linear DNA that contains flanking 50 base pair targeting homology for the desired modification site. For seamless integration of a DNA construct, a two-step approach can be taken using a cassette that contains both positive and negative selection markers, such as the combination of cat and sacB. In the first round of recombineering, the cat-sacB cassette with targeting homology for the desired modification site is introduced to the cells. The cat gene provides resistance to chloramphenicol, which allows for positive recombinants to be selected for on solid media containing chloramphenicol. A positive isolate can be subjected to a second round of recombineering introducing the desired DNA construct with targeting homology for sites that correspond to the removal of the cat-sacB cassette. The sacB gene encodes for an enzyme that provides sensitivity to sucrose. Thus, growth on media containing sucrose allows for the selection of recombinants in which the cat-sacB construct was removed. P1 phage lysates can be made from isolates confirmed by PCR and sequencing. The lysates can be used to transduce the modification into desired strains, as described previously.

Engineered strains expressing the designed pathway can be cultured under the following or similar conditions. Overnight cultures started from a single colony can be used to inoculate flasks containing appropriate media. Cultures are grown for a set period of time, and the culture media analyzed. The conditions will be highly dependent on the specifications of the actual pathway and what exactly is to be tested. For example, the ability for the pathway to be used for autotrophic growth can be tested by the use of formate or formaldehyde as a substrate in MOPS minimal media, as described by Neidhardt, supplemented with appropriate antibiotics, and inducers. Mixotrophic growth can be characterized by the addition of both single carbon compounds and glucose or glycerol.

Analysis of culture media after fermentation provides insight into the performance of the engineered pathway. Quantification of longer chain fatty acid products can be analyzed by GC. Other metabolites, such as short chain organic acids and substrates such as glucose or glycerol can be analyzed by HPLC. Once the pathway is fully functional, the cultures can be grown in chemostat, providing continuous uninterrupted production of product if desired.

Various-omics techniques, such as microarray or 2D-PAGE can give information about gene expression or protein expression, respectively. Genome scale modeling allows for the identification of additional modifications to the host strain that might lead to improved performance. Deletion of competing pathways, for example, might increase carbon flux through the engineered pathway for product production.

Standard molecular biology techniques were used for gene cloning, plasmid isolation, and E. coli transformation. Native E. coli genes were amplified from E. coli MG1655 genomic DNA using primers to append 15 bp of homology on each end of the gene insert for recombination into the vector backbone. Genes from other organisms were codon optimized and synthesized by either GeneArt (LIFE TECH., CA or GENSCRIPT, NJ). Plasmids were linearized by the appropriate restriction enzymes and recombined with the gene inserts using the In-Fusion HD Eco-Dry Cloning system (CLONTECH Lab., CA). The mixture was subsequently transformed into Stellar competent cells (CLONTECH Lab).

Transformants that grew on solid media (LB+Agar) supplemented with the appropriate antibiotic were isolated and screened for the gene insert by PCR. Plasmid was isolated from the verified transformants and the sequence of the gene insert was further confirmed by DNA sequencing (LONE STAR LABS, TX). Plasmids (also referred to as vectors) in each case contain at least one promoter, a ribosome binding site for each gene, the gene(s) of interest, at least one terminator, an origin of replication, and an antibiotic resistance marker. Exemplary plasmids are shown in FIGS. 11, 15, and 22A, 22B, 23, and 24.

2-hydroxyhexadecanoyl-CoA was prepared by the n-hydroxysuccinimide method (Blecher, 1981). In summary, the n-hydroxysuccinimide ester of 2-hydroxyhexadecanoic acid was prepared by reacting n-hydroxysuccinimide with the acid in the presence of dicyclohexylcarbodiimide. The product was filtered and purified by recrystallization from methanol to give pure n-hydroxysuccinimide ester of 2-hydroxyhexadecanoic acid. The ester was reacted with CoA-SH in presence of thioglycolic acid to give 2-hydroxyhexadecanoyl-CoA. The 2-hydroxyhexadecanoyl-CoA was purified precipitation using perchloric acid, filtration, and washing the filtrate with perchloric acid, diethyl ether, and acetone.

Formyl-CoA was prepared by first forming formic ethylcarbonic anhydride as previously described (Parasaran & Tarbell, 1964). Briefly, formic acid (0.4 mmol) and ethyl chloroformate (0.4 mmol) were combined in 4 mL anhydrous diethyl ether and cooled to −20° C. 0.4 mmol triethylamine was added to the mixture and the reaction was allowed to proceed at −20° C. for 30 minutes. The reaction mixture was filtered over glass wool to give a solution containing formic ethylcarbonic anhydride in diethyl ether. To obtain formyl-CoA, 7 µmol CoASH was dissolved in 5 mL 3:2 water: tetrahydrofuran, to which 10 mg of sodium bicarbonate were added. The solution of formic ethylcarbonic anhydride was added dropwise to the CoASH solution with vigorous agitation, after which the organic phase was evaporated under a stream of nitrogen. The mixture was kept at 4° C. for two hours, after which any remaining diethyl ether was evaporated under nitrogen. Solid phase extraction using a C18 column was used to purify formyl-CoA from the reaction mixture. Formyl-CoA was eluted from the C18 column in methanol and stored in 2:1 methanol: ammonium acetate pH 5.5.

A plasmid containing the codon optimized gene encoding 6xHIS-tagged Lmo1179 from *Lysteria monocytogenes* was constructed as described above. The resulting construct, FIG. 11, was transformed into *E. coli* BL21 (DE3) for expression. The resulting strain was cultured in 50 mL of TB media containing 50 µg/mL spectinomycin in a 250 mL flask. When the culture reached an OD550 of approximately 0.6, expression was induced by the addition of 0.1 mM IPTG, and the cells were harvested by centrifugation after overnight incubation at room temperature.

The resulting cell pellet was resuspended in Bacterial Protein Extraction Reagent (B-PER) (THERMO SCI., MA) to an OD550 of approximately 40, to which approximately 5000 U of lysozyme and approximately 250 U of Benzonase nuclease (SIGMA-ALDRICH Co., MO) were added. The cell mixture was left at room temperature until completely clarified to give the cell extract. 1 M stock solution of imidazole was added to provide a final concentration of 10 mM imidazole in the cell extract.

Figure 12:
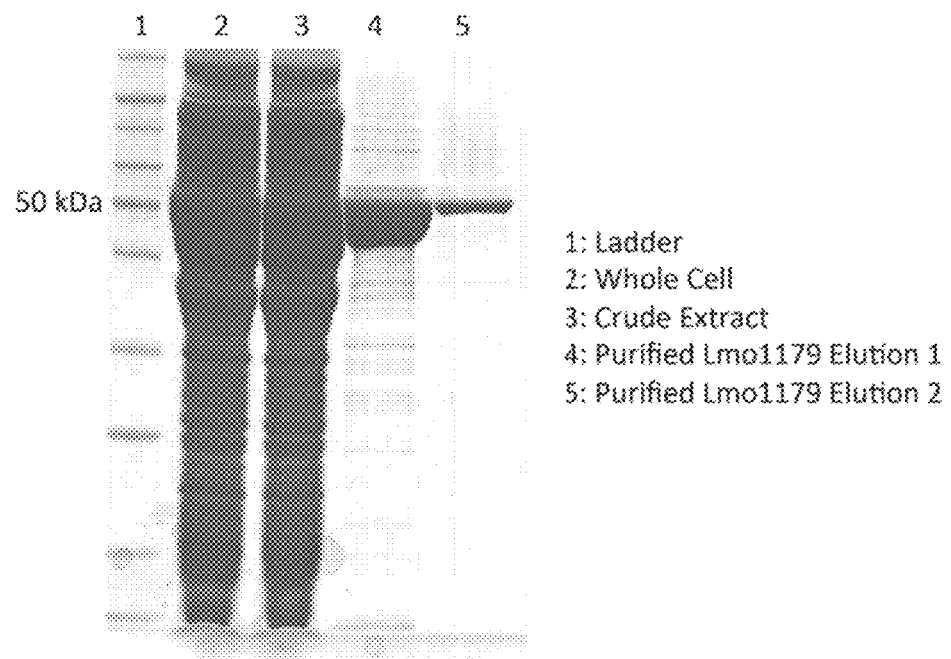
FIG. 12. SDS-PAGE showing expression and purification of *Lysteria monocytogenes* acylating aldehyde reductase Lmo1179 from *E. coli*.

The HIS-tagged Lmo1179 protein was purified from the cell extract using Talon Metal Affinity Resin (CLONTECH Lab.). In short, a 250 µL resin bed was equilibrated twice using 2.5 mL of a buffer containing 50 mM sodium phosphate, 300 mM NaCl, and 10 mM imidazole at pH 7.5 (NPI-10). The cell extract was added to the resin and the mixture shaken gently for 20 minutes on ice. The resin was then washed twice with 2.5 mL buffer NPI-20 (same as NPI-10 but with 20 mM imidazole), shaking gently on ice for 15 minutes each wash. The resin was then transferred to a gravity column and washed once with 1.25 mL NPI-20. Finally, the desired protein was eluted using 1.25 mL of buffer NPI-250 (same as buffer NPI-10 but with 250 mM imidazole), and the eluate collected in 500 µL fractions. An sample purification of Lmo1179 is shown in FIG. 12.

A plasmid containing the codon optimized gene encoding human HIS-tagged HACL1 was constructed as described. The resulting construct, FIG. 15, was transformed into *S. cerevisiae* InvSC1 (Life Tech.). The resulting strain was cultured in 50 mL of SC-URA media containing 2% glucose at 30° C. for 24 hours. The cells were pelleted and the required amount of cells were used to inoculate a 250 mL culture volume of SC-URA media containing 0.2% galactose, 1 mM $MgCl_2$, and 0.1 mM thiamine to 0.4 OD600. After 20 hours incubation with shaking at 30° C., the cells were pelleted and saved.

Figure 16:
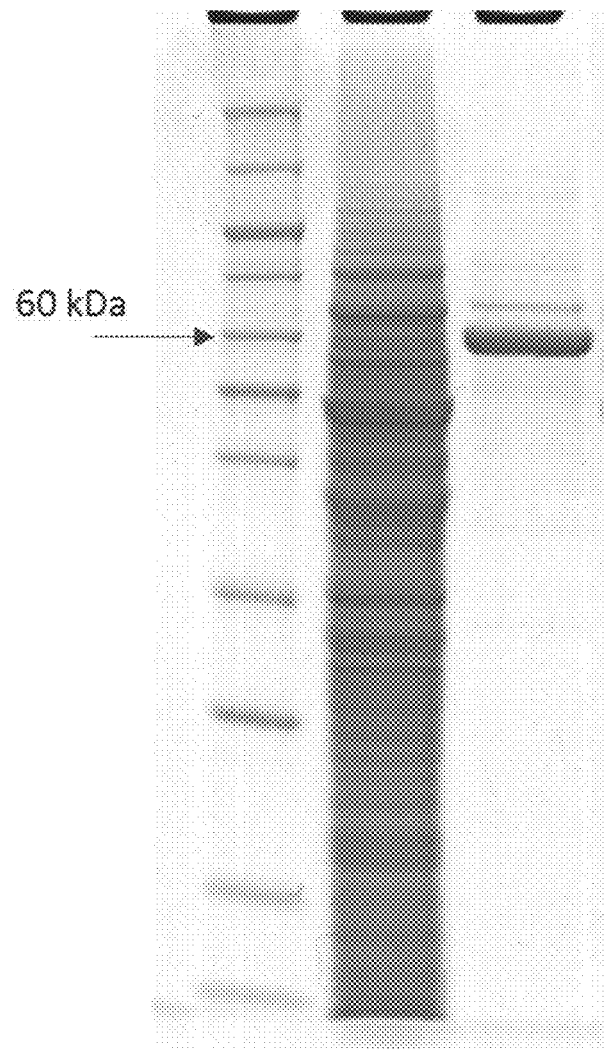
FIG. 16. SDS-PAGE showing the purification of hydroxyl-acyl-CoA lyase HACL1 from *Saccharomyces cerevisiae*. Lane 1 corresponds to the protein ladder. Lane 2 is the *S. cerevisiae* cell extract. Lane 3 corresponds to purified HACL1.

When needed, the cell pellets were resuspended to an OD600 of approximately 100 in a buffer containing 50 mM potassium phosphate pH 7.4, 0.1 mM thiamine pyrophosphate, 1 mM $MgCl_2$, 0.5 mM AEBSF, 10 mM imidazole, and 250 units of Benzonase nuclease. To the cell suspension, approximately equal volumes of 425-600 µm glass beads were added. Cells were broken in four cycles of 30 seconds of vortexing at 3000 rpm followed by 30 seconds on ice. The glass beads and cell debris were pelleted by centrifugation and supernatant containing the cell extract was collected. The HIS-tagged HACL1 was purified from the cell extract using Talon Metal Affinity Resin as described above, with the only modification being the resin bed volume and all subsequent washes were halved. The eluate was collected in two 500 µL fractions. A sample purification of HACL1 is shown in FIG. 16.

*E. coli* fadA and fadB genes were cloned from MG1655 genomic DNA into the pUCBB-ntH6 vector to yield a constitutively expressed gene with an amino-terminal HIS-tag that can be cleaved by Thrombin. For AtoB and thioesterase characterization assays, the pCA24N-gene (-gfp) plasmids from the ASKA collection were used (Kitagawa et al., 2005). For expression of *E. gracilis* TER for kinetic characterization, the egTER gene was cloned into pTrcHis2A using the In-Fusion protocol (CLONTECH LAB.) following PCR amplification from the aforementioned codon-optimized egTER containing plasmid.

Cultures for enzymatic assays were grown overnight in 100 mL of LB media at 37° C. in 250 mL baffled flasks (WHEATON IND., NJ) in *E. coli* BL21 (DE3) cells induced with either 1 mM IPTG (pCA24N, pTrcHis2A) or 1 mM Arabinose (pUCBB-pBAD) at an OD600 of about 0.6, or expressed constitutively (pUCBB-ntH6). Reactions were monitored on either a Synergy HT plate reader (BIOTEK INSTR., VT) at 25° C. (for reactions monitored at 300 nm or higher) or in a Biomate 5 Spectrophotometer (THERMO SCI.,) for reactions at 263 nm.

Cells were lysed using Bacterial Protein Extraction Reagent (B-PER) (Thermo Sci.) as per the prescribed protocol in order to obtain the supernatant containing the active enzymes. FadE and YdiO were purified following previously established methods using the same growth conditions mentioned above. Cell pellets were resuspended in 40 mL of 50 mM potassium phosphate buffer pH 7.2 and broken by disruption EmulsiFlex-C5 homogenizer (AVESTIN, ON). Disrupted cells were then spun for 90 min at 4° C. at 120,000×g in an Optima L-80XP Ultracentrifuge (BECKMAN-COULTER, IL) to produce the supernatant used for assays.

For specific activity assays (reported in µmol substrate/mg protein/min) these supernatant fractions were utilized, and protein concentration was established using the Bradford Reagent (Thermo Sci.) using BSA as the protein standard. Linearity was established for each reaction and the background non-enzymatic rate was subtracted to establish the activity. HIS-tagged proteins of AtoB, FadB, and egTER were purified from the B-PER supernatant fractions using Talon Metal Affinity Resin (CLONTECH LAB.) using gravity purification.

In short, the supernatant was mixed for 1 hr at room temperature on a LabQuake rotator (FISHER SCI., PA) with approximately 2 mL of Talon Resin (1 mL resin/0.3 mg supernatant protein) that was pre-washed twice with Buffer A (50 mM Tris pH 7.9, 5 mM $MgCl_2$, 100 mM NaCl, 5 mM Imidazole). Resin was then spun at 700×g for 5 min to remove the non-bound proteins, washed with 20× (40 mL) Buffer A, resuspended in 20× (40 mL) Buffer B (Buffer A with 20 mM imidazole) and loading onto a gravity column. Buffer B was then drained off and the protein was eluted with 20 mL of Buffer C (Buffer A with 250 mM imidazole). The eluted fraction was then concentrated and used for kinetic characterizations. Enzyme concentration was established by measuring the absorbance at 260 nm and extinction coefficients predicted for each enzyme by the ProtParam program (web.expasy.org/protparam/).

For crude extract assays, cells (JST07-atoB$^{CT5}$-fadB$^{CT5}$, JST07-atoB$^{CT5}$-fadB$^{CT5}$/pCDF-yciA) were grown in 25 mL LB medium in 125 mL Erlenmeyer flasks at 37° C. and 200 rpm. Cumate 0.2 mM and IPTG 0.1 mM were added at OD550 0.3~0.5 for the overexpression of fadB, atoB under control of cumate promoter (CT5) and yciA under T7 promoter respectively followed by additional cultivation for 4 hr under the same conditions before harvested by centrifugation at 5000×g for 10 min. Harvested cells were washed once with a 9 g/L NaCl solution, and stored as cell pellets at −80° C. until used. Frozen cells were re-suspended in Tris-HCl (50 mM, pH 7.5) buffer supplemented by 1 mM dithiothreitol (DTT) for the cell disruption carried out by using glass (0.1 mm diameter) beads.

In Vitro Pathway Characterization

Figure 13:
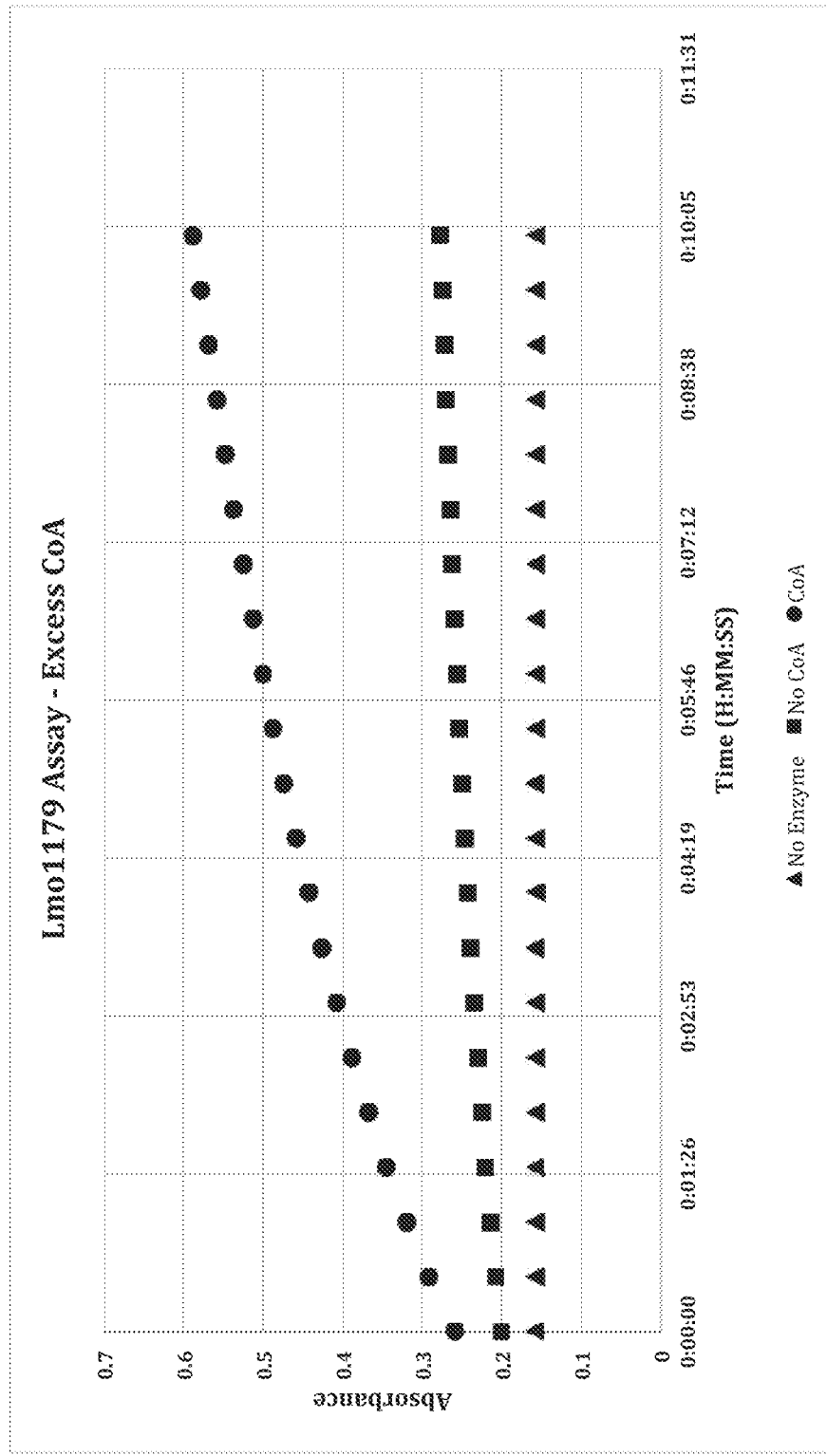
FIG. 13. Time course of absorbance at 340 nm corresponding to the production of NADH in the assay of *Lysteria monocytogenes* acylating aldehyde reductase Lmo1179.
Figure 14:
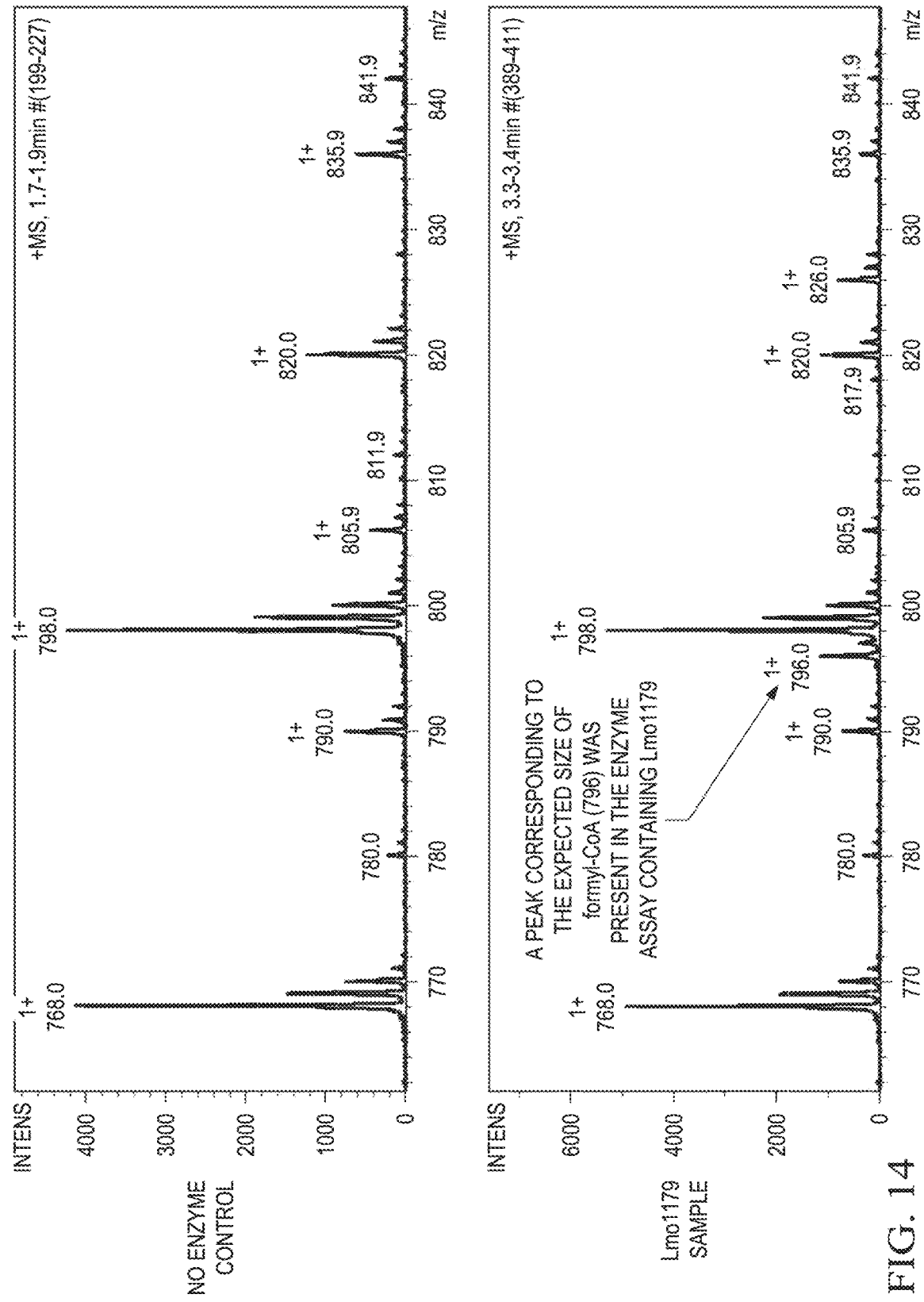
FIG. 14. ESI-TOF MS data of the –CoA content of *Lysteria monocytogenes* acylating aldehyde reductase Lmo1179 reaction assay mixtures after solid phase extraction.

Genes that encode the enzymes of the engineered pathway were cloned and expressed as described above. The purified enzymes were assessed for their ability to catalyze the proposed reactions as summarized in Table 2 and FIG. 10A-B. The engineered pathway consists of at least an extender generation module, which results in the production of formyl-CoA; an elongation module, which allows for the iterative elongation of a carbon backbone; and a termination module, which allows for the production of products from intermediates of the other modules. A regeneration module is also described, but is optional, and can be omitted if the cycle runs only once. Here, we described testing in vitro the steps that make up an implementation that uses formaldehyde to produce saturated fatty acids.

in 23 mM potassium phosphate buffer pH 7.0, 1 mM CoASH, 0.5 mM NAD$^+$, 20 mM 2-mercaptoethanol, and 50 mM formaldehyde. The reaction was monitored by measuring absorbance at 340 nm, corresponding to the production of NADH. CoA compounds were extracted from the reaction mixture by solid phase extraction (SPE) using a C18 column, and the masses of the extracted CoAs were determined by ESI-TOF MS. The inclusion of Lmo1179 in the reaction mixture resulted in the conversion of formaldehyde to formyl-CoA as indicated by the coproduction of NADH (FIG. 13). Mass spectrometry analysis confirmed the production of formyl-CoA by Lmo1179. A peak at the expected mass of formyl-CoA (796) was identified in the sample incubated with enzyme, as shown in FIG. 14. The peak was not present in the no enzyme control (FIG. 14), indicating that Lmo1179 produced formyl-CoA.

Elongation module: The elongation module consists of the ligation of an aldehyde and formyl-CoA, followed by steps that convert the produced 2-hydroxyacyl-CoA back to an aldehyde 1 carbon longer than the starting aldehyde.

To catalyze the ligation step, human HACL1 was cloned (FIG. 15A-B), expressed, and purified (FIG. 16) in *S. cerevisiae* as described above. Purified HACL1 was tested for its native catabolic activity by assessing its ability to cleave 2-hydroxyhexadecanoyl-CoA to pentadecanal and formyl-CoA. Enzyme assays were performed in 50 mM tris-HCl pH 7.5, 0.8 mM MgCl$_2$, 0.02 mM TPP, 6.6 μM

TABLE 2

| Enzyme class | Enzyme | Measured specific activity (μmol/mg protein/min) | Reference |
|---|---|---|---|
| Extender Generation | | | |
| 1  Acylating aldehyde reductase | *L. monocytogenes* Lmo1179 | 0.32 | This work |
| Elongation | | | |
| 2  2-hydroxyacyl-CoA lyase | *H. sapiens* HACL1 | Activity observed | This work |
| 3  2-hydroxyacyl-CoA dehydratase | *Clostridium propionicum* LcdABC | 1.21 ± 0.08 | (HOFMEISTER & BUCKEL, 1992) |
| 4  Trans-2-enoyl-CoA reductase | *E. gracilis* Ter | 5.4 ± 0.6 | This work |
| 5  Acyl-CoA reductase | *E. coli* AdhE | 0.073 ± 0.001 | This work |
|  | *E. coli* MhpF | 0.009 ± 0.003 | This work |
| 10  1,2-diol oxidoreductase | *E. coli* FucO | 5.08 ± 0.08 | This work |
| 11  Diol dehydratase | *Klebsiella oxytoca* pddABC | 106 | (Tobimatsu et al., 1997) |
| Termination | | | |
| 6  Enoyl-CoA hydratase | *E. coli* FadB | 0.051 ± 0.004 | This work, (Binstock & Schulz, 1981) |
| 7  3-hydroxyacyl-CoA dehydrogenase | *E. coli* FadB | 0.185 ± 0.001 | This work, (Binstock & Schulz, 1981) |
| 8  3-ketoacyl-CoA thiolase | *E. coli* AtoB | 0.36 ± 0.05 | This work |
|  | *E. coli* FadA | 0.013 ± 0.002 | This work |
| 9  Thioesterase | *E. coli* FadM | 0.027 ± 0.001 | This work |
|  | *E. coli* TesA | 0.049 ± 0.002 | This work |
|  | *E. coli* TesB | 0.101 ± 0.002 | This work |
|  | *E. coli* YbgC | 0.045 ± 0.007 | This work |
|  | *E. coli* YciA | 2.9 ± 0.2 | This work |
|  | *E. coli* YdiI | 0.0917 ± 0.0007 | This work |

Figure 17:
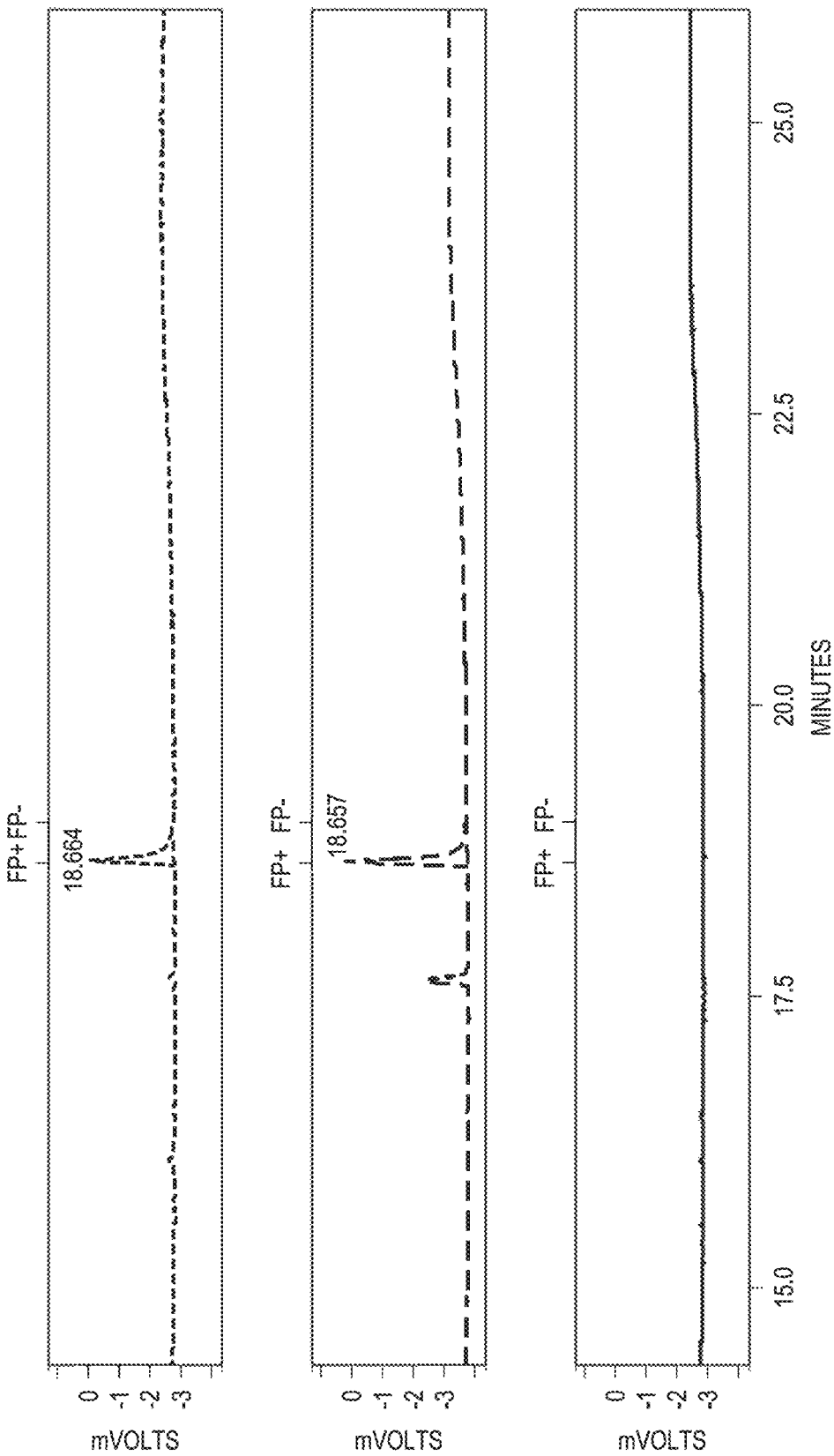
FIG. 17. GC-FID chromatograms of pentadecanal content in HACL1 degradative reaction mixtures after extraction with hexane. Top: pentadecanal standard; Middle: HACL1 assay sampled; Bottom: no enzyme control. In samples containing HACL1, a pentadecanal peak is seen, while there is no peak in the sample in which enzyme was omitted.

Extender generation module: *Lysteria monocytogenes* Lmo1179 was cloned (FIG. 11), expressed, and purified (FIG. 12) in *E. coli* as described above. The purified enzyme was evaluated for its ability to convert formaldehyde into the extender unit formyl-CoA. Enzyme assays were performed BSA, and 0.3 mM 2-hydroxyhexadecanoyl-CoA. The assay mixtures were incubated for one hour at 37° C., after which the presence of pentadecanal was assessed by extraction with hexane and analysis by GC-FID. As shown in FIG. 17, pentadecanal was produced in the sample containing HACL1, but not in the control sample, which did not contain HACL1, indicating that the protein was expressed and purified in an active form.

The ability of purified HACL1 to run in the anabolic direction (reverse from the physiological direction) was also determined. An aldehyde and formyl-CoA were tested for ligation in a buffer comprised of 60 mM potassium phosphate pH 5.4, 2.5 mM $MgCl_2$, 0.1 mM TPP, 6.6 µM BSA, 5 mM aldehyde, 20% DMSO, approximately 1 mM freshly prepared formyl-CoA, and approximately 0.5 mg/mL purified HACL1. The reaction was allowed to take place at room temperature for 16 hours, after which acyl-CoAs were hydrolyzed to their corresponding acids by adjusting to pH>12.0. For instances in which a short carbon chain product was expected, for example lactate production from acetaldehyde, samples were analyzed by HPLC. In the case of longer products, for example the production of 2-hydroxyhexadecanoic acid from pentadecanal, samples were acidified with HCl and extracted with diethyl ether. The extracted diethyl ether was evaporated to dryness under a stream of nitrogen and derivatized by the addition of 1:1 BSTFA:pyridine. After incubation at 70° C. for 30 min, these samples were analyzed by GC-FID.

Figure 18:
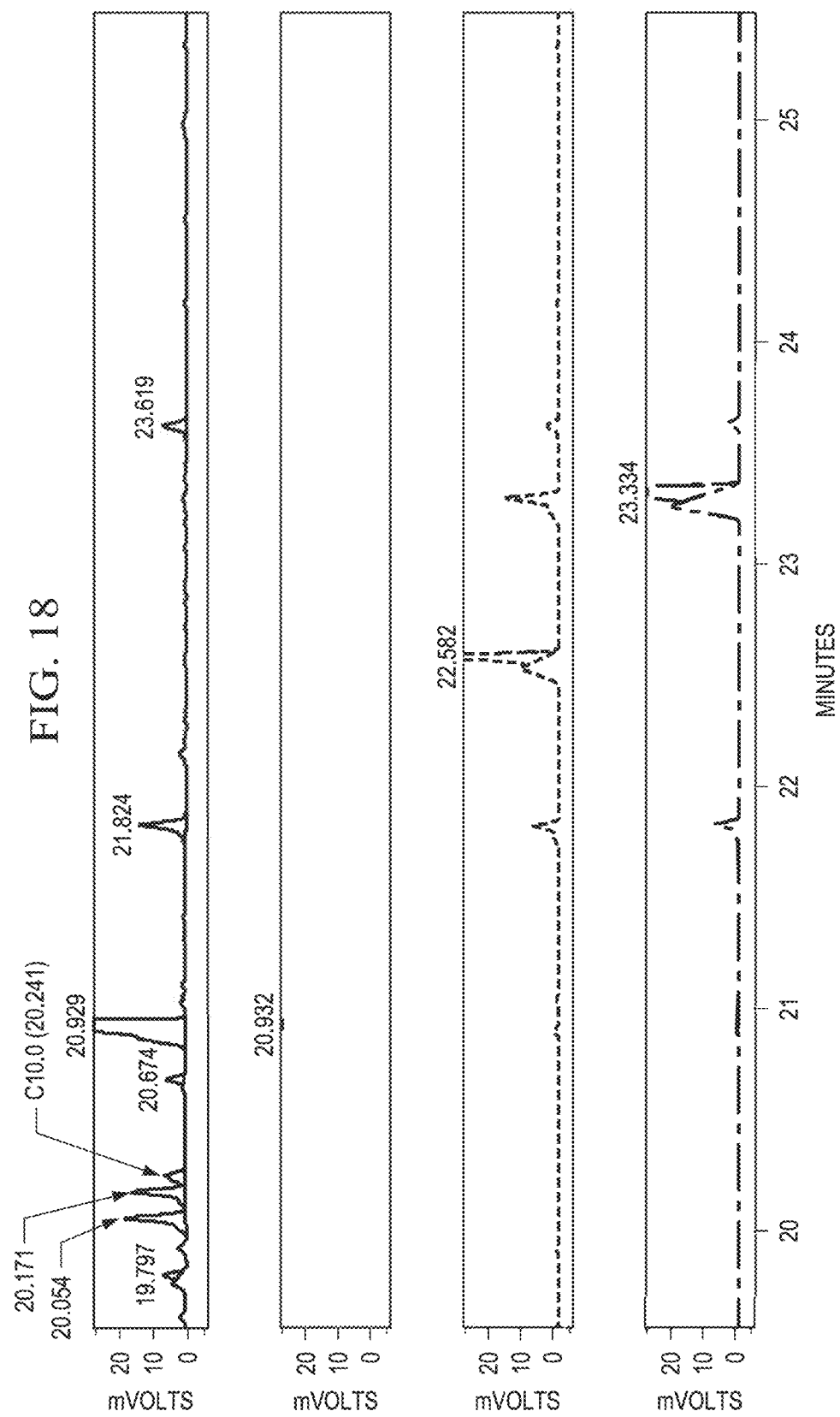
FIG. 18. GC-FID chromatograms of HACL1 synthetic reaction mixtures after hydrolysis of acyl-CoAs and derivatization. From top to bottom: no enzyme control; HACL1 sample; 2-hydroxyhexadecanoyl-CoA standard; 2-hydroxyhexanoic acid standard. HACL1 was incubated with pentadecanal and formyl-CoA and was capable of ligating the molecules to 2-hydroxyhexadecanoyl-CoA as indicated by the peaks corresponding to the standards.

When the purified enzyme was supplied with pentadecanal and formyl-CoA, as in FIG. 18, HACL1 was shown to catalyze the ligation of these molecules to 2-hydroxyhexadecanoyl-CoA as hypothesized. After hydrolysis of acyl-CoAs, the chromatogram of the sample containing enzyme shows similar peaks to the 2-hydroxyhexadecanoyl-CoA spiked standard, which are absent from the sample containing no enzyme.

Figure 19:
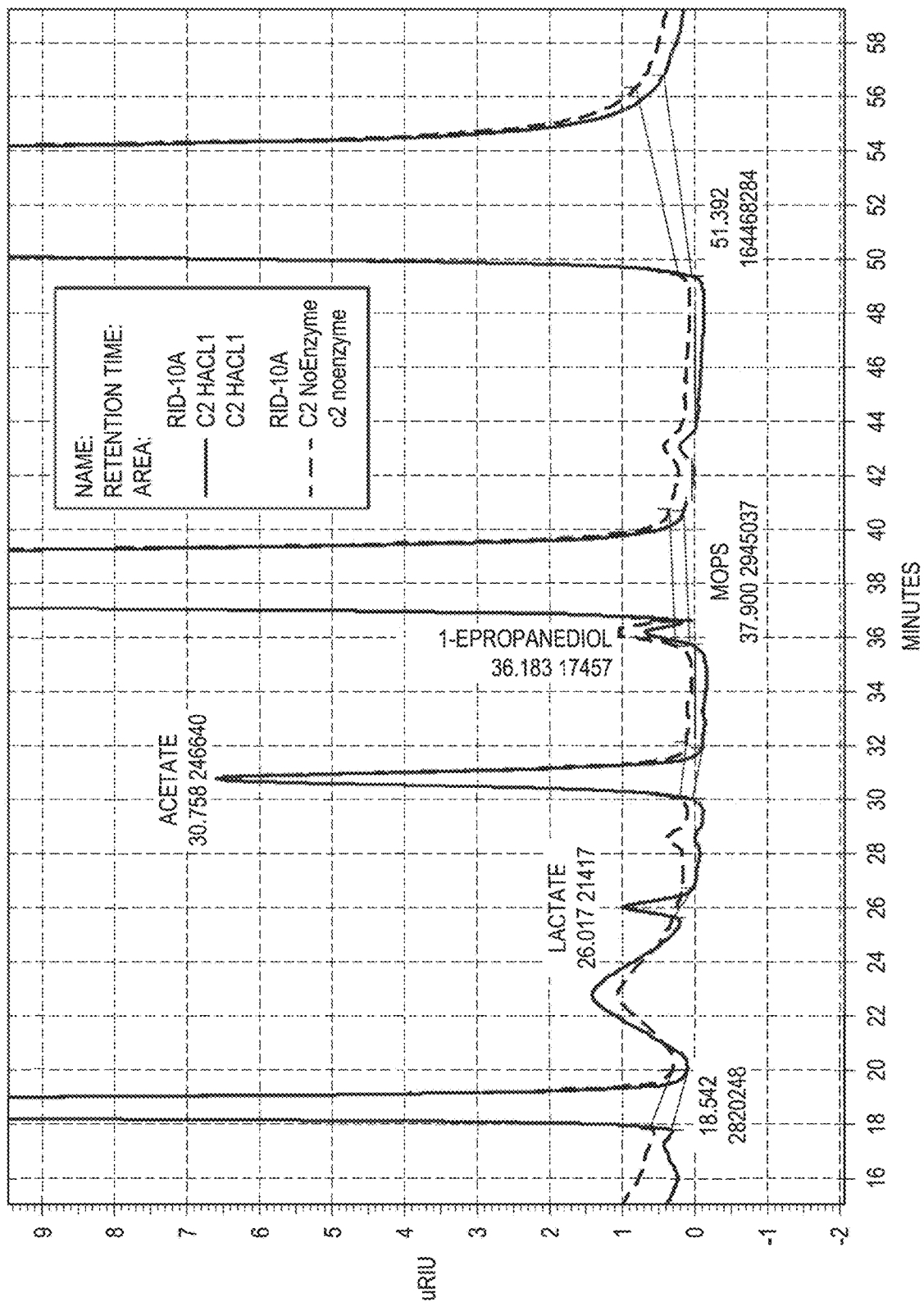

The purified HACL1 was further tested for activity on shorter aldehydes, such as the ligation of acetaldehyde or formaldehyde with formyl-CoA to produce lactoyl-CoA or glycolyl-CoA, respectively. After hydrolysis of acyl-CoAs to their acid forms, these samples were analyzed by HPLC. The presence of lactate from elongation of acetaldehyde and formyl-CoA was identified in the sample containing HACL1, but not in the no enzyme control as shown in FIG. 19.

Figure 20:
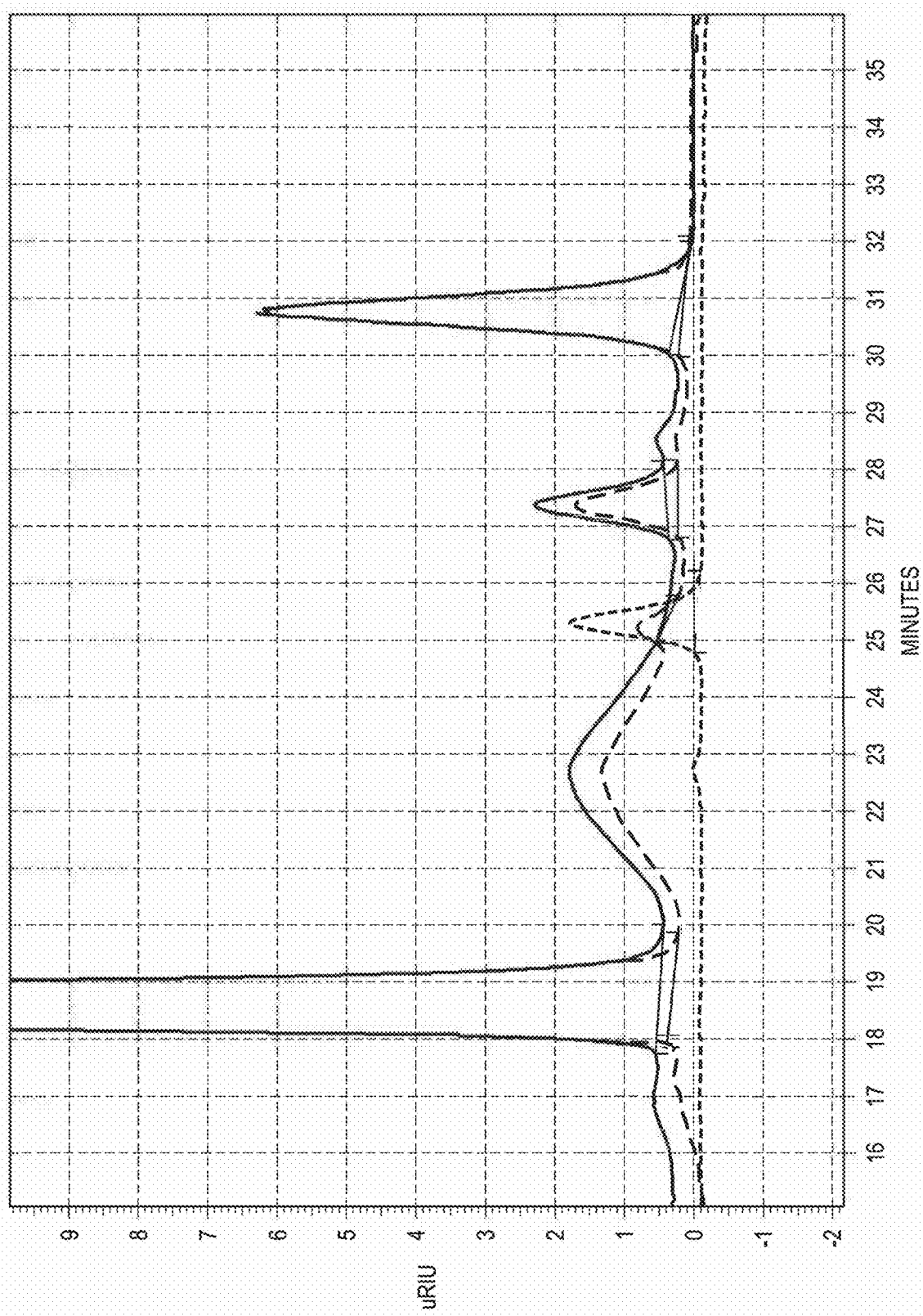
FIG. 20. HPLC chromatogram of HACL1 synthetic reaction samples incubated with formaldehyde and formyl-CoA. Solid line: no enzyme control; Dashed line: HACL1 sample; Dotted line: glycolate standard. The expected product of the ligation of formaldehyde and formyl-CoA is glycolyl-CoA, which would be expected to be hydrolyzed to its acid form, glycolate. A peak matching a glycolate standard (25.2 min) was observed in samples containing purified HACL1 and was not observed in samples that did not contain enzyme.
Figure 21A:
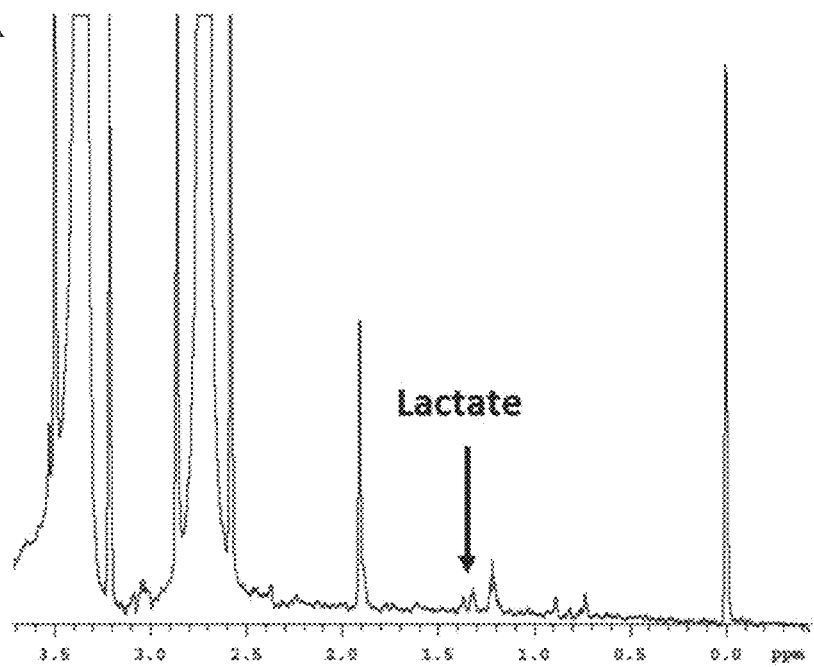
FIG. 21A-B. NMR spectra of HACL1 assay samples incubated with acetaldehyde and formyl-CoA. (21A) HACL1 sample. (21B) No enzyme control. A peak corresponding to lactate was identified in the sample containing HACL1.
Figure 21B:
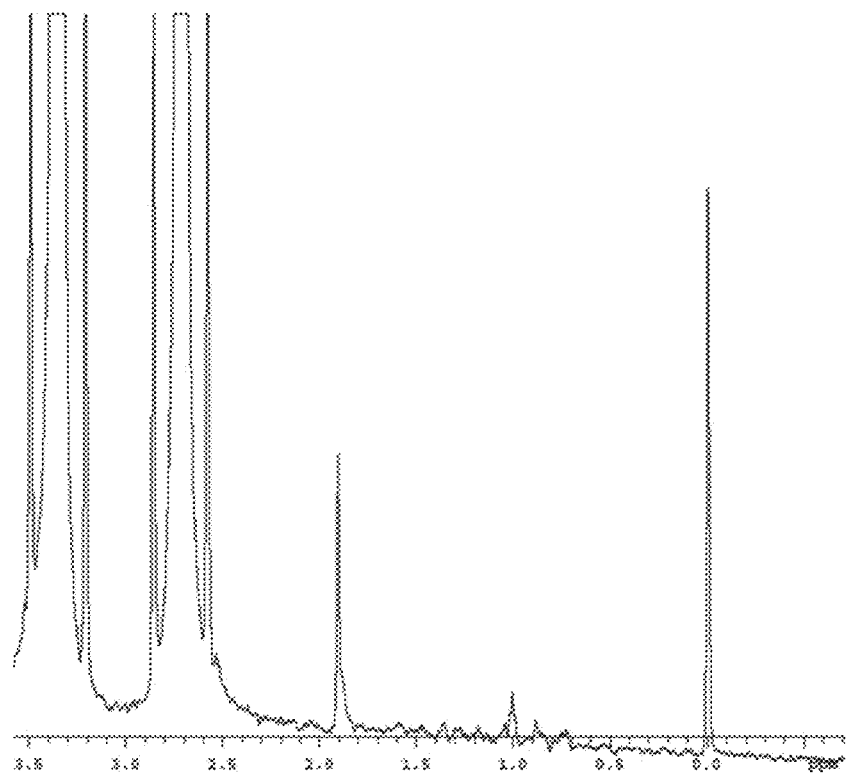
Figure 22A:
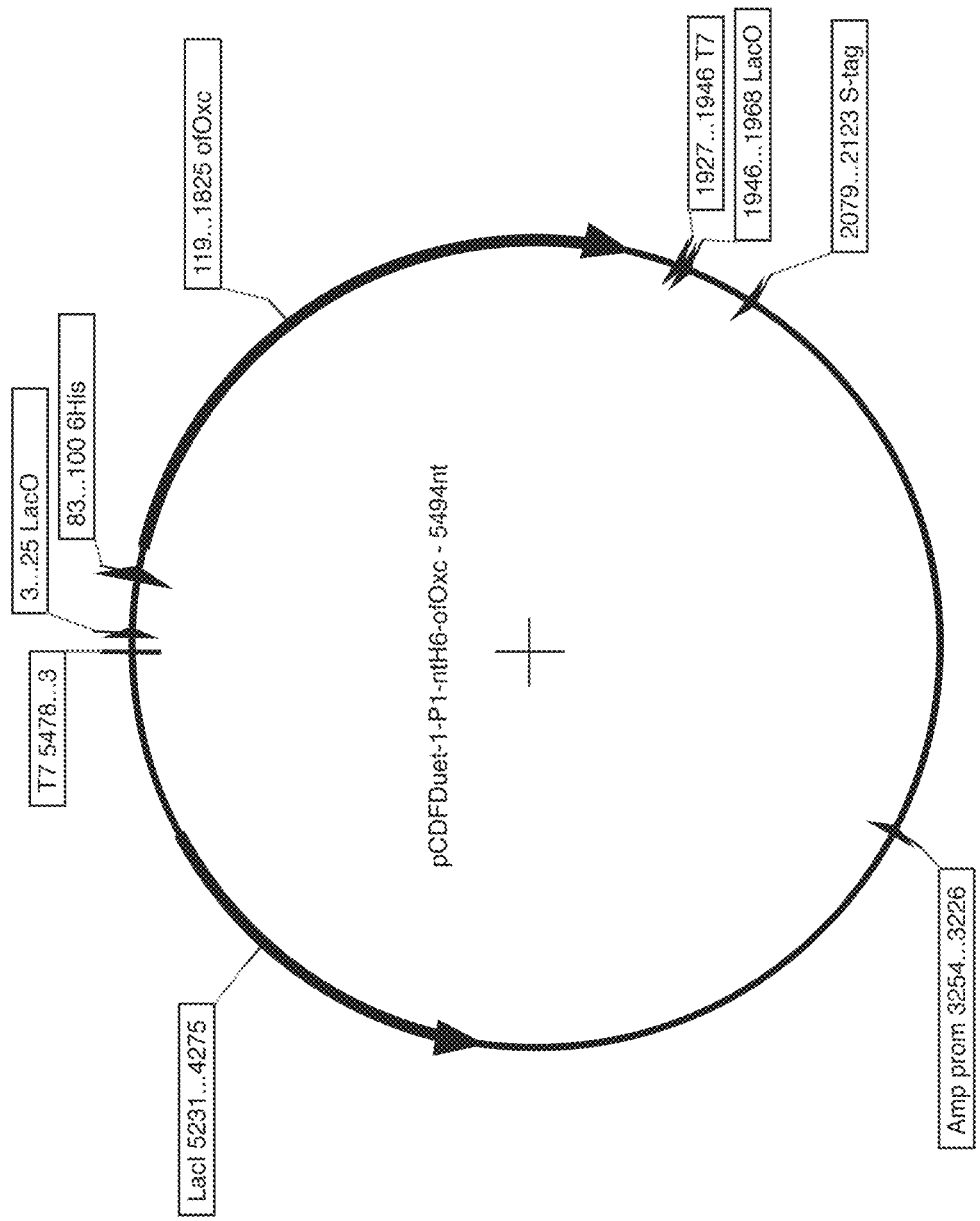
FIGS. 22A and 22B. Vector constructs encoding oxalyl-CoA decarboxylases from (A) Oxalobacter formigenes and (B) *E. coli*.
Figure 22B:
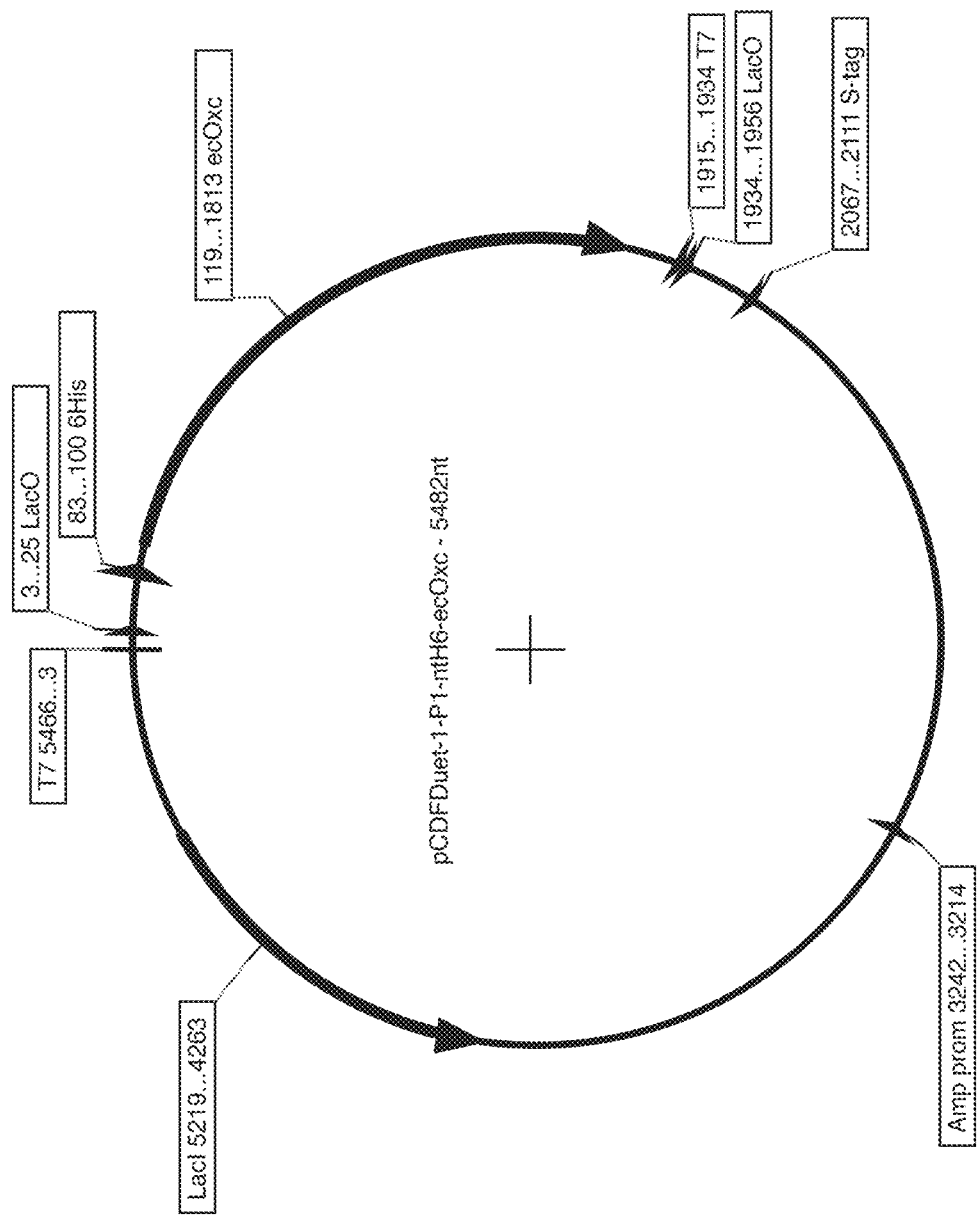
Figure 23:
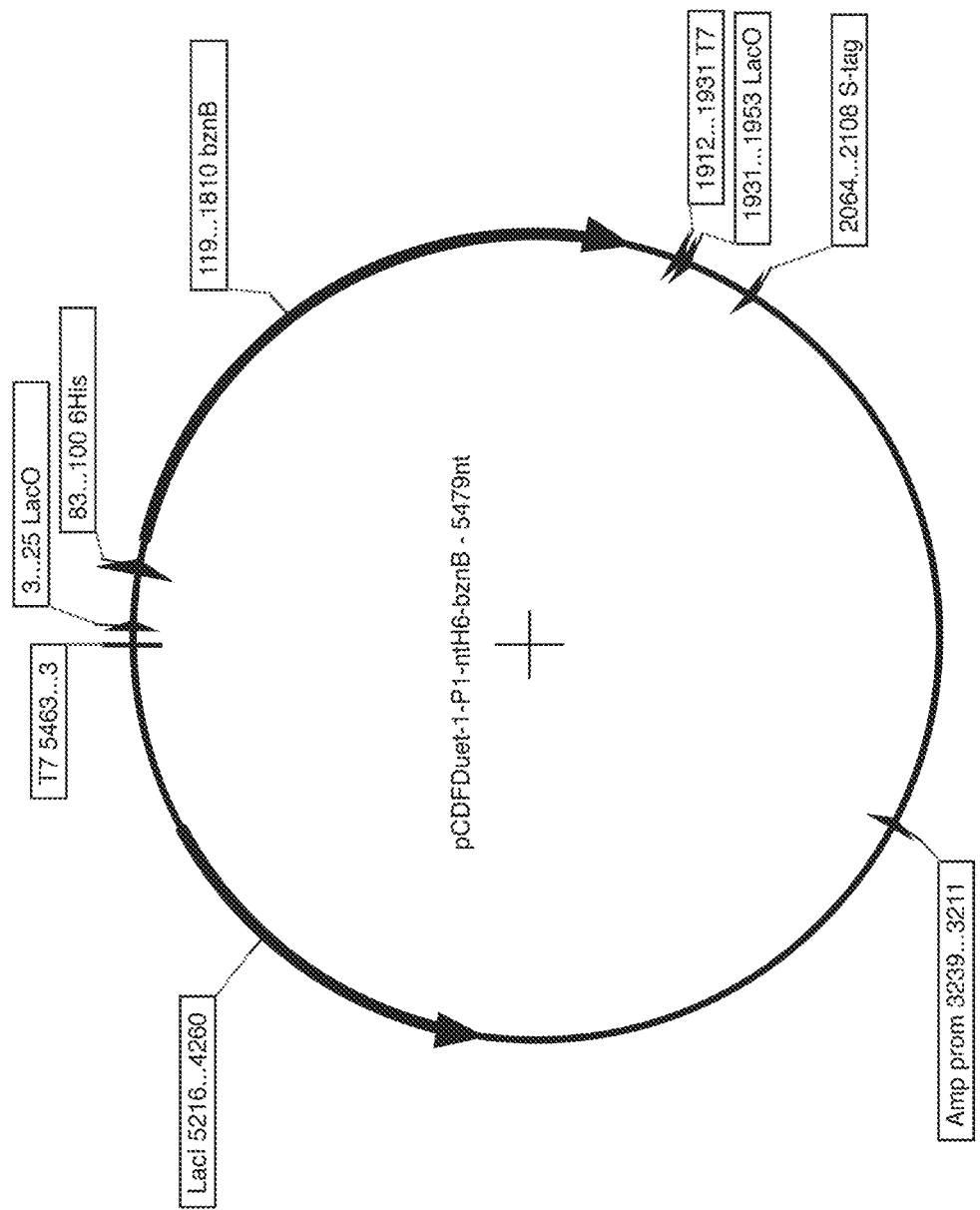
FIG. 23. Vector construct encoding benzaldehyde lyase from *Pseudomonas fluorescens*.

Similar results were observed for glycolate from formaldehyde and formyl-CoA as shown in FIG. 20. The presence of lactate in the relevant samples was confirmed by NMR, as shown in FIG. 21A-B. This demonstrates that HACL1 is capable of catalyzing the ligation of aldehydes with chain lengths ranging at least from C1-C15 with formyl-CoA, making it suitable for the engineered iterative pathway.

The 2-hydroxyacyl-CoA then undergoes dehydration to its corresponding trans-2-enoyl-CoA. A 2-hydroxyacyl-CoA dehydratase was identified as LcdABC from *Clostridium propionicum*. LcdABC has been characterized by Hofmeister and Buckel for the dehydration of 2-hydroxybutyryl-CoA to crotonyl-CoA, with specific activity corresponding to 1.21±0.08 µmol/min/mg protein (Hofmeister & Buckel, 1992). The genes encoding LcdABC were cloned as described above (FIG. 24).

Figure 25:
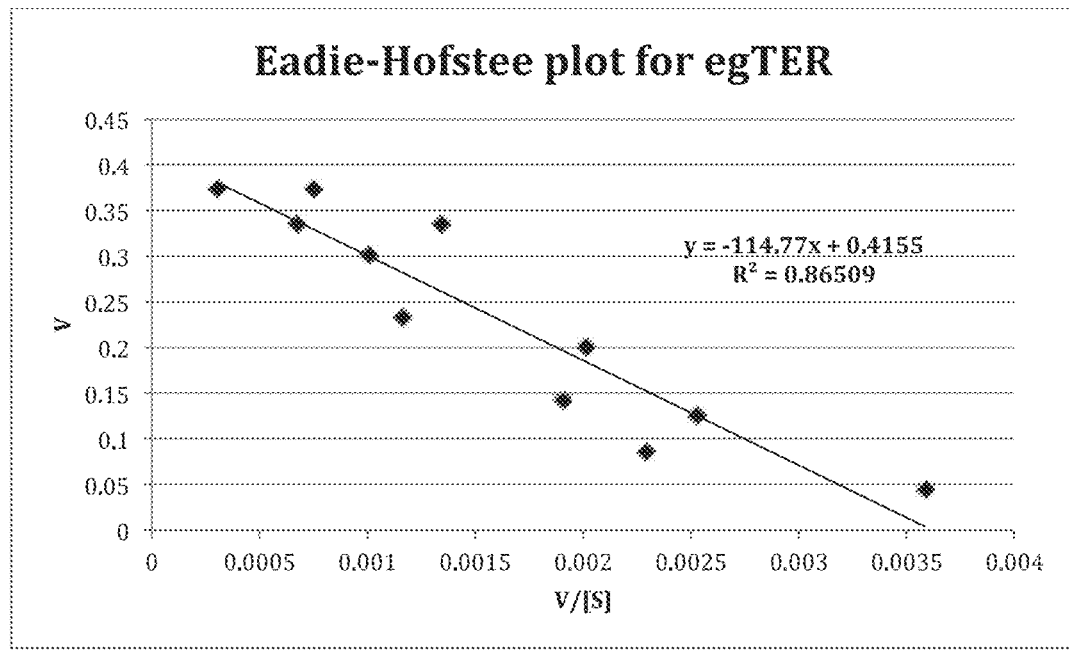
FIG. 25. Eadie-Hofstee plot for the determination of egTER enzyme kinetics. egTER is an example of transenoyl-CoA reductase (enzyme 4 in FIG. 10 and Table 2).

The trans-2-enoyl-CoA is then reduced to the saturated acyl-CoA by a trans-2-enoyl-CoA reductase. A variant from *Euglena gracilis*, EgTER, was identified and cloned as described above. After expression and purification of EgTER, in vitro assays were performed by monitoring the loss of NADH absorbance in the presence of 100 mM Tris HCL pH 7.5 and 0.2 mM NADH in a final volume of 200 µL at 25° C. This revealed that the enzyme is capable of catalyzing the conversion of crotonyl-CoA to butyryl-CoA with specific activity corresponding to 1.21±0.08 µmol/min/mg protein (FIG. 25).

The saturated acyl-CoA is finally converted to its corresponding aldehyde by an acyl-CoA reductase. Native *E. coli* acyl-CoA reductase MhpF was tested for its ability to convert butyryl-CoA to butyraldehyde (FIG. 26). *E. coli* MhpF was expressed from an ASKA collection strain (Kitagawa et al., 2005). Strains were grown anaerobically in 10 mL LB with 100 mM Tris pH 8.0, 10 g/L glucose, 50 µM $FeSO_4$, 5 M $NaH_2SeO_3$, and 5 µM $(NH_4)6Mo_7O_{24}$. The cells were grown to 0.4 OD550 at which point protein expression was induced by the addition of 0.1 mM IPTG.

After 3 hours growth, cells were pelleted and the pellet was resuspended to 40 OD in 100 mM MOPS pH 7.5. 1 mL of the cell suspension was added to 0.75 g of glass beads and the cells were disrupted for 3 minutes using a cell disruptor (Scientific Industries, Bohemia, NY, USA). The cell debris and glass beads were pelleted by centrifugation and the supernatant comprising the cell extract was used for assays.

Figure 24:
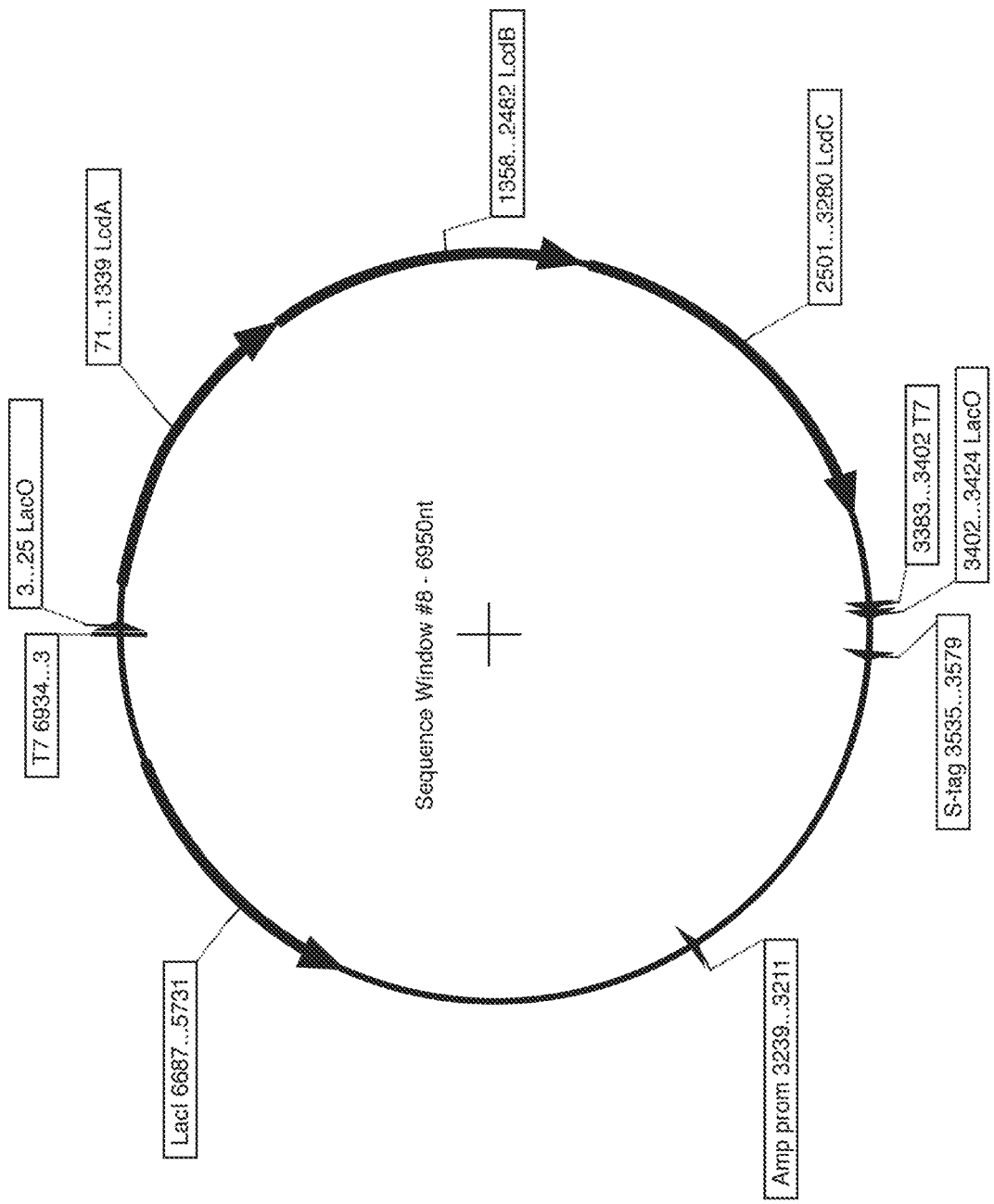
FIG. 24. Vector construct containing the gene encoding LcdABC from *Clostridium propionicum* for expression in *E. coli*. LcdABC is an example of 2-hydroxyacyl-CoA dehydratases (enzyme 3 in FIG. 10 and Table 2)
Figure 26:
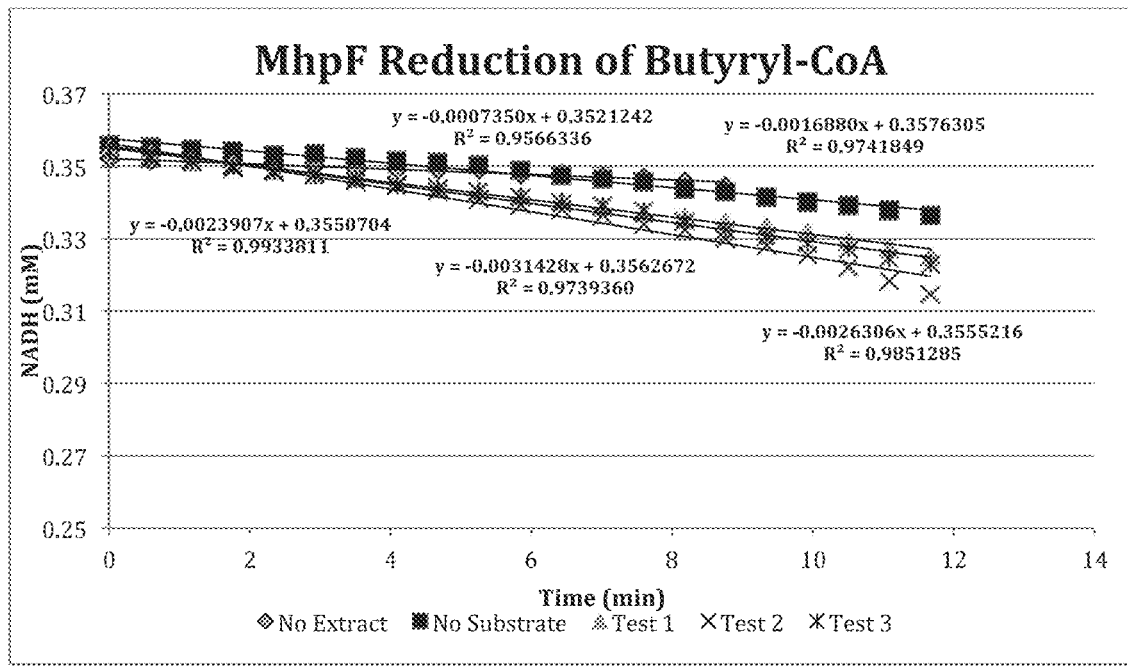
FIG. 26. Time course of absorbance at 340 nm corresponding to the consumption of NADH in the assay of MhpF.

The assay mixture consisted of 100 mM MOPS pH 7.5, 6 mM DTT, 5 mM $MgSO_4$, 0.3 mM $(NH_4)_2Fe(SO_4)_2$, 0.3 mM NADH, and 0.2 mM butyryl-CoA. The reaction was monitored by loss of absorbance at 340 nm corresponding to the consumption of NADH, as shown in FIG. 24. MhpF was capable of catalyzing the conversion with a specific activity of 0.009±0.003 µmol/min/mg protein (FIG. 26).

Figure 27:
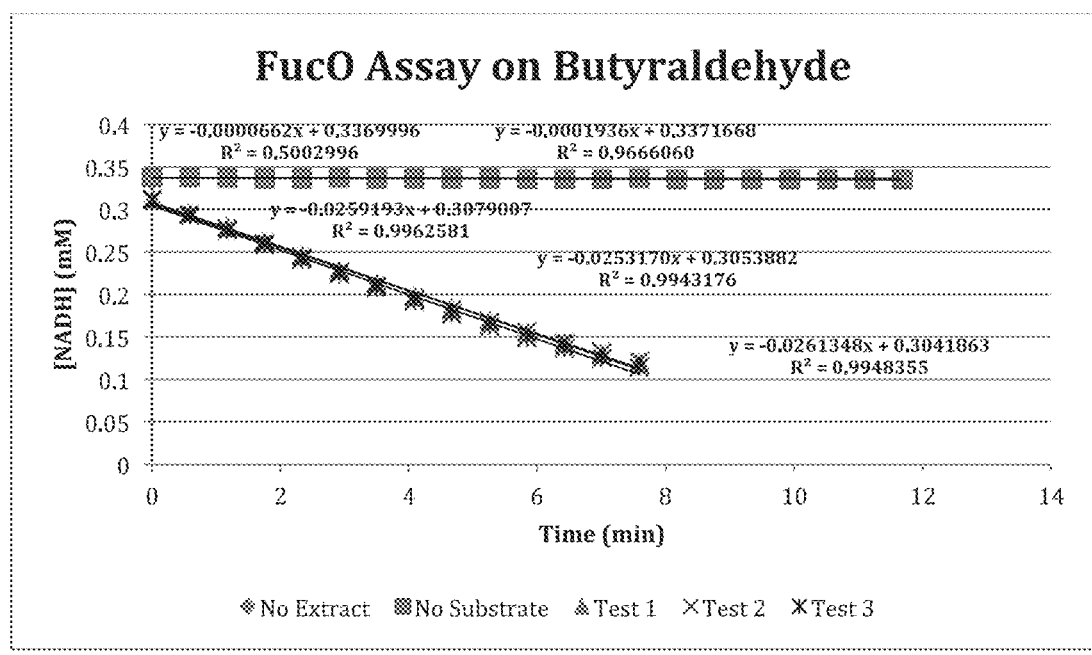
FIG. 27. Time course of absorbance at 340 nm corresponding to the consumption of NADH in the assay of FucO.

*E. coli* FucO was assayed for its ability to perform an analogous reaction, the reduction of butyraldehyde to butanol. FucO was expressed from an ASKA collection strain and purified as described above. Purified FucO was assayed in a buffer containing 100 mM Tris-HCl pH 7.5, 0.3 mM NADH, and 10 mM butyraldehyde. The reaction was monitored by loss of absorbance at 340 nm corresponding to the consumption of NADH, as shown in FIG. 27. FucO was capable of catalyzing the reduction of butyraldehyde to butanol with a specific activity of 5.08±0.08 µmol/min/mg protein.

Figure 28:
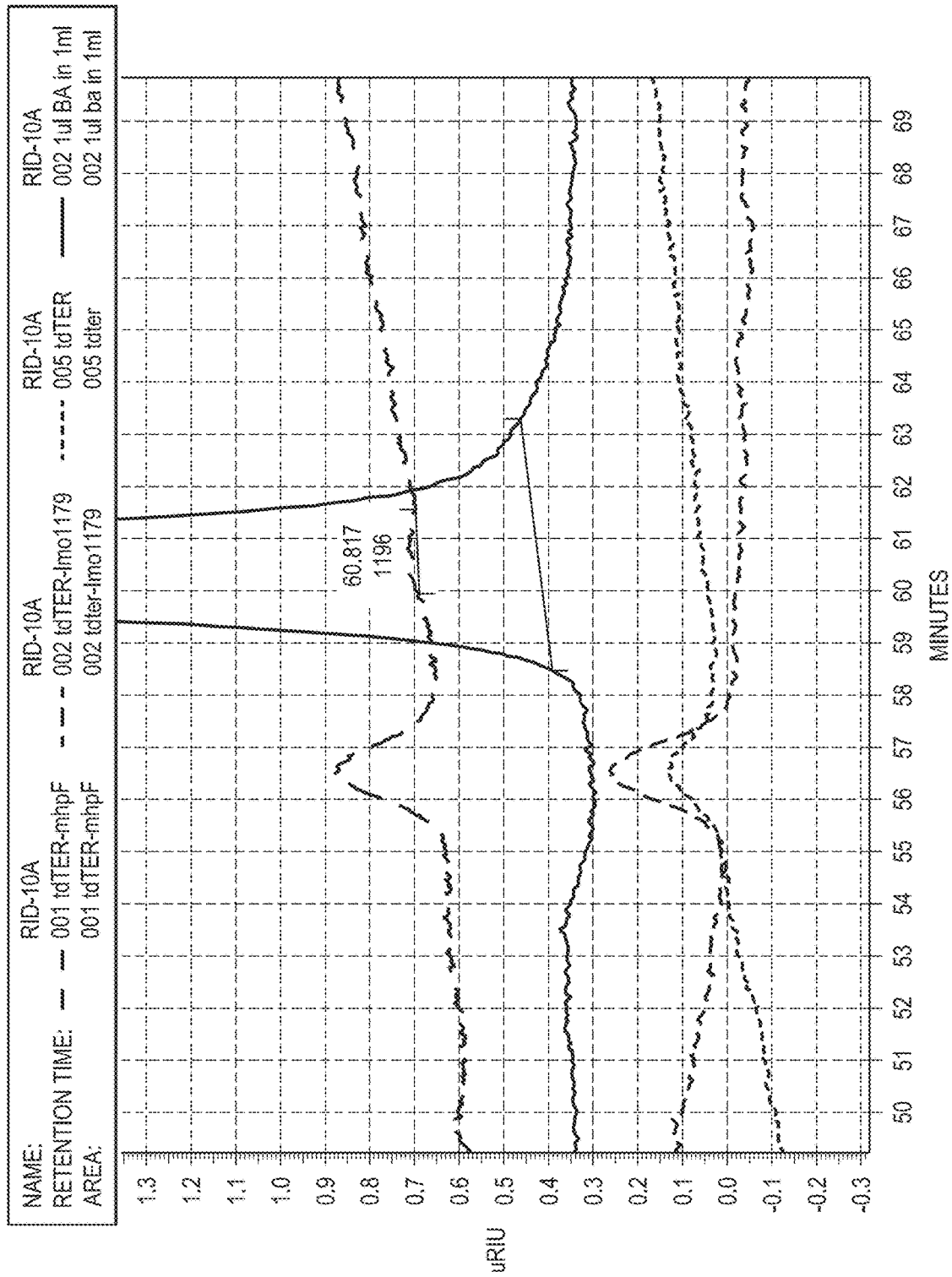
FIG. 28. HPLC chromatogram of the in vitro assembly of the trans-2-enoyl-CoA reductase and acyl-CoA reductase steps of the elongation module. A peak corresponding to butyraldehyde (butyraldehyde standard in bold) was present in samples containing *Treponema denticola* TER and *E. coli* MhpF (solid, thin line), but not the control containing *Treponema denticola* TER only (dashed line).

A portion of the elongation module was assembled in vitro to demonstrate the functionality of the combined pathway steps. The trans-2-enoyl-CoA reductase and acyl-CoA reductase steps were combined to assess the overall conversion of crotonyl-CoA to butyraldehyde. Experiments were carried out carried out in 50 mM Tris buffer, pH 7.5 containing 1 mM DTT at 37° C. The reaction with MhpF contained 0.15 g/L TdTer, 0.1 g/L of MhpF, 7.5 mM NADH and 1.7 mM crotonyl-CoA. Reaction with Lmo1179 contained 0.15 g/L TdTer, 0.9 g/L Lmo1179, 7.5 mM NADH and 1.7 mM crotonyl-CoA. The assay was monitored by measuring production of butyraldehyde with HPLC. When assayed under the conditions described above, the combination of trans-2-enoyl-CoA reductase from *Treponema denticola* and *E. coli* enzyme MhpF was shown to produce butyraldehyde from crotonyl-CoA to a final concentration of 0.55 mM (FIG. 28).

Regeneration module: Starting from the enoyl-CoA of the elongation module, an enoyl-CoA hydratase converts the enoyl-CoA to the corresponding 3-hydroxyacyl-CoA. The 3-hydroxyacyl-CoA is then converted to a 3-ketoacyl-CoA by a 3-hydroxyacyl-CoA dehydrogenase. A 3-ketoacyl-CoA thiolase cleaves the 3-ketoacyl-CoA into an acetyl-CoA and a two carbon shortened acyl-CoA. In this implementation, the acetyl-CoA is converted to an aldehyde by one of the aforementioned acyl-CoA reductases and is used to prime the elongation cycle in another round of the cycle. The remaining acyl-CoA is converted to a carboxylic acid product by a thioesterase or otherwise handled by the termination module.

Figure 29:
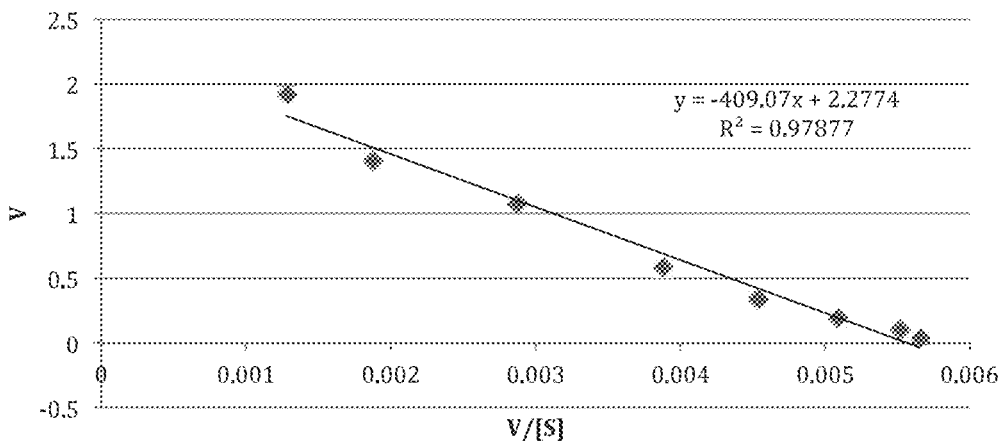
FIG. 29. Eadie-Hofstee plot for the determination of FadB enzyme kinetics.

Native *E. coli* FadB has been shown to have both enoyl-CoA hydratase and 3-hydroxyacyl-CoA dehydrogenase activity. *E. coli* FadB was purified and assayed in vitro in the opposite direction (FIG. 29), though its physiological activity in the desired direction has been well characterized (Binstock & Schulz, 1981). The β-hydroxybutyryl-CoA dehydrogenase assays were performed in the presence of 1.5 mM DTT, 4.5 mM MgCl$_2$, 100 mM Tris HCl pH 7.5 and 0.2 mM NADH in a total volume of 200 μL at 25° C. β-hydroxybutyryl-CoA dehydrogenase activity was monitored by following the oxidation of NADH at 340 nm. Enoyl-CoA hydratase activity was monitored by following the loss of crotonoyl-CoA at 263 nm (8=6.7 mM-1 cm-1) in the presence of 100 mM Tris HCL pH 7.5 in 200 μL total volume. In these conditions, enoyl-CoA hydratase specific activity was measured to be 0.051±0.004 μmol/min/mg protein, while 3-hydroxyacyl-CoA dehydrogenase activity was measured to be 0.185±0.001 μmol/min/mg protein (FIG. 29).

Figure 30:
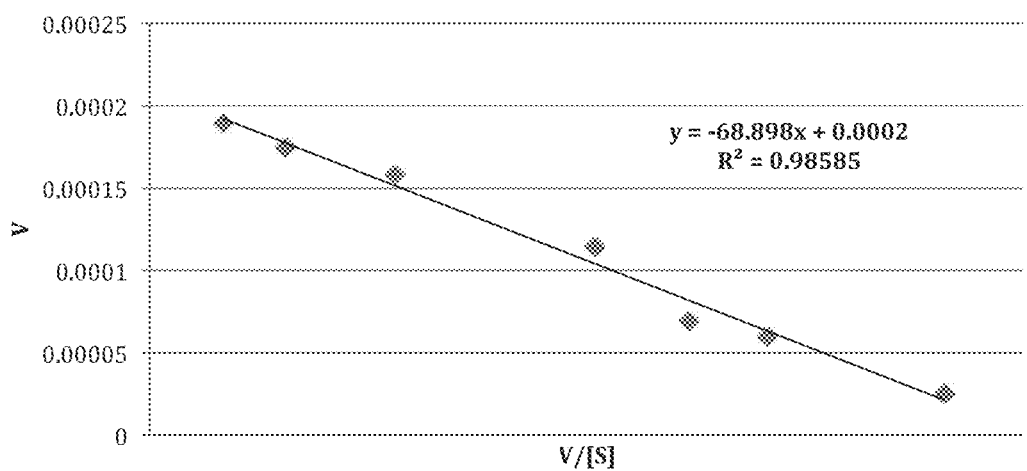
FIG. 30. Eadie-Hofstee plot for the determination of AtoB enzyme kinetics.

Native *E. coli* thiolases AtoB and FadA were assayed for their activity on cleaving 3-ketobutyryl-CoA to two molecules of acetyl-CoA (FIG. 30). Thiolase activity was determined in the presence of 0.5 mM DTT, 4.5 mM MgCl$_2$, 100 mM Tris HCl pH 7.5 and 2 mM CoA in a total volume of 200 UL at 25° C. The specific activities were measured as 0.36=0.05 μmol/min/mg protein for AtoB and 0.013±0.002 μmol/min/mg protein for FadA.

Figure 31:
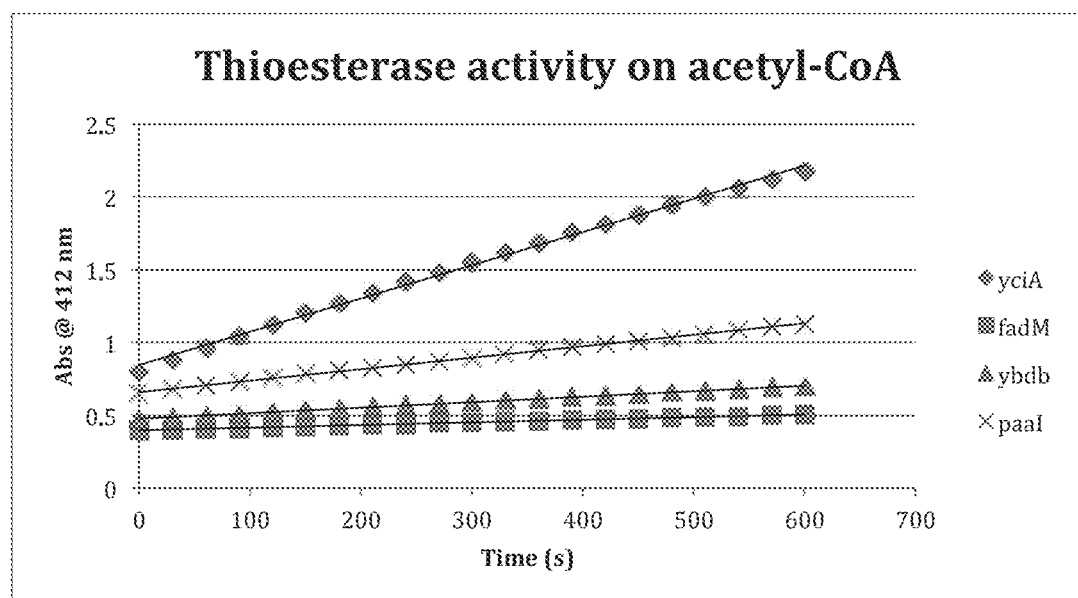
FIG. 31. Time course of absorbance at 412 nm corresponding to the production of TNB in the assay of the thioesterases: yciA, fadM, ydbB, and paaI.

Termination module: Native *E. coli* thioesterases FadM, TesA, TesB, YbgC, YciA, and YdiI were characterized in vitro by following the production of TNB at 412 nm (ε=4.3 mM$^{-1}$ cm$^{-1}$). Reactions were carried out in the presence of 100 mM Tris pH 7.5, 200 mM KCl, 25 mM DTNB and 200 UM of the '-CoA' substrate in a volume of 200 μL at 25° C. Due to their varying substrate chain length specificities, selection of the proper thioesterase for the desired product can be important to the optimal functionality of the pathway. The results of the in vitro characterization of the thioesterases on acetyl-CoA are summarized in Table 2 and in FIG. 31.

Figure 32:
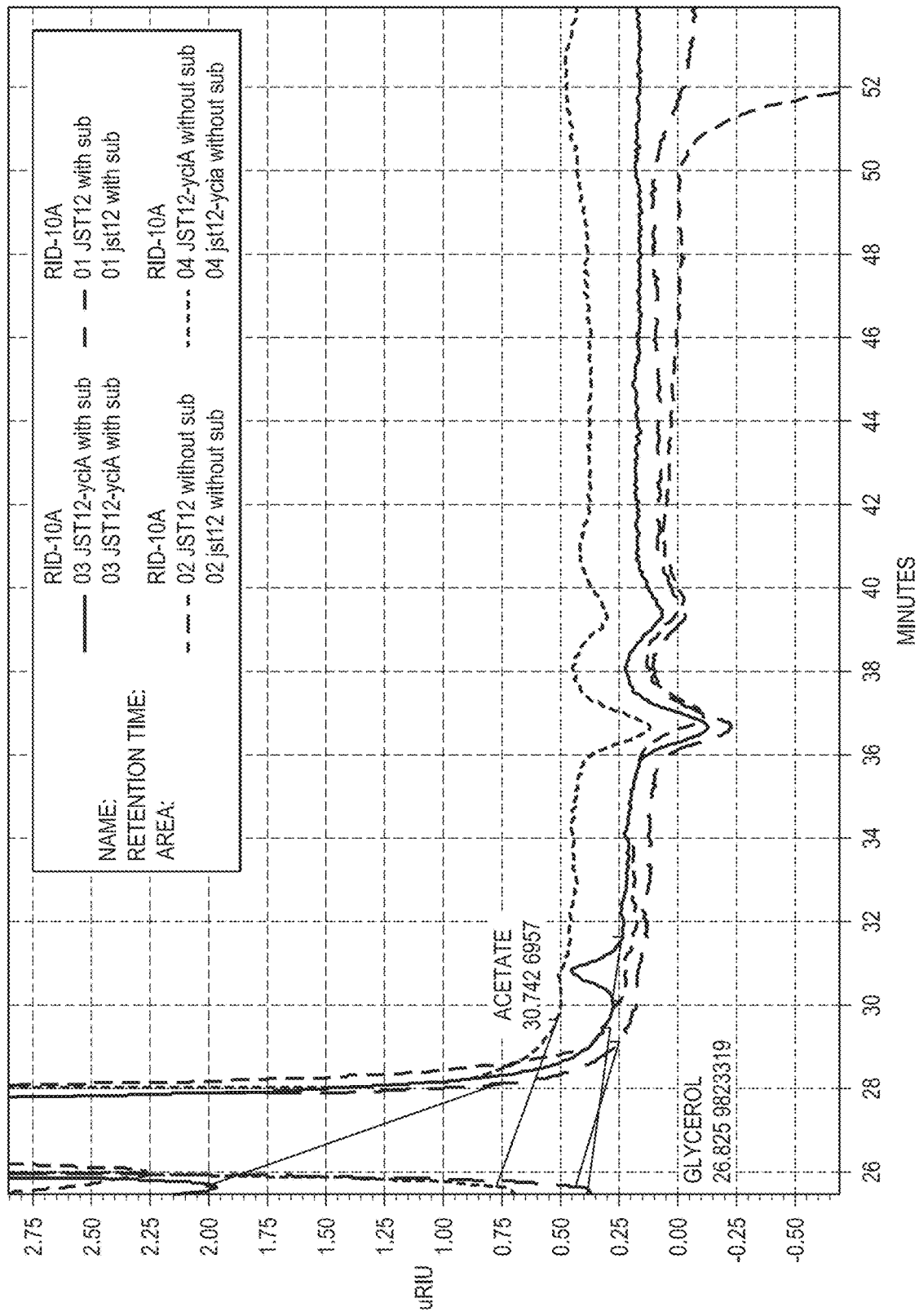
FIG. 32. HPLC chromatogram of assays of the combined regeneration and termination modules.

The regeneration and termination modules were assembled in vivo and crude extracts of cells expressing the module enzymes were assayed in vitro to demonstrate the functionality of the module. JST07, an *E. coli* MG1655 strain with native thioesterases knocked out, was used as a background from which AtoB and FadB, comprising the regeneration module, and YciA, comprising the termination module were overexpressed. With crotonyl-CoA as a substrate, this combination of regeneration and termination modules would be expected to produce acetate as a product. The reaction mixture contained 100 mM Tris-HCl (pH 7.5), 10 mM MgCl$_2$, 200 mM KCl, 1.7 mM crotonyl-CoA, 1 mM DTT, 3.5 mM NAD$^+$, 5 mM CoA and crude extract in a final volume of 300 μL. Reactions were carried out at 30° C. and generation of acetic acid was measured by HPLC. Assay mixture for acetic acid analysis was filtered through Amicon spin filters (molecular cutoff of 10 kDa) and stored at 4° C. prior to HPLC analysis. As shown in FIG. 32, acetate was observed in samples containing the entire regeneration and termination modules, but not in samples in which the termination module, YciA, was omitted. These results indicate the functional construction and expression of the combined regeneration and termination modules.

Figure 33:
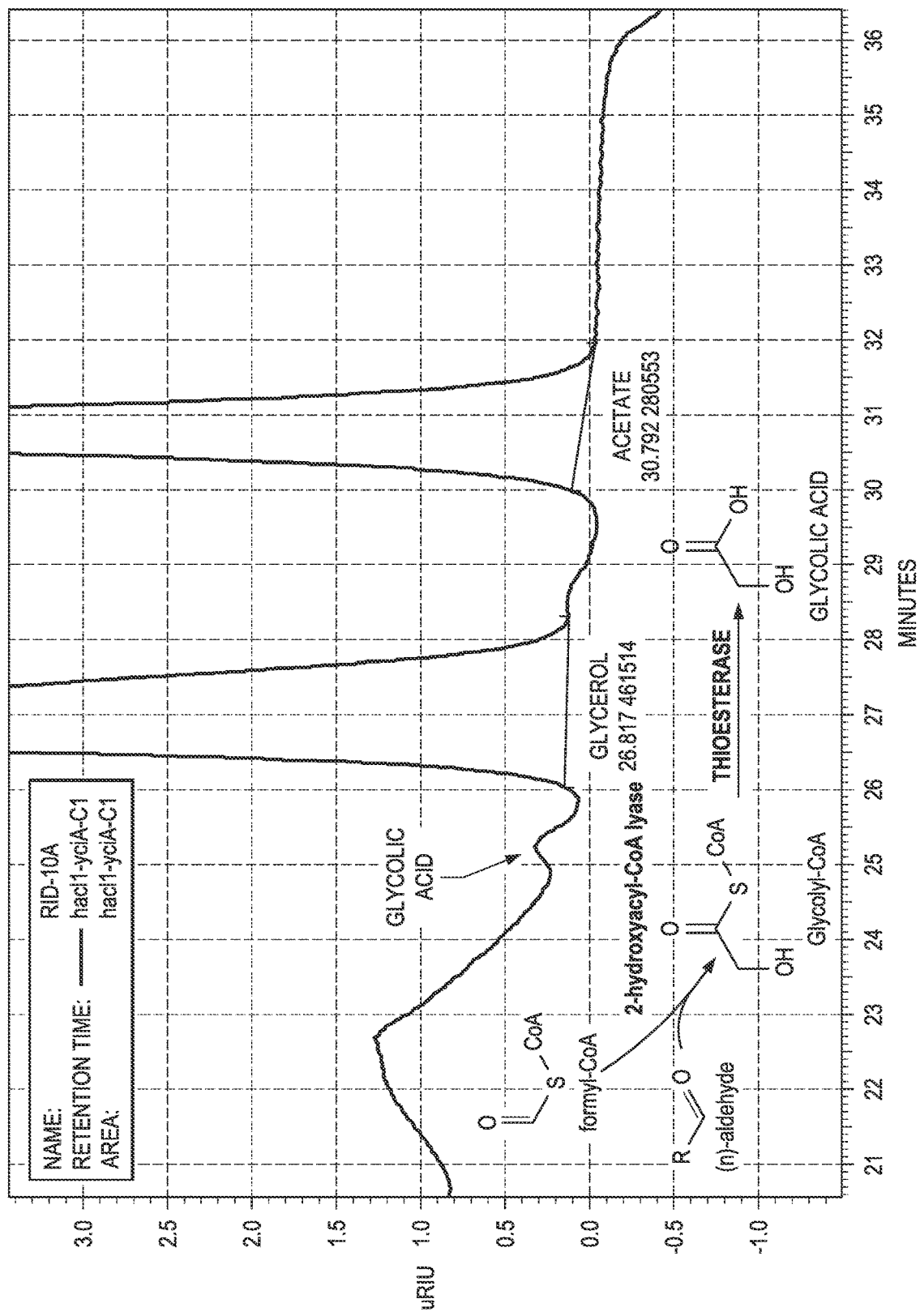
FIG. 33. HPLC chromatogram of an in vitro implementation of the pathway consisting of a one unit elongation catalyzed by HACL1, followed by direct termination to product. In this case, HACL1 catalyzed the ligation of formaldehyde and formyl-CoA to produce glycolyl-CoA. *E. coli* YciA included in the reaction mixture converted glycolyl-CoA to glycolic acid.

A simple implementation of the proposed pathway was implemented in vitro for the production of glycolic acid. In this implementation, formaldehyde was elongated by the one carbon unit formyl-CoA and the resulting 2-hydroxyacyl-CoA, glycolyl-CoA, was diverted to the termination module consisting of a thioesterase to give glycolic acid. In the in vitro implementation, HACL1 and *E. coli* YciA were combined in a reaction mixture comprised of 60 mM potassium phosphate pH 5.4, 2.5 mM MgCl$_2$, 0.1 mM TPP, 6.6 μM BSA, 5 mM aldehyde, and approximately 1 mM formyl-CoA. The mixture was incubated at room temperature for 30 minutes and analyzed directly by HPLC, which revealed the glycolic acid was produced by the pathway FIG. 33.

In Silico Pathway Modeling

A mathematical model of the pathway implemented in *E. coli* as a host was developed and evaluated to assess the feasibility of the pathway for supporting product formation and organism growth on various one-carbon feedstocks. The genome-scale model (GEM) iJO1366 for *E. coli* was used as starting point (Orth et al., 2011). This model includes 1366 genes, 2251 reactions, and 1136 unique metabolites. While adapting GEM iJO1366 to simulate the fermentative metabolism of glycerol by wild-type *E. coli* in minimal medium, this model predicted operation of a number of pathways that are not functional under the simulated conditions but that artificially enabled redox balance. Consequently, we restricted the reactions involved exclusively in amino acid degradation, nucleotide degradation and export of amino acids, spermidine, 5-methylthio-d-ribose production, ferrous and hydrogen sulfide to zero flux (Cintolesi, et al., 2014). The reactions comprising the proposed pathway were then added to the GEM.

For simplification, the net reaction for a two-turn elongation cycle was used to give production of acetyl-CoA, which in turn allows for cell growth. This net reaction can be written:

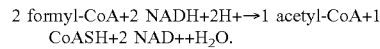
2 formyl-CoA+2 NADH+2H+→1 acetyl-CoA+1 CoASH+2 NAD++H$_2$O.

In addition, reactions for the conversion of different single carbon substrates to formyl-CoA were added to the model. For formaldehyde the reaction took the form:

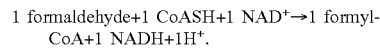
1 formaldehyde+1 CoASH+1 NAD$^+$→1 formyl-CoA+1 NADH+1H$^+$.

For formic acid, the reaction was written:

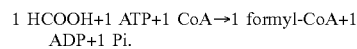
1 HCOOH+1 ATP+1 CoA→1 formyl-CoA+1 ADP+1 Pi.

In addition, the conversion of CO$_2$ and hydrogen to formic acid by CO$_2$ reductase (Schuchmann & Müller, 2013) was written:

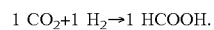
1 CO$_2$+1 H$_2$→1 HCOOH.

Conversion of methanol to formaldehyde was written:

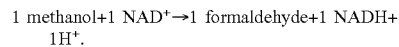
1 methanol+1 NAD$^+$→1 formaldehyde+1 NADH+1H$^+$.

Conversion of methane to methanol by methane monooxygenases was written:

1 methane+1 O$_2$+1 NADH+1H+→1 methanol+1 NAD$^+$+H$_2$O.

Flux balance analysis was used to evaluate the model. The evaluation was done using COBRA toolbox v2.0 (Schellenberger et al., 2011) in Matlab (THE MATHWORKS, MA). For comparison, the uptakes of the one carbon substrates were set equal on a carbon mole basis (arbitrarily, 10 mmol C/g DCW/hr).

Figure 34:
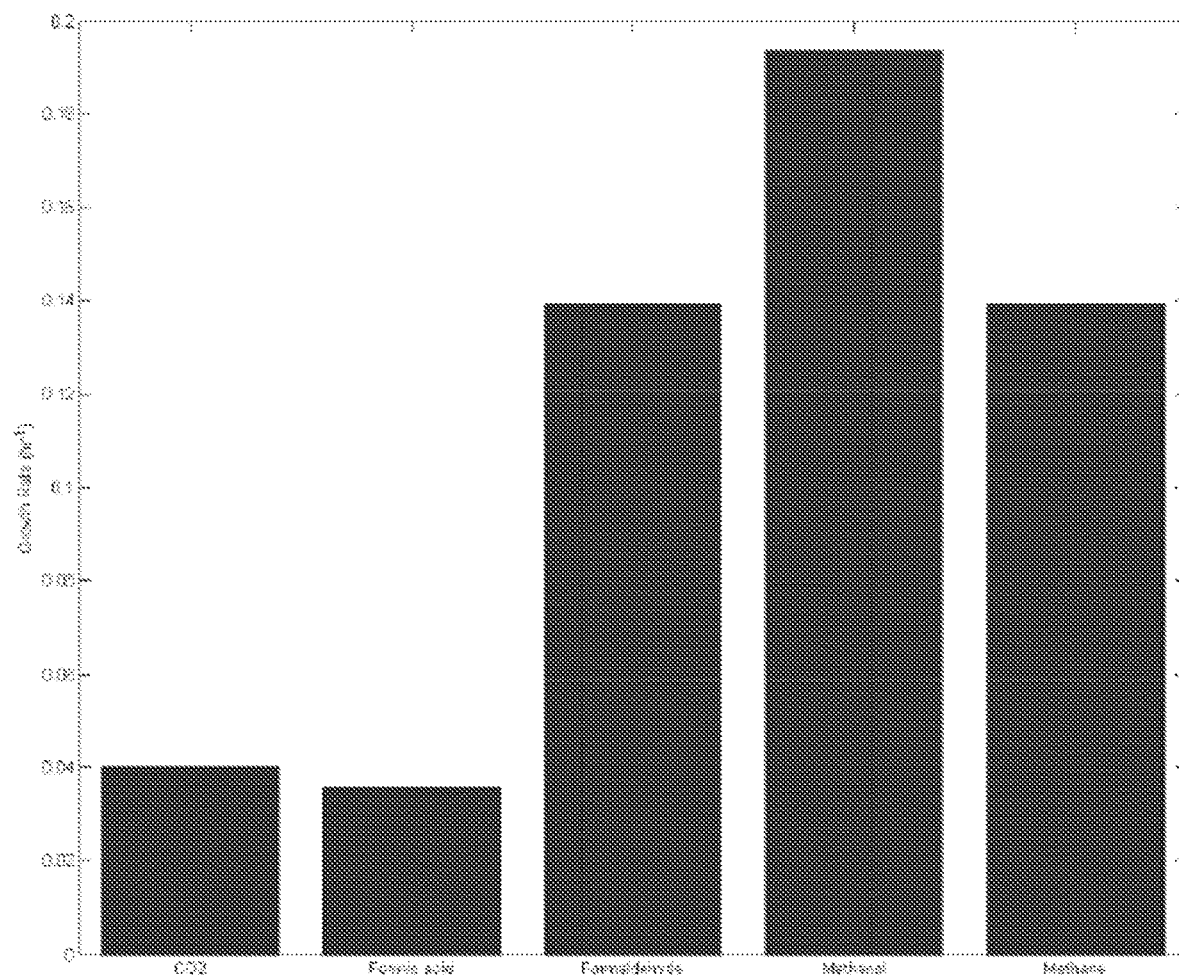
FIG. 34. Comparison of the ability of the engineered pathway to support growth of *E. coli* on different single carbon feedstocks as evaluated by a genome scale model.

The ability for the pathway to support cell growth by the production of acetyl-CoA was then modeled. Because *E. coli* cannot natively grow on single carbon substrates, cell growth as a result of the inclusion of the pathway in the *E. coli* model indicates a functional pathway. Indeed, the results indicated that *E. coli* containing the designed pathway was able to grow on single carbon substrates ranging from CO$_2$ to methane (FIG. 34). Methanol appeared to allow for the highest growth rate, most likely due to the additional reducing equivalent obtained from methanol oxidation, which can be used to produce ATP for growth. Growth on formate and $CO_2$ was more challenging compared to the other substrates due to the ATP requirement of their conversion to formyl-CoA and because of their high oxidation state. This is a proof of principle demonstration that the pathway is capable of functioning as designed in the context of *E. coli* metabolism, as well as the metabolism of other organisms.

TABLE 1A

Summary of pathway reactions and enzymes

| Reaction | Illustration | EC Numbers | Enzyme names | Source organism and gene name | Protein Accession Numbers |
|---|---|---|---|---|---|
| | | Extender Generation Module | | | |
| Carbon dioxide → Formate | 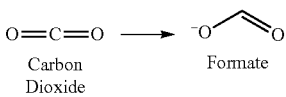 | 1.2.1.2 | Carbon dioxide reductase | *Acetobacterium woodii* fdhF2, hycB2, hycB3, hydA2 | YP_005268502.1, YP_005268503.1, YP_005268505.1, YP_005268506.1 |
| Formate → Formyl-Phosphate | 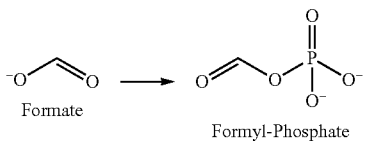 | 2.7.2.6 | Formate kinase | *Salmonella typhimurium* stAckA *E. coli* AckA | P63411 NP_416799.1 |
| Formyl-Phosphate → Formyl-CoA | 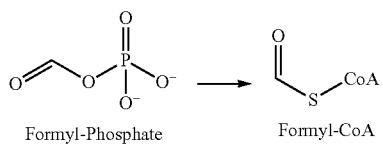 | 2.3.1.8 | Phosphate formyl-transferase | *E. coli* eutD *E. coli* pta *Salmonella typhimurium* PduL | NP_416953.1 NP_416800.1 Q9XDN5 |
| Formate → Formyl-CoA | 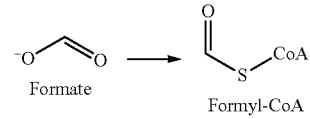 | 6.2.1.— | Acetyl-CoA synthetase | *E. coli* acs | NP_418493.1 |
| Methane → Methanol | 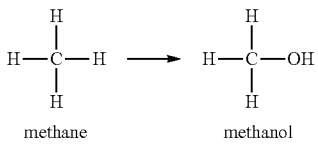 | 1.14.13.25; 1.14.18.3 | Methane monooxygenase | *Methylosinus trichosporium* OB3b mmoXYZBC, orfY *Methylococcus capsulatus* Bath mmoXYZBC, orfY | P27353, P27354, P27355, Q53563, P27356, Q53562 P22869, P18798, P11987, P18797, P22868, P22867 |
| Methanol → Formaldehyde | 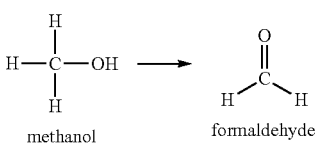 [SMILES: CO ; C=O] | 1.1.1.244; 1.1.2.7; 1.1.99.37 | Methanol dehydrogenase | *Bacillus methanolicus* mdh *Mycobacterium* sp. DSM 3803 mdo *Methylobacterium extorquens* moxI, moxF | P31005 C5MRT8 P14775, P16027 |
| Formaldehyde → Formyl-CoA | 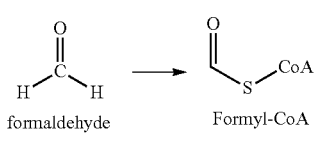 | 1.2.1.10 | Acylating aldehyde dehydrogenase | *E. coli* mhpF *Pseudomonas* sp. CF600 dmpF | NP_414885.1 Q52060 |

TABLE 1B

Summary of pathway reactions and enzymes

Elongation Module

| Reaction | Illustration | EC Numbers | Enzyme names | Source organism and gene name | Protein Accession Numbers |
|---|---|---|---|---|---|
| Formyl-CoA + C(n)-aldehyde → 2-hydroxy-C(n + 1)-acyl-CoA | C(n)-aldehyde + formyl-CoA → 2-hydroxy-C(n + 1)-acyl-CoA | 4.1.—.— | 2-hydroxyacyl-CoA lyase | *Homo sapiens* hacl1 | Q9UJ83 |
| | | | | *Rattus norvegicus* hacl1 | Q8CHM7 |
| | | | | *Dictyostelium discoideum* hacl1 | Q54DA9 |
| | | | | *Mus musculus* hacl1 | Q9QXE0 |
| | | | Oxalyl-CoA decarboxylase | *Mycobacterium* sp. MOTT36Y W7S_25140 | YP_006308704.1 |
| | | | | *Mycobacterium tuberculosis* TKK-01-0051 K875_00487 | KBZ67942.1 |
| | | | | *Polynucleobacter necessarius* subsp. *asymbioticus* QLW-P1DMWA-1 Pnuc_0637 | YP_001155419.1 |
| | | | | *E. coli* oxc | NP_416874.1 |
| 2-hydroxy-C(n + 1)-acyl-CoA → Trans-2-C(n + 1)-enoyl-CoA | 2-hydroxy-C(n + 1)-acyl-CoA → trans-2-C(n + 1)-enoyl-CoA | 4.2.1.54 | 2-hydroxyacyl-CoA dehydratase | *Clostridium propionicum* IcdABC | G3KIM3, G3KIM4, G3KIM5 |
| | | | | *Clostridium difficile* hadBCI | AAV40818.1, AAV40819.1, AAV40820.1 |
| Trans-2-C(n + 1)-enoyl-CoA → C(n + 1)-acyl-CoA | trans-2-C(n + 1)-enoyl-CoA → C(n + 1)-acyl-CoA | 1.3.1.38; 1.3.1.44 | Trans-2-enoyl-CoA reductase | *E. coli* yhdH | NP_417719.1 |
| | | | | *E. coli* fabI | NP_415804.1 |
| | | | | *Enterococcus faecalis* fabK | NP_816503.1 |
| | | | | *Bacillus subtilis* fabL | KFK80655.1 |
| | | | | *Euglena gracilis* egTER | Q5EU90.1 |
| | | | | *Treponema denticola* tdTER | NP_971211.1 |
| | | | | *Vibrio cholera* fabV | B1P0R8 |
| C(n + 1)-acyl-CoA → C(n + 1)-aldehyde | C(n + 1)-acyl-CoA → C(n + 1)-aldehyde | 1.2.1.— | Acyl-CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| 2-hydroxy-C(n + 1)-acyl-CoA → 2-hydroxy-C(n + 1)-aldehyde | 2-hydroxy-C(n+1)-acyl-CoA → 2-hydroxy-C(n+1)-aldehyde | | | *E. coli* eutE | NP_416950.1 |
| | | | | *Salmonella enterica* eutE | AAA80209.1 |
| | | | | *E. coli* mhpF | NP_414885.1 |
| 2-hydroxy-C(n + 1)-aldehyde → 1,2-C(n + 1)-diol | 2-hydroxy-C(n + 1)-aldehyde → 1,2-C(n + 1)-diol | 1.1.1.77 | 1,2-diol oxidoreductase | *E. coli* fucO | NP_417279.1 |
| | | | | *E. coli* betA | NP_414845.1 |
| | | | | *E. coli* dkgA | NP_417485.4 |
| | | | | *E. coli* eutG | NP_416948.4 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |

TABLE 1B-continued

Summary of pathway reactions and enzymes

Elongation Module

| Reaction | Illustration | EC Numbers | Enzyme names | Source organism and gene name | Protein Accession Numbers |
|---|---|---|---|---|---|
| 1,2-C(n + 1)-diol → C(n + 1)-aldehyde | 1,2-C(n + 1)-diol → C(n +1)-aldehyde | 4.2.1.28 | Diol dehydratase | *Klebsiella ocytoca* pddABC | Q59470, Q59471, Q59472 |
| | | | | *E. coli* pduCDE | CAS09680, CAS09681, CAS09682 |
| | | | | *S. enterica* pduCDE | NP_456590, NP_456591, NP_456592 |

TABLE 1C

Summary of pathway reactions and enzymes

Regeneration module

| Reaction | Illustration | EC Numbers | Enzyme names | Source organism and gene name | Protein Accession Numbers |
|---|---|---|---|---|---|
| Trans-2-C(n + m)-enoyl-CoA → 3-hydroxy-C(n + m)-acyl-CoA | trans-2-C(n + m)-enoyl-CoA → 3-hydroxy-C(n + m)-acyl-CoA | 4.2.1.17; 4.2.1.119; 4.2.1.150 | Enoyl-CoA hydratase | *E. coli* fadB | NP_418288.1 |
| | | | | *E. coli* fadJ | NP_416843.1 |
| | | | | *Aeromonas caviae* phaJ | O32472.1 |
| | | | | *Pseudomonas aeruginosa* phaJ1 | BAA92740.1 |
| | | | | *Pseudomonas aeruginosa* phaJ2 | BAA92741.1 |
| | | | | *Pseudomonas aeruginosa* phaJ3 | BAC44834.1 |
| | | | | *Pseudomonas aeruginosa* phaJ4 | BAC44835.1 |
| 3-hydroxy-C(n + m)-acyl-CoA → 3-keto-C(n + m)-acyl-CoA | 3-hydroxy-C(n + m)-acyl-CoA → 3-keto-C(n + m)-acyl-CoA | 1.1.1.35; 1.1.1.36; 1.1.1.211 | 3-hydroxyacyl-CoA dehydrogenase | *E. coli* fadB | NP_418288.1 |
| | | | | *E. coli* fadJ | NP_416843.1 |
| | | | | *Ralstonia eutropha* phaB1 | YP_725942.1 |
| | | | | *Ralstonia eutropha* phaB2 | YP_726470.1 |
| | | | | *Ralstonia eutropha* phaB3 | YP_726636.1 |
| 3-keto-C(n + m)-acyl-CoA → Acetyl-CoA + C(n + m − 2)- | 3-keto-C(n + m)-acyl-CoA | 2.3.1.16 | 3-ketoacyl-CoA thiolase | *E. coli* atoB | NP_416728.1 |
| | | | | *E. coli* yqeF | NP_417321.2 |
| | | | | *E. coli* fadA | YP_026272.1 |
| | | | | *E. coli* fadI | NP_416844.1 |
| | | | | *Ralstonia eutropha* bktB | AAC38322.1 |
| | | | | *Pseudomonas* | AAL02407.1 |

TABLE 1C-continued

Summary of pathway reactions and enzymes

Regeneration module

| Reaction | Illustration | EC Numbers | Enzyme names | Source organism and gene name | Protein Accession Numbers |
|---|---|---|---|---|---|
| acyl-CoA | 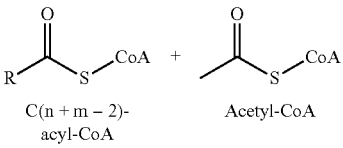 C(n+m−2)-acyl-CoA + Acetyl-CoA | | | sp. Strain B13 catF | |
| | | | | *E coli* paaJ | NP_415915.1 |
| | | | | *Rhodococcus opacus* pcaF | YP_002778248.1 |
| | | | | *Streptomyces* sp. pcaF | AAD22035.1 |
| | | | | *Ralstonia eutropha* phaA | AEI80291.1 |
| | | | | *Clostridium acetobutylicum* thlA | AAC26023.1 |
| | | | | *Clostridium acetobutylicum* thlB | AAC26026.1 |
| Acetyl-CoA → Acetaldehyde | 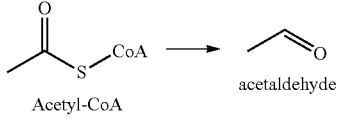 Acetyl-CoA → acetaldehyde | 1.2.1.10 | Acetyl-CoA reductase | *E. coli* eutE | NP_416950.1 |
| | | | | *Salmonella enterica* eutE | AAA80209.1 |
| | | | | *E. coli* mhpF | NP_414885.1 |

TABLE 1D

Summary of pathway reactions and enzymes

Termination module

| Reaction | Illustration | EC Numbers | Enzyme names | Source organism and gene name | Protein Accession Numbers |
|---|---|---|---|---|---|
| Acyl-CoA → Carboxylic acid | 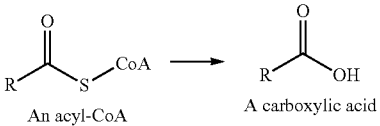 An acyl-CoA → A carboxylic acid | 3.1.2.— | Thioesterase | *E. coli* tesA | NP_415027.1 |
| | | | | *E. coli* tesB | NP_414986.1 |
| | | | | *E. coli* yciA | NP_415769.1 |
| | | | | *E. coli* fadM | NP_414977.1 |
| | | | | *E. coli* ydiI | NP_416201.1 |
| | | | | *E. coli* ybgC | NP_415264.1 |
| | | | | *Alcanivorax borkumensis* tesB2 | YP_692749.1 |
| | | | | *Fibrobacter succinogenes* Fs2108 | YP_005822012.1 |
| | | | | *Prevotella ruminicola* Pr655 | YP_003574018.1 |
| | | | | *Prevotella ruminicola* Pr1687 | YP_003574982.1 |
| | | 2.8.3.8 | Acyl-CoA: acetyl-CoA transferase | *E. coli* atoD | NP_416725.1 |
| | | | | *Clostridium kluyveri* cat2 | AAA92344.1 |
| | | | | *Clostridium acetobutylicum* ctfAB | NP_149326.1, NP_149327.1 |
| | | | | *E. coli* ydiF | NP_416209.1 |
| | | 2.3.1.—; 2.7.2.1; 2.7.2.15 | Phospho-transacylase + Carboxylate kinase | *Clostridium acetobutylicum* ptb | NP_349676.1 |
| | | | | *Enterococcus faecalis* ptb | AAD55374.1 |
| | | | | *Salmonella enterica* pduL | AAD39011.1 |
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |

TABLE 1D-continued

Summary of pathway reactions and enzymes

Termination module

| Reaction | Illustration | EC Numbers | Enzyme names | Source organism and gene name | Protein Accession Numbers |
|---|---|---|---|---|---|
| Acyl-CoA → Alcohol | 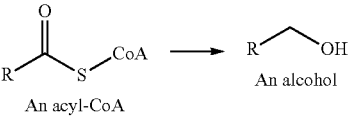 | 1.2.1.84 | Alcohol-forming coenzyme-A thioester reductase | Clostridium acetobutylicum adhE2 | YP_009076789.1 |
| | | | | Arabidopsis thaliana At3g11980 | AEE75132.1 |
| | | | | Arabidopsis thaliana At3g44560 | AEE77915.1 |
| | | | | Arabidopsis thaliana At3g56700 | AEE79553.1 |
| | | | | Arabidopsis thaliana At5g22500 | AED93034.1 |
| | | | | Arabidopsis thaliana CER4 | AEE86278.1 |
| | | | | Marinobacter aquaeolei VT8 maqu_2220 | YP_959486.1 |
| | | | | Marinobacter aquaeolei VT8 maqu_2507 | YP_959769.1 |
| Acyl-CoA → Aldehyde | 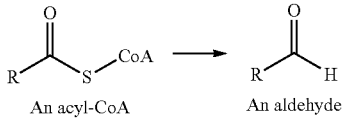 | 1.2.1.10 | Aldehyde forming CoA thioester reductase | Acinetobacter calcoaceticus acr1 | AAC45217.1 |
| | | | | Acinetobacter sp Strain M-1 acrM | BAB85476.1 |
| | | | | Clostridium beijerinckii ald | AAT66436.1 |
| | | | | E. coli eutE | NP_416950.1 |
| | | | | Salmonella enterica eutE | AAA80209.1 |
| | | | | E. coli mhpF | NP_414885.1 |
| Aldehyde → Alcohol | 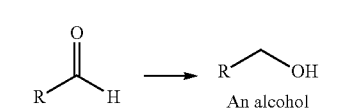 | 1.1.1.— | Alcohol dehydrogenase | E. coli betA | NP_414845.1 |
| | | | | E. coli dkgA | NP_417485.4 |
| | | | | E. coli eutG | NP_416948.4 |
| | | | | E. coli fucO | NP_417279.2 |
| | | | | E. coli ucpA | NP_416921.4 |
| | | | | E. coli yahK | NP_414859.1 |
| | | | | E. coli ybbO | NP_415026.1 |
| | | | | E. coli ybdH | NP_415132.1 |
| | | | | E. coli yiaY | YP_026233.1 |
| | | | | E. coli yjgB | NP_418690.4 |
| Aldehyde → Alkane |  | 4.1.99.5 | Aldehyde decarbonylase | Synechococcus elongatus PCC7942 orf1593 | Q54764.1 |
| | | | | Nostoc punctiforme PCC73102 npun_R1711 | B2J1M1.1 |
| | | | | Prochlorococcus marinus MIT9313 pmt1231 | Q7V6D4.1 |
| Aldehyde → Amine | 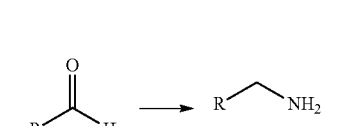 | | Transaminase | Arabidopsis thaliana At3g22200 | NP_001189947.1 |
| | | | | Alcaligenes denitrificans AptA | AAP92672.1 |
| | | | | Bordetella bronchiseptica BB0869 | WP_015041039.1 |
| | | | | Bordetella parapertussis BPP0784 | WP_010927683.1 |
| | | | | Brucella melitensis BAWG_0478 | EEW88370.1 |
| | | | | Burkholderia pseudomallei BP1026B_I0669 | AFI65333.1 |
| | | | | Chromobacterium violaceum CV2025 | AAQ59697.1 |
| | | | | Oceanicola granulosus OG2516_07293 | WP_007254984.1 |

TABLE 1D-continued

Summary of pathway reactions and enzymes

| Reaction | Illustration | EC Numbers | Enzyme names | Source organism and gene name | Protein Accession Numbers |
|---|---|---|---|---|---|
| Termination module | | | | | |
| | | | | *Paracoccus denitrificans* PD1222 Pden_3984 | ABL72050.1 |
| | | | | *Pseudogulbenkiania ferrooxidans* □-TA | WP_008952788.1 |
| | | | | *Pseudomonas putida* □-TA | P28269.1 |
| | | | | *Ralstonia solanacearum* □-TA | YP_002258353.1 |
| | | | | *Rhizobium meliloti* SMc01534 | NP_386510.1 |
| | | | | *Vibrio fluvialis* □-TA | AEA39183.1 |
| | | | | *Mus musculus* abaT | AAH58521.1 |
| | | | | *E. coli* gabT | YP_490877.1 |

The following references are incorporated by reference in their entirety herein for all purposes.

U.S. Ser. No. 61/440,192, filed Feb. 7, 2011.
U.S. Ser. No. 61/531,911, filed Sep. 7, 2011.
PCT/US12/24051, filed Feb. 7, 2012.
US20130316413, US20140273110.
Binstock, J. F., & Schulz, H. (1981). Fatty acid oxidation complex from *Escherichia coli*. *Methods in Enzymology*, 71 Pt C: 403-411.
Blecher, M. (1981). Synthesis of long-chain fatty acyl-CoA thioesters using N-hydroxysuccinimide esters. *Methods in Enzymology*, 72:404-408.
Cintolesi, A., Clomburg, J. M., & Gonzalez, R. (2014). In silico assessment of the metabolic capabilities of an engineered functional reversal of the β-oxidation cycle for the synthesis of longer-chain (C≥4) products. *Metabolic Engineering*, 23:100-15.
Datsenko, K. a, & Wanner, B. L. (2000). One-step inactivation of chromosomal genes in *Escherichia coli* K-12 using PCR products. *Proceedings of the National Academy of Sciences of the United States of America*, 97 (12): 6640-5. http://doi.org/10.1073/pnas.120163297
Hofmeister, A., & Buckel, W. (1992). (R)-Lactyl-CoA dehydratase from *Clostridium propionicum*. *European Journal of Biochem*. 206 (2): 547-552.
Kitagawa, M., et al., (2005). Complete set of ORF clones of *Escherichia coli* ASKA library (a complete set of *E. coli* K-12 ORF archive): unique resources for biological research. *DNA Research: An International Journal for Rapid Publication of Reports on Genes and Genomes*, 12 (5): 291-9.
Neidhardt, F. C., Bloch, P. L., & Smith, D. F. (1974). Culture Medium for Enterobacteria. *Journal Of Bacteriology*, 119 (3): 736-747. Retrieved from http://www.pubmedcentral.nih.gov/articlerender.fcgi?artid=245675&tool=pmcentrez&rendertype=abstract
Orth, J. D. et al., (2011). A comprehensive genome-scale reconstruction of *Escherichia coli* metabolism, *Molecular Systems Biology*, 7:535.
Parasaran, T., & Tarbell, D. S. (1964). Formic Ethylcarbonic Anhydride. *The Journal of Organic Chemistry*, 29 (11): 3422-3423. http://doi.org/10.1021/jo01034a516Schellenberger, J. et al. (2011).
Quantitative prediction of cellular metabolism with constraint-based models: the COBRA Toolbox v2.0. Nat. Protoc. 6, 1290-307.
Schuchmann, K., & Müller, V. (2013). Direct and reversible hydrogenation of CO2 to formate by a bacterial carbon dioxide reductase. *Science* (New York, N.Y.), 342 (6164): 1382-5.
Tatusova TA & Madden TL (1999). BLAST 2 Sequences, a new tool for comparing protein and nucleotide sequences. *FEMS Microbiol. Lett.* 174:247-250.
Tobimatsu, T., Sakai, T., Hashida, Y., Mizoguchi, N., Miyoshi, S., & Toraya, T. (1997). Heterologous Expression, Purification, and Properties of Diol Dehydratase, an Adenosylcobalamin-Dependent Enzyme of *Klebsiella oxytoca*. Archives of Biochemistry and Biophysics, 347 (1): 132-140.
Zhu, H., Gonzalez, R., & Bobik, T. a. (2011). Coproduction of acetaldehyde and hydrogen during glucose fermentation by *Escherichia coli*. *Applied and Environmental Microbiology*, 77 (18): 6441-50. http://doi.org/10.1128/AEM.05358-11

The invention claimed is:

1. A method for the production of a product from a single carbon substrate, the method comprising the steps of:
   a) growing a genetically modified microorganism in a culture comprising the single carbon substrate and a growth media,
   b) converting said single carbon substrate to a formyl-CoA,
   c) condensing an initial C(n)-aldehyde with the formyl-CoA to produce 2-hydroxy-C(n+1)-acyl-CoA, wherein the 2-hydroxy-C(n+1)-acyl-CoA is one carbon longer than the initial C(n) aldehyde and wherein n is the number of carbons in the initial C(n)-aldehyde;
   d) converting the 2-hydroxy-C(n+1)-acyl-CoA to a C(n+1)-aldehyde;
   e) isolating a product from said microorganism, or said growth media, or both;
   wherein the single carbon substrate is selected from the group consisting of methane, methanol, formaldehyde, formate, carbon monoxide, carbon dioxide, and combinations thereof; and
   wherein the microorganism expresses:
      i. a 2-hydroxyacyl-CoA lyase or an oxalyl-CoA decarboxylase that catalyzes the condensation of the initial C(n)-aldehyde with the formyl-CoA to produce the 2-hydroxy-C(n+1)-acyl-CoA;
      ii. one or more polypeptides that catalyze the conversion of the single carbon substrate to the formyl-CoA; and
      iii. one or more polypeptides that catalyze a conversion of the 2-hydroxy-C(n+1)-acyl-CoA to the C(n+1)-aldehyde.

2. The method of claim 1, wherein the microorganism expresses a 2-hydroxyacyl-CoA lyase.

3. The method of claim 1, wherein the 2-hydroxyacyl-CoA lyase is encoded by a DNA molecule selected from *Homo sapiens* hacl1, *Rattus norvegicus* hacl1, *Dictyostelium discoideum* hacl1, and *Mus musculus* hacl1, and the oxalyl-CoA decarboxylase is encoded by a DNA molecule selected from *Mycobacterium* sp. MOTT36Y W7S_25140, *Mycobacterium tuberculosis* TKK-01-0051 K875_00487, *Polynucleobacter necessarius* subsp. asymbioticus QLW-P1DMWA-1 Pnuc_0637, and *E. coli* oxc.

4. The method of claim 3, wherein the 2-hydroxyacyl-CoA lyase is encoded by *Homo sapiens* hacl1.

5. The method of claim 1, wherein the conversion of the 2-hydroxy-C(n+1)-acyl-CoA to the C(n+1)-aldehyde comprises the steps of:
   i. conversion of the 2-hydroxy-C(n+1)-acyl-CoA to a 2-hydroxy-C(n+1)-aldehyde;
   ii. conversion of the 2-hydroxy-C(n+1)-aldehyde to a 1,2-C(n+1)-diol; and
   iii. conversion of the 1,2-C(n+1)-diol to the C(n+1)-aldehyde.

6. The method of claim 5, wherein the one or more polypeptides that catalyzes the conversion of the 2-hydroxy-C(n+1)-acyl-CoA to the C(n+1)-aldehyde comprises:
   an acyl-CoA reductase that catalyzes the conversion of the 2-hydroxy-C(n+1)-acyl-CoA to the 2-hydroxy-C(n+1)-aldehyde;
   a polypeptide that catalyzes the conversion of the 2-hydroxy-C(n+1)-aldehyde to the 1,2-C(n+1)-diol, wherein the polypeptide is a 1,2-diol oxidoreductase or an alcohol dehydrogenase; and a diol dehydratase that catalyzes the conversion of the 1,2-C(n+1)-diol to the C(n+1)-aldehyde.

7. The method of claim 6, wherein:
a) the 2-hydroxyacyl-CoA lyase is encoded by a DNA molecule selected from *Homo sapiens* hacl1, *Rattus norvegicus* hacl1, *Dictyostelium discoideum* hacl1, and *Mus musculus* hacl1,
b) the acyl-CoA reductase is encoded by a DNA molecule selected from *Acinetobacter calcoaceticus* acr1, *Acinetobacter* sp Strain M-1 acrM, *Clostridium beijerinckii* ald, *E. coli* eutE, *Salmonella enterica* eutE, and *E. coli* mhpF;
c) the 1,2-diol oxidoreductase or alcohol dehydrogenase is encoded by a DNA molecule selected from *E. coli* betA, *E. coli* dkgA, *E. coli* eutG, *E. coli* fucO, *E. coli* ucpA, *E. coli* yahK, *E. coli* ybbO, *E. coli* ybdH, *E. coli* yiaY, and *E. coli* yjgB; and
d) the diol dehydratase is encoded by a DNA molecule selected from *Klebsiella ocytoca* pddABC, *E. coli* pduCDE, and *S. enterica* pduCDE.

8. The method of claim 1, wherein the conversion of the 2-hydroxy-C(n+1)-acyl-CoA to the C(n+1)-aldehyde comprises the steps of:
i. conversion of the 2-hydroxy-C(n+1)-acyl-CoA to a trans-2-C(n+1)-enoyl-CoA;
ii. conversion the trans-2-C(n+1)-enoyl-CoA to a C(n+1)-acyl-CoA; and
iii. conversion the C(n+1)-acyl-CoA to the C(n+1)-aldehyde.

9. The method of claim 8, wherein the one or more polypeptides that catalyzes the conversion of the 2-hydroxy-C(n+1)-acyl-CoA to the C(n+1)-aldehyde comprises:
a 2-hydroxyacyl-CoA dehydratase that catalyzes the conversion of the 2-hydroxy-C(n+1)-acyl-CoA to a trans-2-C(n+1)-enoyl-CoA;
a trans-2-enoyl-CoA reductase that catalyzes the conversion the trans-2-C(n+1)-enoyl-CoA to a C(n+1)-acyl-CoA; and
an acyl-CoA reductase that catalyzes the conversion the C(n+1)-acyl-CoA to the C(n+1)-aldehyde.

10. The method of claim 9, wherein:
a) the 2-hydroxyacyl-CoA lyase is encoded by a first heterologous DNA molecule encoding the selected from *Homo sapiens* hacl1, *Rattus norvegicus* hacl1, *Dictyostelium discoideum* hacl1, and *Mus musculus* hacl1, and wherein the oxalyl-CoA decarboxylase is encoded by a DNA molecule selected from *Mycobacterium* sp. MOTT36Y W7S_25140, *Mycobacterium tuberculosis* TKK-01-0051 K875_00487, *Polynucleobacter necessarius* subsp. asymbioticus QLW-P1DMWA-1 Pnuc_0637, and *E. coli* oxc;
b) the 2-hydroxyacyl-CoA dehydratase is encoded by a DNA molecule selected from *Clostridium propionicum* lcdABC, and *Clostridium difficile* hadBCI; and
c) the trans-2-enoyl-CoA reductase is encoded by a DNA molecule selected from *Rhodobacter sphaeroides* AcuI, *E. coli* yhdH, *E. coli* fabI, *Enterococcus faecalis* fabK, *Bacillus subtilis* fabL, *Euglena gracilis* TER, *Treponema denticola* TER, and *Vibrio cholera* fabV; and
d) the acyl-CoA reductase is encoded by a DNA molecule selected from *Acinetobacter calcoaceticus* acr1, *Acinetobacter* sp Strain M-1 acrM, *Clostridium beijerinckii* ald, *E. coli* eutE, *Salmonella enterica* eutE, and *E. coli* mhpF.

11. The method of claim 1, wherein the single carbon substrate is carbon dioxide, and wherein the conversion of the carbon dioxide to formyl-CoA comprises the steps of:
a) conversion of the carbon dioxide to formate;
b) conversion of the formate to formyl-phosphate; and
c) conversion of the formyl-phosphate to the formyl-CoA.

12. The method of claim 11, wherein the one or more polypeptides that catalyze the conversion of the carbon dioxide to the formyl-CoA comprise:
a) a carbon dioxide reductase that catalyzes the conversion of the carbon dioxide to formate;
b) an acetate kinase or formate kinase that catalyzes the conversion of the formate to formyl-phosphate; and
c) a phosphate acetyl-transferase that catalyzes the conversion of the formyl-phosphate to the formyl-CoA.

13. The method of claim 6, wherein the one or more polypeptides that catalyze the conversion of the carbon dioxide to the formyl-CoA comprise:
a) a carbon dioxide reductase that catalyzes the conversion of the carbon dioxide to formate;
b) an acetate kinase or formate kinase that catalyzes the conversion of the formate to formyl-phosphate; and
c) a phosphate acetyl-transferase that catalyzes the conversion of the formyl-phosphate to the formyl-CoA.

14. The method of claim 12, wherein:
a) the carbon dioxide reductase is encoded by a DNA molecule selected from *Acetobacterium woodii* fdhF2, *Acetobacterium woodii* hycB2, *Acetobacterium woodii* hycB3, and *Acetobacterium woodii* hydA2;
b) the formate kinase is encoded by a DNA molecule selected from *Salmonella typhimurium* stAckA, and *E. coli* AckA and c) the phosphate acetyl-transferase is encoded by a DNA molecule selected from *E. coli* eutD, *E. coli* pta, and *Salmonella typhimurium* PduL.

15. The method of claim 1, wherein the single carbon substrate is formate and wherein the one or more polypeptides that catalyze the conversion of the formate to formyl-CoA is acetyl-CoA synthetase.

16. The method of claim 15, wherein the acetyl-CoA synthetase is encoded by *Escherichia coli* acs.

17. The method of claim 1, wherein the single carbon substrate is methane or methanol, and wherein when the single carbon substrate is methane, the method comprises conversion of methane to methanol.

18. The method of claim 17, wherein the conversion of methanol to formyl-CoA comprises:
a) conversion of methanol to formaldehyde; and
b) conversion of formaldehyde to formyl-CoA.

19. The method of claim 18, wherein:
a) a methanol dehydrogenase catalyzes the conversion of the methanol to the formaldehyde; and
b) an acylating aldehyde dehydrogenase catalyzes the conversion of the formaldehyde to the formyl-CoA.

20. The method of claim 6, wherein the single carbon substrate is methane or methanol, and wherein when the single carbon substrate is methane, the method comprises conversion of the methane to methanol, and wherein:
a) a methanol dehydrogenase catalyzes the conversion of the methanol to the formaldehyde; and
b) an acylating aldehyde dehydrogenase catalyzes the conversion of the formaldehyde to the formyl-CoA.

21. The method of claim 19, wherein:
a) the methanol dehydrogenase is encoded by a DNA molecule selected from *Bacillus methanolicus* mdh, *Mycobacterium* sp. DSM 3803 mdo, and *Methylobacterium extorquens* moxI, moxF; and b) the acylating aldehyde dehydrogenase is encoded by a DNA molecule selected from *E. coli* mhpF, and *Pseudomonas* sp. CF600 dmpF.

22. The method of claim 17, wherein the single carbon substrate is methane and wherein a methane monooxygenase catalyzes the conversion of the methane to methanol.

23. The method of claim 1, wherein the product is a carboxylic acid.

24. The method of claim 23, wherein the carboxylic acid is selected from the group consisting of (3R)-β-hydroxy carboxylic acids, or (2R)-α-hydroxycarboxylic acids, and b-keto carboxylic acids, or α,β-unsaturated carboxylic acids.

25. The method of claim 23, wherein the method comprises the conversion of an acyl-CoA to the carboxylic acid.

26. The method of claim 1, wherein the product is selected from the group consisting of primary alcohols, or 1, (3R)-β diols, or 1, (2R)-α diols, or α-keto primary alcohols, or α,β-unsaturated primary alcohols.

27. The method of claim 26, wherein the method comprises the conversion of an acyl-CoA to the alcohol.

28. The method of claim 1, wherein the product is selected from the group consisting of linear alkanes, or linear alkan-3-ols, or linear alkan-2-ols, or linear methyl-ketones, or 1-alkenes.

29. The method of claim 1, wherein the product is an amine selected from the group consisting of primary amines, or 3-hydroxy-amines, or 2-hydroxy-amines, or 3-keto-amines, or α,β-unsaturated primary amines.

30. The method of claim 29, wherein the method comprises the conversion of an aldehyde to the amine.

31. The method of claim 1, wherein the microorganism further expresses a polypeptide selected from the group consisting of a thioesterase, acyl-CoA:acetyl-CoA transferase, phosphotransacylase, carboxylate kinase, an alcohol-forming coenzyme-A thioester reductase, an aldehyde-forming coenzyme-A thioester reductase, an alcohol dehydrogenase, an aldehyde decarbonylase; and a transaminase.

32. The method of claim 1, wherein the method further comprises regeneration of the C(n)-aldehyde and wherein the regeneration comprises:
   i. conversion of a trans-2-enoyl-CoA to a 3-hydroxy-acyl-CoA;
   ii. conversion of the 3-hydroxy-acyl-CoA to a 3-keto-acyl-CoA;
   iii. conversion of the 3-keto-acyl-CoA to acetyl-CoA and an acyl-CoA shortened by two carbons; and
   iv. conversion of the acetyl-CoA to the acetaldehyde.

33. The method of claim 32, wherein:
a) an enoyl-CoA hydratase catalyzes the conversion of the trans-2-enoyl-CoA to the 3-hydroxy-acyl-CoA;
b) a 3-hydroxyacyl-CoA dehydrogenase catalyzes the conversion of the 3-hydroxy-acyl-CoA to the 3-keto-acyl-CoA;
c) a 3-ketoacyl-CoA thiolase catalyzes the conversion of the 3-keto-acyl-CoA to the acetyl-CoA and the acyl-CoA shortened by two carbons; and
d) an acetyl-CoA reductase catalyzes the conversion of the acetyl-CoA to the acetaldehyde.

34. The method of claim 33, wherein:
a) the enoyl-CoA hydratase is encoded by a DNA molecule selected from *E. coli* fadB, *E. coli* fadJ, *Aeromonas caviae* phaJ, *Pseudomonas aeruginosa* phaJ1, *Pseudomonas aeruginosa* phaJ2, *Pseudomonas aeruginosa* phaJ3, and *Pseudomonas aeruginosa* phaJ4;
b) the 3-hydroxyacyl-CoA dehydrogenase is encoded by a DNA molecule selected from *E. coli* fadB, *E. coli* fadJ, *Ralstonia eutropha* phaB1, *Ralstonia eutropha* phaB2, and *Ralstonia eutropha* phaB3;
c) the 3-ketoacyl-CoA thiolase is encoded by a DNA molecule selected-from *E. coli* atoB, *E. coli* yqeF, *E. coli* fadA, *E. coli* fadI, *Ralstonia eutropha* bktB, *Pseudomonas* sp. Strain B13 catF, *E coli* paaJ, *Rhodococcus opacus* pcaF, *Streptomyces* sp. pcaF, *Ralstonia eutropha* phaA, *Clostridium acetobutylicum* thlA, and *Clostridium acetobutylicum* thlB;
d) the acetyl-CoA reductase is encoded by a DNA molecule selected from *E. coli* eutE, *Salmonella enterica* eutE, and *E. coli* mhpF.

35. The method of claim 32, wherein the microorganism further expresses a polypeptide selected from the group consisting of a thioesterase, acyl-CoA:acetyl-CoA transferase, phosphotransacylase, carboxylate kinase, an alcohol-forming coenzyme-A thioester reductase, an aldehyde-forming coenzyme-A thioester reductase, an alcohol dehydrogenase, an aldehyde decarbonylase; and a transaminase.

36. The method of claim 1, wherein the microorganism is selected from the group consisting of *E. coli, S. cerevisiae, Methylococcus capsulatus, Pichia pastoris, Arxula adeninivorans, Candida boidinii, Hansenula polymorpha, Kluyveromyces lactis, Yarrowia lipolytica, Laminaria japonica, Undaria pinnatifida, Pavlova lutheri,* and *Crypthecodinium cohni.*

* * * * *

SEQUENCE LISTING

```
<160> NUMBER OF SEQ ID NOS: 4

<210> SEQ ID NO 1
<211> LENGTH: 578
<212> TYPE: PRT
<213> ORGANISM: Homo sapiens
```

```
<400> SEQUENCE: 1

Met Pro Asp Ser Asn Phe Ala Glu Arg Ser Glu Glu Gln Val Ser Gly
1               5                   10                  15

Ala Lys Val Ile Ala Gln Ala Leu Lys Thr Gln Asp Val Glu Tyr Ile
            20                  25                  30

Phe Gly Ile Val Gly Ile Pro Val Thr Glu Ile Ala Ile Ala Ala Gln
        35                  40                  45

Gln Leu Gly Ile Lys Tyr Ile Gly Met Arg Asn Glu Gln Ala Ala Cys
    50                  55                  60

Tyr Ala Ala Ser Ala Ile Gly Tyr Leu Thr Ser Arg Pro Gly Val Cys
65                  70                  75                  80

Leu Val Val Ser Gly Pro Gly Leu Ile His Ala Leu Gly Gly Met Ala
                85                  90                  95

Asn Ala Asn Met Asn Cys Trp Pro Leu Leu Val Ile Gly Gly Ser Ser
            100                 105                 110

Glu Arg Asn Gln Glu Thr Met Gly Ala Phe Gln Glu Phe Pro Gln Val
        115                 120                 125

Glu Ala Cys Arg Leu Tyr Thr Lys Phe Ser Ala Arg Pro Ser Ser Ile
    130                 135                 140

Glu Ala Ile Pro Phe Val Ile Glu Lys Ala Val Arg Ser Ser Ile Tyr
145                 150                 155                 160

Gly Arg Pro Gly Ala Cys Tyr Val Asp Ile Pro Ala Asp Phe Val Asn
                165                 170                 175

Leu Gln Val Asn Val Asn Ser Ile Lys Tyr Met Glu Arg Cys Met Ser
            180                 185                 190

Pro Pro Ile Ser Met Ala Glu Thr Ser Ala Val Cys Thr Ala Ala Ser
        195                 200                 205

Val Ile Arg Asn Ala Lys Gln Pro Leu Leu Ile Ile Gly Lys Gly Ala
210                 215                 220

Ala Tyr Ala His Ala Glu Glu Ser Ile Lys Lys Leu Val Glu Gln Tyr
225                 230                 235                 240

Lys Leu Pro Phe Leu Pro Thr Pro Met Gly Lys Gly Val Val Pro Asp
                245                 250                 255

Asn His Pro Tyr Cys Val Gly Ala Ala Arg Ser Arg Ala Leu Gln Phe
            260                 265                 270

Ala Asp Val Ile Val Leu Phe Gly Ala Arg Leu Asn Trp Ile Leu His
        275                 280                 285

Phe Gly Leu Pro Pro Arg Tyr Gln Pro Asp Val Lys Phe Ile Gln Val
    290                 295                 300

Asp Ile Cys Ala Glu Glu Leu Gly Asn Asn Val Lys Pro Ala Val Thr
305                 310                 315                 320

Leu Leu Gly Asn Ile His Ala Val Thr Lys Gln Leu Leu Glu Glu Leu
                325                 330                 335

Asp Lys Thr Pro Trp Gln Tyr Pro Pro Glu Ser Lys Trp Trp Lys Thr
            340                 345                 350

Leu Arg Glu Lys Met Lys Ser Asn Glu Ala Ala Ser Lys Glu Leu Ala
        355                 360                 365

Ser Lys Lys Ser Leu Pro Met Asn Tyr Tyr Thr Val Phe Tyr His Val
    370                 375                 380

Gln Glu Gln Leu Pro Arg Asp Cys Phe Val Val Ser Glu Gly Ala Asn
385                 390                 395                 400

Thr Met Asp Ile Gly Arg Thr Val Leu Gln Asn Tyr Leu Pro Arg His
```

```
            405                 410                 415
Arg Leu Asp Ala Gly Thr Phe Gly Thr Met Gly Val Gly Leu Gly Phe
            420                 425                 430

Ala Ile Ala Ala Val Val Ala Lys Asp Arg Ser Pro Gly Gln Trp
            435                 440                 445

Ile Ile Cys Val Glu Gly Asp Ser Ala Phe Gly Phe Ser Gly Met Glu
            450                 455                 460

Val Glu Thr Ile Cys Arg Tyr Asn Leu Pro Ile Ile Leu Leu Val Val
465                 470                 475                 480

Asn Asn Asn Gly Ile Tyr Gln Gly Phe Asp Thr Asp Thr Trp Lys Glu
            485                 490                 495

Met Leu Lys Phe Gln Asp Ala Thr Ala Val Val Pro Pro Met Cys Leu
            500                 505                 510

Leu Pro Asn Ser His Tyr Glu Gln Val Met Thr Ala Phe Gly Gly Lys
            515                 520                 525

Gly Tyr Phe Val Gln Thr Pro Glu Glu Leu Gln Lys Ser Leu Arg Gln
            530                 535                 540

Ser Leu Ala Asp Thr Thr Lys Pro Ser Leu Ile Asn Ile Met Ile Glu
545                 550                 555                 560

Pro Gln Ala Thr Arg Lys Ala Gln Asp Phe His Trp Leu Thr Arg Ser
            565                 570                 575

Asn Met

<210> SEQ ID NO 2
<211> LENGTH: 551
<212> TYPE: PRT
<213> ORGANISM: Homo sapiens

<400> SEQUENCE: 2

Met Pro Asp Ser Asn Phe Ala Glu Arg Ser Glu Gln Val Ser Gly
1               5                   10                  15

Ala Lys Val Ile Ala Gln Ala Leu Lys Thr Gln Asp Val Glu Tyr Ile
                20                  25                  30

Phe Gly Ile Val Gly Ile Pro Val Thr Glu Ile Ala Ile Ala Ala Gln
            35                  40                  45

Gln Leu Gly Ile Lys Tyr Ile Gly Met Arg Asn Glu Gln Ala Ala Cys
        50                  55                  60

Tyr Ala Ala Ser Ala Ile Gly Tyr Leu Thr Ser Arg Pro Leu Leu Val
65                  70                  75                  80

Ile Gly Gly Ser Ser Glu Arg Asn Gln Glu Thr Met Gly Ala Phe Gln
                85                  90                  95

Glu Phe Pro Gln Val Glu Ala Cys Arg Leu Tyr Thr Lys Phe Ser Ala
            100                 105                 110

Arg Pro Ser Ser Ile Glu Ala Ile Pro Phe Val Ile Glu Lys Ala Val
        115                 120                 125

Arg Ser Ser Ile Tyr Gly Arg Pro Gly Ala Cys Tyr Val Asp Ile Pro
        130                 135                 140

Ala Asp Phe Val Asn Leu Gln Val Asn Val Asn Ser Ile Lys Tyr Met
145                 150                 155                 160

Glu Arg Cys Met Ser Pro Pro Ile Ser Met Ala Glu Thr Ser Ala Val
                165                 170                 175

Cys Thr Ala Ala Ser Val Ile Arg Asn Ala Lys Gln Pro Leu Leu Ile
            180                 185                 190

Ile Gly Lys Gly Ala Ala Tyr Ala His Ala Glu Glu Ser Ile Lys Lys
```

-continued

```
            195                 200                 205
Leu Val Glu Gln Tyr Lys Leu Pro Phe Leu Pro Thr Pro Met Gly Lys
210                 215                 220

Gly Val Val Pro Asp Asn His Pro Tyr Cys Val Gly Ala Ala Arg Ser
225                 230                 235                 240

Arg Ala Leu Gln Phe Ala Asp Val Ile Val Leu Phe Gly Ala Arg Leu
                245                 250                 255

Asn Trp Ile Leu His Phe Gly Leu Pro Pro Arg Tyr Gln Pro Asp Val
                260                 265                 270

Lys Phe Ile Gln Val Asp Ile Cys Ala Glu Glu Leu Gly Asn Asn Val
                275                 280                 285

Lys Pro Ala Val Thr Leu Leu Gly Asn Ile His Ala Val Thr Lys Gln
290                 295                 300

Leu Leu Glu Glu Leu Asp Lys Thr Pro Trp Gln Tyr Pro Pro Glu Ser
305                 310                 315                 320

Lys Trp Trp Lys Thr Leu Arg Glu Lys Met Lys Ser Asn Glu Ala Ala
                325                 330                 335

Ser Lys Glu Leu Ala Ser Lys Lys Ser Leu Pro Met Asn Tyr Tyr Thr
                340                 345                 350

Val Phe Tyr His Val Gln Glu Gln Leu Pro Arg Asp Cys Phe Val Val
                355                 360                 365

Ser Glu Gly Ala Asn Thr Met Asp Ile Gly Arg Thr Val Leu Gln Asn
370                 375                 380

Tyr Leu Pro Arg His Arg Leu Asp Ala Gly Thr Phe Gly Thr Met Gly
385                 390                 395                 400

Val Gly Leu Gly Phe Ala Ile Ala Ala Val Val Ala Lys Asp Arg
                405                 410                 415

Ser Pro Gly Gln Trp Ile Ile Cys Val Glu Gly Asp Ser Ala Phe Gly
                420                 425                 430

Phe Ser Gly Met Glu Val Glu Thr Ile Cys Arg Tyr Asn Leu Pro Ile
                435                 440                 445

Ile Leu Leu Val Val Asn Asn Asn Gly Ile Tyr Gln Gly Phe Asp Thr
450                 455                 460

Asp Thr Trp Lys Glu Met Leu Lys Phe Gln Asp Ala Thr Ala Val Val
465                 470                 475                 480

Pro Pro Met Cys Leu Leu Pro Asn Ser His Tyr Glu Gln Val Met Thr
                485                 490                 495

Ala Phe Gly Gly Lys Gly Tyr Phe Val Gln Thr Pro Glu Glu Leu Gln
                500                 505                 510

Lys Ser Leu Arg Gln Ser Leu Ala Asp Thr Thr Lys Pro Ser Leu Ile
                515                 520                 525

Asn Ile Met Ile Glu Pro Gln Ala Thr Arg Lys Ala Gln Asp Phe His
                530                 535                 540

Trp Leu Thr Arg Ser Asn Met
545                 550

<210> SEQ ID NO 3
<211> LENGTH: 496
<212> TYPE: PRT
<213> ORGANISM: Homo sapiens

<400> SEQUENCE: 3

Met Pro Asp Ser Asn Phe Ala Glu Arg Ser Glu Glu Gln Val Ser Gly
1               5                   10                  15
```

```
Ala Lys Val Ile Ala Gln Ala Leu Lys Thr Gln Asp Val Glu Tyr Ile
             20                  25                  30

Phe Gly Ile Val Gly Ile Pro Val Thr Glu Ile Ala Ile Ala Ala Gln
         35                  40                  45

Gln Leu Gly Ile Lys Tyr Ile Gly Met Arg Asn Glu Gln Ala Ala Cys
     50                  55                  60

Tyr Ala Ala Ser Ala Ile Gly Tyr Leu Thr Ser Arg Pro Gly Val Cys
65                  70                  75                  80

Leu Val Val Ser Gly Pro Gly Leu Ile His Ala Leu Gly Gly Met Ala
                 85                  90                  95

Asn Ala Asn Met Asn Cys Trp Tyr Met Glu Arg Cys Met Ser Pro Pro
             100                 105                 110

Ile Ser Met Ala Glu Thr Ser Ala Val Cys Thr Ala Ala Ser Val Ile
         115                 120                 125

Arg Asn Ala Lys Gln Pro Leu Leu Ile Ile Gly Lys Gly Ala Ala Tyr
    130                 135                 140

Ala His Ala Glu Glu Ser Ile Lys Lys Leu Val Glu Gln Tyr Lys Leu
145                 150                 155                 160

Pro Phe Leu Pro Thr Pro Met Gly Lys Gly Val Val Pro Asp Asn His
                165                 170                 175

Pro Tyr Cys Val Gly Ala Ala Arg Ser Arg Ala Leu Gln Phe Ala Asp
            180                 185                 190

Val Ile Val Leu Phe Gly Ala Arg Leu Asn Trp Ile Leu His Phe Gly
        195                 200                 205

Leu Pro Pro Arg Tyr Gln Pro Asp Val Lys Phe Ile Gln Val Asp Ile
210                 215                 220

Cys Ala Glu Glu Leu Gly Asn Asn Val Lys Pro Ala Val Thr Leu Leu
225                 230                 235                 240

Gly Asn Ile His Ala Val Thr Lys Gln Leu Leu Glu Glu Leu Asp Lys
                245                 250                 255

Thr Pro Trp Gln Tyr Pro Pro Glu Ser Lys Trp Trp Lys Thr Leu Arg
            260                 265                 270

Glu Lys Met Lys Ser Asn Glu Ala Ala Ser Lys Glu Leu Ala Ser Lys
        275                 280                 285

Lys Ser Leu Pro Met Asn Tyr Tyr Thr Val Phe Tyr His Val Gln Glu
290                 295                 300

Gln Leu Pro Arg Asp Cys Phe Val Val Ser Glu Gly Ala Asn Thr Met
305                 310                 315                 320

Asp Ile Gly Arg Thr Val Leu Gln Asn Tyr Leu Pro Arg His Arg Leu
            325                 330                 335

Asp Ala Gly Thr Phe Gly Thr Met Gly Val Gly Leu Gly Phe Ala Ile
        340                 345                 350

Ala Ala Ala Val Val Ala Lys Asp Arg Ser Pro Gly Gln Trp Ile Ile
    355                 360                 365

Cys Val Glu Gly Asp Ser Ala Phe Gly Phe Ser Gly Met Glu Val Glu
370                 375                 380

Thr Ile Cys Arg Tyr Asn Leu Pro Ile Ile Leu Val Val Asn Asn Asn
385                 390                 395                 400

Asn Gly Ile Tyr Gln Gly Phe Asp Thr Asp Thr Trp Lys Glu Met Leu
            405                 410                 415

Lys Phe Gln Asp Ala Thr Ala Val Val Pro Pro Met Cys Leu Leu Pro
        420                 425                 430

Asn Ser His Tyr Glu Gln Val Met Thr Ala Phe Gly Gly Lys Gly Tyr
```

```
                435                 440                 445
Phe Val Gln Thr Pro Glu Glu Leu Gln Lys Ser Leu Arg Gln Ser Leu
    450                 455                 460
Ala Asp Thr Thr Lys Pro Ser Leu Ile Asn Ile Met Ile Glu Pro Gln
465                 470                 475                 480
Ala Thr Arg Lys Ala Gln Asp Phe His Trp Leu Thr Arg Ser Asn Met
                485                 490                 495

<210> SEQ ID NO 4
<211> LENGTH: 518
<212> TYPE: PRT
<213> ORGANISM: Homo sapiens

<400> SEQUENCE: 4

Met Pro Asp Ser Asn Phe Ala Glu Arg Ser Glu Glu Gln Val Ser Gly
1               5                   10                  15
Ala Lys Val Ile Ala Gln Ala Leu Lys Thr Gln Asp Val Glu Tyr Ile
                20                  25                  30
Phe Gly Ile Val Gly Ile Pro Val Thr Glu Ile Ala Ile Ala Ala Gln
            35                  40                  45
Gln Leu Gly Ile Lys Tyr Ile Gly Met Arg Asn Glu Gln Ala Ala Cys
    50                  55                  60
Tyr Ala Ala Ser Ala Ile Gly Tyr Leu Thr Ser Arg Pro Gly Val Cys
65              70                  75                  80
Leu Val Val Ser Gly Pro Gly Leu Ile His Ala Leu Gly Gly Met Ala
                85                  90                  95
Asn Ala Asn Met Asn Cys Trp Pro Leu Leu Val Ile Gly Gly Ser Ser
            100                 105                 110
Glu Arg Asn Gln Glu Thr Met Gly Ala Phe Gln Glu Phe Pro Gln Ala
    115                 120                 125
Val Arg Ser Ser Ile Tyr Gly Arg Pro Gly Ala Cys Tyr Val Asp Ile
130                 135                 140
Pro Ala Asp Phe Val Asn Leu Gln Val Asn Val Asn Ser Ile Lys Tyr
145                 150                 155                 160
Met Glu Arg Cys Met Ser Pro Pro Ile Ser Met Ala Glu Thr Ser Ala
                165                 170                 175
Val Cys Thr Ala Ala Ser Val Ile Arg Asn Ala Lys Gln Pro Leu Leu
            180                 185                 190
Ile Ile Gly Lys Gly Ala Ala Tyr Ala His Ala Glu Glu Ser Ile Lys
    195                 200                 205
Lys Leu Val Glu Gln Tyr Lys Leu Pro Phe Leu Pro Thr Pro Met Gly
    210                 215                 220
Lys Gly Val Val Pro Asp Asn His Pro Tyr Cys Val Gly Ala Ala Arg
225                 230                 235                 240
Ser Arg Ala Leu Gln Phe Ala Asp Val Ile Val Leu Phe Gly Ala Arg
                245                 250                 255
Leu Asn Trp Ile Leu His Phe Gly Leu Pro Pro Arg Tyr Gln Pro Asp
            260                 265                 270
Val Lys Phe Ile Gln Val Asp Ile Cys Ala Glu Glu Leu Gly Asn Asn
    275                 280                 285
Val Lys Pro Ala Val Thr Leu Leu Gly Asn Ile His Ala Val Thr Lys
290                 295                 300
Gln Glu Leu Ala Ser Lys Lys Ser Leu Pro Met Asn Tyr Tyr Thr Val
305                 310                 315                 320
```

-continued

```
Phe Tyr His Val Gln Glu Gln Leu Pro Arg Asp Cys Phe Val Val Ser
            325                 330                 335

Glu Gly Ala Asn Thr Met Asp Ile Gly Arg Thr Val Leu Gln Asn Tyr
            340                 345                 350

Leu Pro Arg His Arg Leu Asp Ala Gly Thr Phe Gly Thr Met Gly Val
            355                 360                 365

Gly Leu Gly Phe Ala Ile Ala Ala Val Val Ala Lys Asp Arg Ser
    370                 375                 380

Pro Gly Gln Trp Ile Ile Cys Val Glu Gly Asp Ser Ala Phe Gly Phe
385                 390                 395                 400

Ser Gly Met Glu Val Glu Thr Ile Cys Arg Tyr Asn Leu Pro Ile Ile
            405                 410                 415

Leu Leu Val Val Asn Asn Asn Gly Ile Tyr Gln Gly Phe Asp Thr Asp
            420                 425                 430

Thr Trp Lys Glu Met Leu Lys Phe Gln Asp Ala Thr Ala Val Val Pro
            435                 440                 445

Pro Met Cys Leu Leu Pro Asn Ser His Tyr Glu Gln Val Met Thr Ala
    450                 455                 460

Phe Gly Gly Lys Gly Tyr Phe Val Gln Thr Pro Glu Glu Leu Gln Lys
465                 470                 475                 480

Ser Leu Arg Gln Ser Leu Ala Asp Thr Thr Lys Pro Ser Leu Ile Asn
            485                 490                 495

Ile Met Ile Glu Pro Gln Ala Thr Arg Lys Ala Gln Asp Phe His Trp
            500                 505                 510

Leu Thr Arg Ser Asn Met
            515
```